US007070772B2

(12) United States Patent
Wildermuth et al.

(10) Patent No.: US 7,070,772 B2
(45) Date of Patent: Jul. 4, 2006

(54) SALICYLIC ACID BIOSYNTHETIC GENES AND USES THEREOF

(75) Inventors: Mary C. Wildermuth, Cambridge, MA (US); Frederick M. Ausubel, Newton, MA (US); Julia Dewdney, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 292 days.

(21) Appl. No.: 09/908,299

(22) Filed: Jul. 18, 2001

(65) Prior Publication Data

US 2003/0051273 A1 Mar. 13, 2003

Related U.S. Application Data

(60) Provisional application No. 60/219,231, filed on Jul. 18, 2000.

(51) Int. Cl.
*A01H 5/00* (2006.01)
*A01N 63/04* (2006.01)
(52) U.S. Cl. ..................... 424/93.5; 800/301
(58) Field of Classification Search .............. 435/15, 435/29; 534/23.2, 23.6; 800/301; 424/93.5
See application file for complete search history.

(56) References Cited

FOREIGN PATENT DOCUMENTS

WO        WO 99/50423        10/1999

OTHER PUBLICATIONS van Tegelen et al 1999, Plant Physiology, Feb. 1999, 119: 705-712.*
Richmond et al 2000, Plant Physiology 124:495-498 at 497.*
Duggleby 1997, Gene 190:245-249.*
Nawarath and Métraux Aug. 1999, The Plant Cell 11: 1393-1404.*
Ferrari et al 2003, The Plant Journal 35: 193-205.*
Asai et al., "Fumonisin B1-Induced Cell Death in Arabidopsis Protoplasts Requires Jasmonate-, Ethylene- and Salicylate-Dependent Signaling Pathways," *Plant Cell* 12:1823-1835 (2000).
Bender and Fink, "A Myb Homologue, ATR1, Activates Tryptophan Gene Expression in Arabidopsis," *Proc. Natl. Acad. Sci. USA* 95:5655-5660 (1998).
Bohlmann et al, "Purification and cDNA Cloning of Anthranilate Synthase from *Ruta graveolens*: Modes of Expression and Properties of Native and Recombinant Enzymes," *Plant J.* 7:491-501 (1995).
Bowling et al., "A Mutation in Arabidopsis that Leads to Constitutive Expression of Systemic Acquired Resistance," *Plant Cell* 6:1845-1857 (1994).

Bowling et al., "The *cpr5* Mutant of Arabidopsis Expresses both *NPR1*-Dependent and *NPR1*-Independent Resistance," *Plant Cell* 9:1573-1584 (1997).
Cao et al., "Characterization of an Arabidopsis Mutant that is Nonresponsive to Inducers of Systemic Acquired Resistance," *Plant Cell* 6:1583-1592 (1994).
Cao et al., "The Arabidopsis *NPR1* Gene that Controls Systemic Acquired Resistance Encodes a Novel Protein Containing Ankyrin Repeats," *Cell* 88:57-63 (1997).
Clarke et al., "Uncoupling PR Gene Expression from *NPR1* and Bacterial Resistance: Characterization of the Dominant Arabidopis *cpr6-1* Mutant," *Plant Cell* 10:557-569 (1998).
Coquoz et al., "The Biosynthesis of Salicylic Acid in Potato Plants," *Plant Physiol.* 117:1095-1101 (1998).
Delaney et al., "Arabidopsis Signal Transduction Mutant Defective in Chemically and Biologically Induced Disease Resistance," *Proc. Natl. Acad. Sci. USA* 92:6602-6606 (1995).
Dempsey et al., "Salicylic Acid and Disease Resistance in Plants," *Crit. Rev. Plant Sci.* 18:547-575 (1999).
Despré s et al., "The Arabidopsis NPR1/NIM1 Protein Enhances the DNA Binding Activity of a Subgroup of the TGA Family of bZIP Transcription Factors," *Plant Cell* 12:279-290 (2000).
Dewdney et al., "Three Unique Mutants of Arabidopsis Identify *eds* Loci Required for Limiting Growth of a Biotrophic Fungal Pathogen," *Plant J.* 24:205-218 (2000).
Dorey et al., "Spatial and Temporal Induction of Cell Death, Defense Genes, and Accumulation of Salicylic Acid in Tobacco Leaves Reacting Hypersensitively to a Fungal Glycoprotein Elicitor," *Mol. Plant-Microbe Interact.* 10:646-655 (1997).
Eulgem et al., "The WRKY Superfamily of Plant Transcription Factors," *Trends Plant Sci.* 5: 199-206 (2000).
GenBank Accession No. AF078080. Dec. 23, 1998.
GenBank Accession No. AJ006065. Oct. 20, 1999.
Lebel et al., "Functional Analysis of Regulatory Sequences Controlling PR-1 Gene Expresson to Arabidopsis," *Plant J*, 16:223-233 (1998).
León et al., "Benzoic Acid 2-Hydroxylase, a Soluble Oxygenase from Tobacco, Catalyzes Salicylic Acid Biosynthesis," *Proc. Natl. Acad. Sci. USA* 92:10413-10417 (1995).

(Continued)

*Primary Examiner*—David H Kruse
(74) *Attorney, Agent, or Firm*—Clark & Elbing LLP

(57) ABSTRACT

The invention provides methods for inducing or increasing disease resistance in a plant. The invention also features methods of using a plant having a mutation in an inducible isochorismate synthase to determine if the success of a pathogen in infecting a plant is affected by a plant disease resistance pathway involving isochorismate synthase.

2 Claims, 26 Drawing Sheets

OTHER PUBLICATIONS

Malamy et al., "Salicylic Acid: A Likely Endogenous Signal in the Resistance Response of Tobacco to Viral Infection," *Science* 250:1002-1004 (1990).

Maleck et al., "The Transcriptome of *Arabidopsis thaliana* during Systemic Acquired Resistance," *Nature Genetics* 26:403-410 (2000).

Mauch et al., "Manipulation of Salicylate Content in *Arabidopsis thaliana* by the Expression of an Engineered Bacterial Salicylate Synthase," *Plant J.* 25:67-77 (2001).

Mauch-Mani et al., "Production of Salicylic Acid Precursors Is a Major Function of Phenylalanine Ammonia-Lyase in the Resistance of Arabidopsis to *Peronospora parasitica*," *Plant Cell* 8:203-212 (1996).

Meng et al., "Cloning of a Plant Isochorismate Synthase (Accession No. AF078080)" Plant Gene Register PGR98-214, *Plant Physiology* 118:1536 (1998).

Métraux et al., "Increase in Salicylic Acid at the Onset of Systemic Acquired Resistance in Cucumber," *Science* 250:1004-1006 (1990).

Nawrath et al., "Salicylic Acid Induction-Deficient Mutants of Arabidopsis Express *PR-2* and *PR-5* and Accumulate High Levels of Camalexin after Pathogen Inoculation," *Plant Cell* 11: 1393-1404 (1999).

Quadri et al., "Assembly of the *Pseudomonas aeruginosa* Nonribosomal Peptide Siderophore Pyochelin: In Vitro Reconstitution of Aryl-4,2-Bisthiazoline Synthetase Activity from PchD, PchE, and PchF," *Biochemistry* 38:14941-14954 (1999).

Ribnicky et al., "Intermediates of Salicylic Acid Biosynthesis in Tobacco," *Plant Physiol.* 118:565-572 (1998).

Ryals et al., "Systemic Acquired Resistance," *Plant Cell* 8:1809-1819 (1996).

Ryals et al., "The Arabidopsis *NIM1* Protein Shows Homology to the Mammalian Transcription Factor Inhibitor IkB," *Plant Cell* 9:425-439 (1997).

Serino et al., "Structural Genes for Salicylate Biosynthesis from Chorismate in *Pseudomonas aeruginosa*," *Mol. Gen. Genet.* 249:217-228 (1995).

Summermatter et al., "Systemic Responses in *Arabidopsis thaliana* Infected and Challenged with *Pseudomonas syringae pv syringae*," *Plant Physiol.* 108:1379-1385 (1995).

Uknes et al., "Biological Induction of Systemic Acquired Resistance in Arabidopsis," *Mol. Plant-Microbe Interact.* 6:692-698 (1993).

van Tegelen et al., "Purification and cDNA Cloning of Isochorismate Synthase from Elicited Cell Cultures of *Catharanthus roseus*," *Plant Physiol.* 119:705-712 (1999).

Verberne et al., "Overproduction of Salicylic Acid in Plants by Bacterial Transgenes Enhances Pathogen Resistance," *Nature Biotechnology* 18:779-783 (2000).

Vernooij et al., "Salicylic Acid Is not the Translocated Signal Responsible for Inducing Systemic Acquired Resistance but Is Required in Signal Transduction," *Plant Cell* 6:959-965 (1994).

Yalpani et al., "Pathway of Salicylic Acid Biosynthesis in Healthy and Virus-Inoculated Tobacco," *Plant Physiol.* 103:315-321 (1993).

Yang and Klessig, "Isolation and Characterization of a Tobacco Mosaic Virus-Inducible *myb* Oncogene Homolog from Tobacco," *Proc. Natl. Acad. Sci. USA* 93:14972-14977 (1996).

Wildermuth et al., "Isochorismate Synthase Is Required to Synthesize Salicylic Acid for Plant Defence," *Nature* 414:562-565 (2001).

* cited by examiner

FIG. 16B infected plants

|      | ICS1 | SA | PR1 |                    |
|------|------|-----|-----|--------------------|
| sid2 | --   | --  | --  | Deficient SAR, LAR |
| nahG | w.t. | --  | --  |                    |
| npr1 | +    | +   | -   |                    | uninfected plants

|      | ICS1 | SA | PR1 |                  |
|------|------|-----|-----|------------------|
| cpr1 | +    | +   | +   | Constitutive SAR |
| cpr5 | +    | ++  | +   |                  |
| cpr6 | +    | ++  | ++  |                  |

SALICYLIC ACID BIOSYNTHETIC GENES AND USES THEREOF

CROSS REFERENCE TO RELATED APPLICATIONS

This application claims benefit from U.S. provisional application No. 60/219,231 which was filed on Jul. 18, 2000

BACKGROUND OF THE INVENTION

This invention relates to methods of inducing disease resistance in plants.

Plant-Pathogen Interactions

When plants are attacked by pathogens, they mount a battery of defenses, including senescence of infected tissues, reinforcement of cell walls by crosslinking and synthesis of new cell wall components, and production of antimicrobial compounds, such as phytoalexins, defensins, and enzymes that degrade pathogen cell walls (reviewed in Gan et al., Plant Physiology 113:313–319, 1997; Glazebrook, Current Opinion in Plant Biology 2:280–286, 1999; and Somssich et al., Trends in Plant Science 3:86–90, 1998). If the plant and pathogen express resistance (R) and avirulence (avr) genes, respectively, which interact to trigger a hypersensitive response, the plant is able to successfully resist the pathogen and the relationship is termed "incompatible." In contrast, in a "compatible" interaction, the plant fails to resist the pathogen attack and disease ensues. Although many of the same defenses that are induced during an incompatible interaction are also activated during a compatible interaction, the induction is generally slower and/or less extensive (reviewed in Crute et al., Arabidopsis, Cold Spring Harbor Laboratory Press pp. 705–747, 1994; Draper, Trends in Plant Science 2:162–165, 1997; Van Camp et al., Trends in Plant Science 3:330–334, 1998; and Yang et al., Genes & Development 11:1621–1639, 1997), and the plant's defense response is insufficient to prevent colonization by the pathogen. However, in many compatible interactions, the plant is nonetheless able to limit pathogen propagation, as was demonstrated by the isolation of Arabidopsis mutants that are defective in defense-related processes, and consequently allow enhanced growth of virulent pathogen(s) (Glazebrook et al., Genetics 143:973–982, 1996; Rogers et al., The Plant Cell 9:305–316, 1997; and Volko et al., Genetics 149: 537–548, 1998).

Role of Salicylic Acid in Plant Defense Response

Salicylic acid (SA) is a crucial signaling molecule in the plant defense response to pathogen attack (Enyedi, et al., Cell 70:879–886, 1992). For example, SA plays an important role in so-called systemic acquired resistance, or SAR (Gaffney et al., Science 261:754–756, 1993). SAR is a phenomenon in which infection of a plant with a pathogen that activates R gene-mediated pathways leads to accumulation of PR proteins, such as PR1, BGL2, and PR5 in uninfected leaves, which concomitantly become resistant to a variety of pathogens (Enyedi, et al., supra and Malamy et al., Plant J. 2:643–654, 1992). Treatment of plants with SA leads to PR protein accumulation and pathogen resistance (Enyedi et al. supra and Malamy et al., supra). Importantly, localized SA-mediated activation of PR proteins is also involved in defense responses to virulent pathogens that do not elicit a localized plant defense response, known as the hypersensitive response (HR), illustrating how R gene-dependent and R gene-independent pathways can utilize some of the same signaling compounds and effectors (Reuber et al., Plant J. 16:473–485, 1998 and Zhou et al., Plant Cell 10:1021–1030, 1998). The role of SA signaling in SAR and other plant defense responses has been facilitated by the construction of transgenic plants that express a Pseudomonas putida gene, nahG, which depletes the endogenous pool of SA by converting it into catechol (Gaffney et al., supra). These so-called "nahG transgenic plants" fail to exhibit SAR and are more susceptible to a variety of bacterial and fungal pathogens (for example, see Gaffney et al., supra and Reuber et al., supra). Several Arabidopsis genes have been identified that affect SA signaling pathways. For example, mutant alleles of NPR1, which encodes a protein with ankyrin repeats (Cao et al., Cell 88:57–64, 1997 and Ryals et al., Plant Cell 9:425–439, 1997), fail to activate SAR and PR gene expression in response to SA and exhibit enhanced susceptibility to pathogens (Cao et al., Plant Cell 6:1583–1592, 1994; Delaney et al., Proc. Natl. Acad. Sci. U.S.A. 92:6602–6606, 1995; Glazebrook, et al., 1996; and Shah et al., Mol. Plant-Microbe Interact. 10:69–78, 1997). Two additional Arabidopsis genes that are involved in SA signaling are PAD4 and EDS5. pad4 and eds5 plants were identified on the basis that they are more susceptible to virulent pathogens such as Pseudomonas syringae and Erysiphe orontii (Glazebrook et al., 1996) and accumulate decreased levels of SA following pathogen attack (Zhou et al., supra and Nawrath et al., Plant Cell 11:1393–1404, 1999). eds5 is allelic to an independently isolated mutant called sid1, isolated on the basis of reduced SA accumulation in response to pathogen attack (Nawrath et al., supra). Studies using eds5/npr1 double mutants suggest that EDS5 operates in a SA-dependent, but NPR1-independent, pathway (Reuber et al., supra).

In addition to SA, recent studies have identified SA-independent resistance mechanisms in Arabidopsis that are mediated by jasmonic acid (JA) and ethylene (ET) (reviewed in Dong, Curr. Op. Plant Biol. 1:316–323, 1998 and Reymond et al., Curr. Op. Plant Biol. 1:404–411, 1998). For example, JA induces the accumulation of the antimicrobial peptides thionin and defensin, encoded by THI and PDF genes, respectively. This induction is blocked in the ethylene insensitive mutant ein2 and in the jasmonate-insensitive mutants jar1 and coi1, but is not affected in nahG transgenic plants (Penninckx et al., Plant Cell 8:2309–2323, 1996; Penninckx et al., Plant Cell 10:2103–2113, 1998; and Thomma et al., Proc. Natl. Acad. Sci. U.S.A. 95:15107–15111, 1998). The JA pathway, rather than SA-mediated pathways, appears to be particularly important in conferring resistance to necrotrophic fungal pathogens (Penninckx et al., 1996 and Thomma et al., 1998). The SA and JA pathways appear to be at least partially antagonistic (Dong, supra and Pieterse et al., Plant Cell 10:1571–1580, 1998). Another SA-independent but JA- and ET-dependent pathway is called ISR for induced systemic resistance (Pieterse et al., Plant Cell 8:1225–1237, 1996 and Pieterse et al., 1998). Interestingly, ISR, which is triggered by the biocontrol bacterium Pseudomonas fluorescens in association with Arabidopsis roots, is dependent on NPR1, indicating that the JA/ET and SA resistance pathways intersect (Pieterse et al., Trends Plant Sci. 4:52–58, 1999 and Pieterse et al., 1998).

Biosynthesis of Salicylic Acid

Early studies showed that salicylic acid in higher plants derives from the shikimate pathway (Zenk et al., Planzen. Z. Naturforsch 19B:398–405, 1964). The shikimate pathway occurs in microorganisms and plants, but not in animals (reviewed in Herrmann et al., Annu. Rev. Plant Physiol. Plant Mol. Biol. 50:473–503, 1999). The shikimate pathway links the metabolism of carbohydrates to the biosynthesis of aromatic compounds. Chorismate, the end product of this pathway, is the precursor of the aromatic amino acids, tryptophan, phenylalanine, and tyrosine, and a diverse array of aromatic secondary compounds. In higher plants, the shikimate pathway appears to be localized to the plastid, because shikimate pathway cDNAs encode proteins with amino terminal plastid import sequences (Id.). In addition, the chorismate-utilizing enzymes, anthranilate synthase (AS), chorismate mutase (CM), and isochorismate synthase (ICS) also contain putative plastid import sequences (Eberhard et al., FEBS Lett. 334:233–236, 1993; van Tegelen et al., Plant Physiol. 119:705–712, 1999; and Zhao et al., J. Biol. Chem. 270:6081–6087, 1995). The biosynthesis of salicylic acid in tobacco, cucumber, and potato has been deduced to occur via the conversion of phenylalanine to benzoic acid (Pathway 1 in FIG. 1). Evidence for this biosynthetic pathway includes (1) the dependence of SA biosynthesis on phenylalanine ammonia lyase (PAL) activity, (2) numerous radiolabeling studies, and (3) the isolation of a TMV-inducible benzoic acid 2-hydroxylase activity (BA2H) in tobacco (Coquez et al., Plant Physiol. 117: 1095–1101, 1998; Leon et al., Plant Physiol. 103:323–328, 1993; Meuwly et al., Plant Physiol. 109:1107–1114, 1995; Ribnicky et al., Plant Physiol. 118:565–572, 1998; and Yalpani et al., Phytopathology 83:702–708, 1993). Though BA2H activity was first identified in 1993 (Leon et al., supra), the cloning of the corresponding gene has not been reported.

*Pseudomonas aeruginosa* synthesizes salicylic acid from chorismate utilizing isochorismate synthase (PchA) and pyruvate lyase (PchB) genes (Serino et al., Mol. Gen. Genet. 249:217–228, 1995). It should be noted, however, that many bacteria contain isochorismate synthases, and that these enzymes are involved in processes other than salicylic acid production. For example, in *E. coli*, there is an isochorismate synthase required for menaquinone production (MenF), and another involved in enterobactin (a siderophore (i.e., an iron-binding compound)) synthesis (EntC). In the case of *Pseudomonas aeruginosa*, PchA is the first enzyme in the pathway leading to production of the siderophores salicylic acid and pyochelin. An elicitor-inducible isochorismate synthase was isolated from plants and the sequence of cDNA clones from *C. roseus* and *A. thaliana* were reported (van Tegelen et al., supra and Meng et al., Plant Physiol. 118: 1536, 1999). In addition, two putative isochorismate synthases were annotated in the *Arabidopsis thaliana* genome (Accession No. AAF15941 (referred to as "At ICS1"; SEQ ID NO.: 1) and Accession No. AAF27094 (referred to as "At ICS2"; SEQ ID NO.:2). However, as is described in greater detail below, this patent provides the first proof in plants that an alternate salicylic biosynthetic pathway exists and that this alternate pathway 1) requires isochorismate synthase (specifically the inducible At ICS1) and 2) is involved in plant defense against pathogens.

Powdery Mildews as Pathogens

Powdery mildews infect numerous plant species and cause extensive crop loss (Agrios, Plant Pathology, Academic Press, San Diego, 1997). As obligate biotrophic fungal pathogens, they require specific host signals for development. Consequently, they are useful organisms for studying both host factors that facilitate disease development and host defense responses that limit disease. Three species of powdery mildew that infect *Arabidopsis* have been identified: *Erysiphe cichoracearum* (Adam et al., The Plant Journal 9:341–356, 1996), *E. cruciferarum* (Koch et al., Bot. Helv. 100:257–268, 1990), and *E. orontii* (Plotnikova et al., Mycologia 90:1009–1016, 1998).

Both compatible and incompatible interactions between Erysiphe species and *Arabidopsis* ecotypes have been characterized (Adam et al., supra; Plotnikova et al., supra; Reuber et al., supra; and Xiao et al., The Plant Journal 12:757–768, 1997). A number of ecotypes exhibit R-avr gene-mediated resistance, although in some instances the resistance conferred by a single R gene is weak and the synergistic action of multiple R genes is required for an effective resistance response (Adam et al., supra and Xiao et al., supra).

On mature *Arabidopsis* leaves, asexual conidia of *E. orontii* germinate within 1–2 hours, appressoria begin to form by 5 hours, and by 24 hours development of haustoria is initiated (Plotnikova et al., supra). When infected by *E. orontii*, *Arabidopsis* expresses the pathogenesis related genes PR-1, PR-2 (BGL2), and PR-5 (Reuber et al., supra). It has previously been shown that the induction of these PR genes occurs at least partially via a SA (salicylic acid)-dependent pathway (reviewed in Yang et al., supra). The importance of this pathway in limiting *E. orontii* growth was demonstrated by an analysis of mutant lines that also exhibit increased susceptibility to the bacterial pathogen *P. syringae* (Reuber et al., supra). Mutants characterized by SA accumulation (pad4; Glazebrook et al., 1996; Jirage et al., Proc. Natl. Acad. Sci. U.S.A. 96:13583–13588, 1999; and Zhou et al., supra) and eds5; Nawrath et al., supra; Rogers et al., supra; and Volko et al., supra.) and an SA-deficient transgenic line expressing the bacterial nahG gene (Gaffney et al., supra) are more susceptible to *E. orontii*, as is the SA-unresponsive mutant npr1(Cao et al., supra, Delaney et al., supra; and Shah et al., supra). Furthermore, analysis of PR gene expression in mutant and transgenic lines suggested that all of the PR-1 mRNA accumulation that is elicited by *E. orontii* infection occurs via SA-dependent pathway(s), whereas both SA-dependent and SA-independent pathways contribute to BGL2 and PR-5 expression (Reuber et al., supra). An additional signal transduction pathway that is instrumental in defense against some pathogens requires the signaling molecules jasmonic acid (JA) and ethylene (ET) (Staswick et al., The Plant Journal 15:747–754, 1998 and Thomma et al., Plant Physiology 121:1093–1101, 1999 and reviewed in Chang et al., Current Opinion in Plant Biology 2:352–358, 1999; Creelman et al., Annual Review of Plant Physiology and Plant Molecular Biology 48:355–381, 1997; and Wastemack et al., Trends in Plant Science 2:302–307, 1997) and leads to the production of the antimicrobial proteins defensin and thionin (Epple et al., Plant Physiology 109:813–820, 1995 and Penninckx et al., 1996). In contrast to SA-inducible PR genes, the defensin gene PDF1.2 and the thionin gene THI2.1 are not expressed in *E. orontii* infected *Arabidopsis* (Reuber et al., supra).

SUMMARY OF THE INVENTION

We have shown that isochorismate is a component of a pathway leading to the formation of salicylic acid, which is a mediator of disease resistance in plants, in *Arabidopsis*.

Accordingly, in a first aspect, the invention provides a method for conferring enhanced disease resistance on a plant or plant component to a plant pathogen. This method can further include conferring enhanced disease resistance on a plant or plant component to a fungal (e.g., powdery mildew) or a bacterial (e.g., leaf-spotting) pathogen; for example, powdery mildew caused by *Erysiphe orontii* or *Erysiphe cichoracearum* or leaf-spotting caused by a virulent or avirulent strain of *Pseudomonas syringae*. This method involves introducing into a plant cell a nucleic acid molecule encoding an isochorismate synthase (SEQ. ID. NO.: 3) to yield a transformed plant cell. A plant or a plant component can then be generated from the transformed plant cell. The nucleic acid is expressed in cells of the plant or plant component, and thereby confers enhanced disease resistance on the plant or plant component. This method can further include introducing into the plant cell a second nucleic acid molecule encoding a pyruvate lyase, a third nucleic acid molecule encoding a salicyl AMP ligase, a fourth nucleic acid molecule encoding a dihydroaeruginoic acid synthetase, and/or a fifth nucleic acid molecule encoding a pyochelin synthetase.

The invention provides an additional method for conferring enhanced disease resistance on a plant or plant component. In this method, a first nucleic acid molecule encoding a salicyl AMP ligase, a second nucleic acid molecule encoding a dihydroaeruginoic acid synthetase, and/or a third nucleic acid molecule encoding a pyochelin synthetase is introduced into a plant cell to yield a transformed plant cell. A plant or plant component is generated from the transformed plant cell, and the first, second, and/or third nucleic acid molecules are expressed in cells of the plant or plant component, thereby conferring enhanced disease resistance on the plant or plant component. This method can further involve introducing into the plant cell a nucleic acid molecule encoding an isochorismate synthase (SEQ. ID. NO.: 3) or a nucleic acid molecule encoding a pyruvate lyase.

In any of the methods described herein, the salicyl AMP ligase can be, for example, PchD, the dihydroaeruginoic acid synthetase can be, for example, PchE, and the pyochelin synthetase can be, for example, PchF. The isochorismate synthase can be *Arabidopsis thaliana* isochorismate synthase 1 (SEQ. ID. NO.: 1) or PchA (SEQ. ID. NO.: 9), and the pyruvate lyase can be PchB. Additional appropriate proteins that can be substituted for those listed above can be selected by those of skill in the art, and be obtained using, for example, the methods described below. Further, expression of any of the nucleic acid molecules described herein can be directed by a rapid response inducible promoter, as described further below.

The invention also provides a method for determining whether the success of a pathogen in infecting a plant is affected by a plant disease resistance pathway involving isochorismate synthase. This method involves contacting a mutant plant having a mutation in an inducible (i.e., inducible by pathogen infection) isochorismate synthase gene with a pathogen, and assessing the level of infection of the mutant plant with the pathogen, compared to a control plant containing a wild type inducible isochorismate synthase gene. An altered degree of pathogen infection or disease symptoms in the mutant plant, as compared to the control plant, indicates that the success of the pathogen in infecting the plant is affected by a plant disease resistance pathway involving isochorismate synthase.

Also included in the invention is a method for determining whether a pathogen induces a plant disease resistance pathway involving isochorismate synthase in a plant. This method involves contacting a mutant plant having a mutation in an inducible isochorismate synthase gene with a pathogen, and detecting the level of salicylic acid produced in the mutant plant. Detection of decreased levels of salicylic acid in the mutant plant, compared to a control plant having a wild type inducible isochorismate synthase gene, indicates that the pathogen induces a disease resistance pathway involving isochorismate synthase in the plant.

An additional method included in the invention is a method for determining whether a pathogen induces a plant disease resistance pathway involving isochorismate synthase in a plant. This method involves contacting a test plant containing a wild type inducible isochorismate synthase gene with a pathogen, and detecting the level of inducible isochorismate synthase mRNA expressed by the test plant. Detection of increased levels of inducible isochorismate synthase mRNA in the test plant, compared to a control plant not contacted with the pathogen, indicates that the pathogen induces a disease resistance pathway involving isochorismate synthase in the plant.

Another method included in the invention is a method for determining whether a pathogen induces a plant disease resistance pathway involving isochorismate synthase in a plant. This method involves contacting a test plant containing a wild type inducible isochorismate synthase gene with a pathogen, and detecting the level of inducible isochorismate synthase protein expressed by the test plant. Detection of increased levels of inducible isochorismate synthase protein in the test plant, compared to a control plant not contacted with the pathogen, indicates that the pathogen induces a disease resistance pathway involving isochorismate synthase in the plant.

In any of the four methods described above, the inducible isochorismate synthase gene can be *Arabidopsis thaliana* isochorismate synthase 1 (SEQ. ID. NO.: 3), the pathogen can be *Erysiphe orontii*, *Erysiphe cichoracearum*, or a virulent or avirulent strain of *Pseudomonas syringae* (but also see additional pathogens listed below), and the mutation can be eds16 or sid-2-2 (see below).

The invention also provides a method for identifying a gene involved in disease resistance in a plant. This method involves contacting a mutant plant (for example, a mutant *Arabidopsis thaliana* plant) having a mutation in an inducible isochorismate synthase gene (for example, At isochorismate synthase 1) with a pathogen, isolating RNA from the plant (e.g., from a pathogen-infected leaf), contacting an ordered array of nucleic acid molecules from a non-mutant plant with the RNA, and analyzing the level of binding of the RNA from the mutant plant to the array, in comparison with RNA from a control plant. Detection of a difference in binding between the mutant and control plant-derived RNAs indicates the identification of a gene involved in disease resistance in the plant. The pathogen can be, for example, *Erysiphe orontii*, *Erysiphe cichoracearum*, or a virulent or avirulent strain of *Pseudomonas syringae*. (Also see the pathogens listed below.)

The invention further provides a method for identifying a cis-acting DNA regulatory element that plays a role in disease resistance in a plant. This method involves identifying genes that are coordinately regulated by an inducible isochorismate synthase, and analyzing the promoters of the genes for shared DNA regulatory motifs. Identification of a shared DNA regulatory motif indicates the identification of a cis-acting DNA regulatory element that plays a role in disease resistance in a plant.

A related method included in the invention is for identifying a trans-acting factor that plays a role in the induction of expression of a pathogen-inducible isochorismate synthase. This method involves providing an inducible isochorismate synthase reporter construct in which the promoter of an inducible isochorismate synthase gene is operably linked to a reporter gene, and introducing the isochorismate synthase reporter construct into a mutant plant cell to screen for altered induction of the isochorismate synthase. Detection of altered induction of the expression of the reporter construct indicates the identification of a trans-acting factor that regulates inducible isochorismate synthase expression.

The invention includes a non-naturally occurring plant (e.g., an *Arabidopsis* plant) or plant component having decreased expression of an endogenous inducible isochorismate synthase, as compared with a wild type, untreated plant. The plant can include, for example, a gene that encodes a mutated form of an inducible isochorismate synthase or a mutated form of an isochorismate synthase promoter (also see below). RNA isolated from a plant having decreased expression of an endogenous inducible isochorismate synthase is also included in the invention.

Also provided in the invention is a non-naturally occurring plant or plant component including a nucleic acid molecule encoding an isochorismate synthase, operably linked to a rapid response inducible promoter that is functional in the plant or plant component. The isochorismate synthase can be, for example, *Arabidopsis thaliana* isochorismate synthase 1 (SEQ. ID. NO.: 1) or PchA (SEQ. ID. NO.: 9). The plant can also include a nucleic acid molecule encoding a pyruvate lyase, such as, for example, PchB. Further the plant can include a nucleic acid molecule encoding a salicyl AMP ligase, such as PchD, a nucleic acid molecule encoding a dihydroaeruginoic acid synthetase, such as PchE, or a nucleic acid molecule encoding a pyochelin synthetase, such as PchF.

The invention also provides a non-naturally occurring plant or plant component that includes a first nucleic acid molecule encoding a salicyl AMP ligase, such as PchD, a second nucleic acid molecule encoding a dihydroaeruginoic acid synthetase, such as PchE, and a third nucleic acid molecule encoding a pyochelin synthetase, such as PchF. The first, second, and third nucleic acid molecules are expressed in the plant or plant component.

By "gene silencing" is meant a decrease in the level of gene expression (for example, expression of a gene encoding an isochorismate synthase) by at least 30–50%, preferably by at least 50–80%, and more preferably by at least 80–95% or greater relative to the level in a control plant (for example, a wild type plant). Reduction of such expression levels can be accomplished by employing standard methods that are known in the art including, without limitation, antisense and co-suppression technologies, expression of a dominant negative gene product, or through the generation of mutated genes using standard mutagenesis techniques. Levels of isochorismate synthase polypeptide or transcript are monitored according to any standard technique including, but not limited to, northern blotting, RNase protection, or immunoblotting.

By "polypeptide" is meant any chain of amino acids, regardless of length or post-translational modification (for example, glycosylation or phosphorylation).

The term "substantially identical" is used to describe a polypeptide or nucleic acid exhibiting at least 20%, preferably 50%, more preferably 80%, and most preferably 90%, or even 95% or greater identity to a reference amino acid sequence (for example, the amino acid sequence of isochorismate synthase). For polypeptides, the length of comparison sequences will generally be at least 16 amino acids, preferably at least 20 amino acids, more preferably at least 25 amino acids, and most preferably 35 amino acids or greater. For nucleic acids molecules, the length of comparison sequences will generally be at least 50 nucleotides, preferably at least 60 nucleotides, more preferably at least 75 nucleotides, and most preferably 110 nucleotides of greater.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, FASTA, PILEUP/PRETTYBOX programs, or other publicly available sequence analysis programs. Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

A "substantially pure" isochorismate synthase polypeptide is an isochorismate synthase polypeptide that has been separated from components that naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, an isochorismate synthase polypeptide. A substantially pure isochorismate synthase polypeptide can be obtained, for example, by extraction from a natural source (for example, a plant cell); by expression of a recombinant nucleic acid encoding an isochorismate synthase, or by chemically synthesizing the protein. Purity can be measured by any appropriate method, for example, column chromatography, polyacrylamide gel electrophoresis, or by HPLC analysis.

By "isolated DNA" is meant DNA that is free of the genes which, in the naturally-occurring genome of the organism from which the DNA of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. It also includes a recombinant DNA that is part of a hybrid gene encoding additional polypeptide sequence.

By "derived from" is meant isolated from or having the sequence of a naturally-occurring sequence (for example, a cDNA, genomic DNA, synthetic DNA, or combination thereof).

By "specifically hybridizes" is meant that a nucleic acid sequence is capable of hybridizing to a DNA sequence at least under low stringency conditions as described herein, and preferably under high stringency conditions, also as described herein. These conditions are well known in the art and may be altered in order to identify or detect identical or related polynucleotide sequences.

By "transformed cell" is meant a cell into which (or into an ancestor of which) has been introduced, by means of recombinant DNA techniques, a DNA molecule, for example, a DNA molecule encoding an isochorismate synthase.

By "positioned for expression" is meant that the DNA molecule is positioned adjacent to a DNA sequence which directs transcription (i.e., facilitates the production of an RNA molecule) and, if a protein product is desired, translation of the sequence (i.e., facilitates the production of, for example, an isochorismate synthase or a recombinant protein).

By "reporter gene" is meant a gene whose expression may be assayed; such genes include, without limitation, β-glucuronidase (GUS), luciferase, chloramphenicol acetyl transferase (CAT), green fluorescent protein (GFP), β-galactosidase, herbicide resistant genes, and antibiotic resistance genes.

By "expression control region" is meant any minimal sequence sufficient to direct transcription. Included in the invention are promoter elements that are sufficient to render promoter-dependent gene expression controllable for cell-, tissue-, or organ-specific gene expression, or elements that are inducible by external signals or agents (for example, light-, pathogen-, wound-, stress-, or hormone-inducible elements or chemical inducers such as SA or INA); such elements may be located in the 5' or 3' regions of the native gene or engineered into a transgene construct.

A gene and a regulatory sequence(s) said to be "operably linked" if they are connected in such a way as to permit gene expression when the appropriate molecules (for example, transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

By "plant component" is meant a part, segment, or organ obtained from an intact plant or plant cell. Exemplary plant components include, without limitation, somatic embryos, leaves, stems, roots, flowers, tendrils, fruits, scions, and rootstocks.

By "crucifer" is meant any plant that is classified within the Cruciferae family. The Cruciferae include many agricultural crops, including, without limitation, rape (for example, *Brassica campestris* and *Brassica napus*), broccoli, cabbage, brussel sprouts, radish, kale, Chinese kale, kohlrabi, cauliflower, turnip, rutabaga, mustard, horseradish, and *Arabidopsis*.

By "transgene" is meant any piece of DNA that is inserted by artifice into a cell, and becomes part of the genome of the organism that develops from that cell. Such a transgene may include a gene that is partly or entirely heterologous (i.e., foreign) to the transgenic organism, or may represent a gene having sequence identity to an endogenous gene of the organism.

By "transgenic" is meant any cell that includes a DNA sequence that is inserted by artifice into a cell and becomes part of the genome of the organism that develops from that cell. As used herein, the transgenic organisms are generally transgenic plants and the DNA (for example, a transgene) is inserted by artifice into the nuclear or plastidic genome. A transgenic plant according to the invention may contain one or more of the nucleic acid molecules described herein By "pathogen" is meant an organism whose infection of viable plant tissue elicits a disease response in the plant tissue. Such pathogens include, without limitation, bacteria, mycoplasmas, fungi, oomycetes, insects, nematodes, viruses, and viroids. Examples of such plant diseases caused by these pathogens are described in Chapters 11–16 of Agrios, *Plant Pathology*, 3$^{rd}$ ed., Academic Press, Inc., New York, 1988.

Examples of bacterial pathogens include, without limitation, *Erwinia* (for example, *E. carotovora*), *Pseudomonas* (for example, *P. syringae*), and *Xanthomonas* (for example, *X. campepestris*, and *X. oryzae*).

Examples of fungal or fungal-like disease-causing pathogens include, without limitation, *Alternaria* (for example, *A. brassicola* and *A. solani*), *Ascochyta* (for example, *A. pisi*), *Botrytis* (for example, *B. cinerea*), *Cercospora* (for example, *C. kikuchii* and *C. zaea-maydis*), *Colletotrichum* sp. (for example, *C. lindemuthianum*), *Diplodia* (for example, *D. maydis*), *Erysiphe* (for example, *E. orontii*, *E. graminis* f.sp. *graminis*, and *E. graminis* f.sp. *hordei*), *Fusarium* (for example, *F. nivale* and *F. oxysporum*, *F. graminearum*, *F. solani*, *F. moniliforme*, and *F. roseum*), *Gaeumanomyces* (for example, *G. graminis* f.sp. *tritici*), *Helminthosporium* (for example, *H. turcicum*, *H. carbonum*, and *H. maydis*), *Macrophomina* (for example, *M. phaseolina* and *Maganaporthe grisea*), *Nectria* (for example, *N. heamatocacca*), *Peronospora* (for example, *P. manshurica*, *P. tabacina*), *Phoma* (for example, *P. betae*), *Phymatotrichum* (for example, *P. omnivorum*), *Phytophthora* (for example, *P. cinnamomi*, *P. cactorum*, *P. phaseoli*, *P. parasitica*, *P. citrophthora*, *P. megasperma* f.sp. *sojae*, and *P. infestans*), *Plasmopara* (for example, *P. viticola*), *Podosphaera* (for example, *P. leucotricha*), *Puccinia* (for example, *P. sorghi*, *P. striiformis*, *P. graminis* f.sp. *tritici*, *P. asparagi*, *P. recondita*, and *P. arachidis*), *Puthium* (for example, *P. aphanidermatum*), *Pyrenophora* (for example, *P. tritici-repentens*), *Pyricularia* (for example, *P. oryzea*), *Pythium* (for example, *P. ultimum*), *Rhizoctonia* (for example, *R. solani* and *R. cerealis*), *Scerotium* (for example, *S. rolfsii*), *Sclerotinia* (for example, *S. sclerotiorum*), *Septoria* (for example, *S. lycopersici*, *S. glycines*, *S. nodorum* and *S. tritici*), *Thielaviopsis* (for example, *T. basicola*), *Uncinula* (for example, *U. necator*), *Venturia* (for example, *V. inaequalis*), and *Verticillium* (for example, *V. dahliae* and *V. albo-atrum*).

Examples of pathogenic nematodes include, without limitation, root-knot nematodes (for example, *Meloidogyne* sp., such as *M. incognita*, *M. arenaria*, *M. chitwoodi*, *M. hapla*, *M. javanica*, *M. graminocola*, *M. microtyla*, *M. graminis*, and *M. naasi*), cyst nematodes (for example, *Heterodera* sp., such as *H. schachtii*, *H. glycines*, *H. sacchari*, *H. oryzae*, *H. avenae*, *H. cajani*, *H. elachista*, *H. goettingiana*, *H. graminis*, *H. mediterranea*, *H. mothi*, *H. sorghi*, and *H. zeae*, or, for example, *Globodera* sp., such as *G. rostochiensis* and *G. pallida*), root-attacking nematodes (for example, *Rotylenchulus reniformis*, *Tylenchuylus semipenetrans*, *Pratylenchus brachyurus*, *Radopholus citrophilus*, *Radopholus similis*, *Xiphinema americanum*, *Xiphinema rivesi*, *Paratrichodorus minor*, *Heterorhabditis heliothidis*, and *Bursaphelenchus xylophilus*), and above-ground nematodes (for example, *Anguina funesta*, *Anguina tritici*, *Ditylenchus dipsaci*, *Ditylenchus myceliphagus*, and *Aphenlenchoides besseyi*).

Examples of viral pathogens include, without limitation, tobacco mosaic virus (TMV), tobacco necrosis virus (TNV), potato leaf roll virus, potato virus X, potato virus Y, tomato spotted wilt virus, and tomato ring spot virus.

By "enhanced disease resistance" is meant a level of resistance to a disease-causing pathogen in a non-naturally occurring plant (or cell or seed thereof) that is greater than the level of resistance in a control plant (for example, a non-transgenic plant or a wild type plant). In preferred embodiments, the level of resistance in a non-naturally occurring transgenic plant of the invention is at least 5% to 20% (and preferably 30% or 40%) greater than the resistance exhibited by a control plant. In other preferred embodiments, the level of resistance to a disease-causing pathogen is 50% greater, 60% greater, and more preferably even 75% or 90% greater than a control plant; with up to 100% or greater above the level of resistance as compared to a control plant being most preferred. The level of resistance is measured using conventional methods. For example, the level of resistance to a pathogen may be determined by comparing physical features and characteristics (for example, plant height and weight) or by comparing disease symptoms (for example, delayed lesion development, reduced lesion size, leaf wilting and curling, water-soaked spots, amount of pathogen growth, and discoloration of cells) of the non-naturally occurring plant (e.g., a transgenic plant).

By "detectably-labeled" is meant any direct or indirect means for marking and identifying the presence of a molecule, for example, an oligonucleotide probe or primer, a gene or fragment thereof, or a cDNA molecule or a fragment thereof. Methods for detectably-labeling a molecule are well known in the art and include, without limitation, radioactive labeling (for example, with an isotope such as $^{32}P$ or $^{35}S$) and nonradioactive labeling (for example, fluorescence of chemiluminescent labeling, for example, fluorescein labeling).

The invention provides a number of important advances and advantages for the protection of plants against pathogens. For example, by increasing the expression of isochorismate synthase (and other ICS-derived SA pathway members or associated proteins) in a plant, the invention facilitates an effective and economical means for in-plant protection against plant pathogens. Such protection against pathogens reduces or minimizes the need for traditional chemical practices (for example, application of fungicides, bactericides, nematicides, insecticides, or viricides) that are typically used by farmers for controlling the spread of plant pathogens and providing protection against disease-causing pathogens. In addition, because plants having increased expression of isochorismate synthase are less vulnerable to pathogens and their diseases, the invention further provides for increased production efficiency, as well as for improvements in quality and yield of crop plants and ornamentals. Thus, the invention contributes to the production of high quality and high yield agricultural products, for example, fruits, ornamentals, vegetables, cereals, and field crops having reduced spots, blemishes, and blotches that are caused by pathogens; agricultural products with increased shelf-life and reduced handling costs; and high quality and yield crops for agricultural (for example, cereal and field crops), industrial (for example, oilseeds), and commercial (for example, fiber crops) purposes. Furthermore, because the invention reduces the necessity for chemical protection against plant pathogens, the invention benefits the environment where the crops are grown. Genetically-improved seeds and other plant products that are produced using plants expressing the genes described herein also render farming possible in areas previously unsuitable for agricultural production.

Other features and advantages of the invention will be apparent from the following detailed description, the drawings, and the claims.

BRIEF DESCRIPTION OF THE DRAWINGS

FIG. 11B shows an alignment of the At ICS chorismate-binding domain (PromDom #PD000779; SEQ ID NO: 7) with selected disochorismate synthases (SEQ ID NOS: 17–21). Identical residues are in black and conserved residues (within 3 distance units, PAM250 matrix) are shaded. Asterisks indicate residues deemed critical for ICS activity. The arrow locates position of the EMS-generated mutation sid2-1 in which Q (CAA) is converted to a stop codon (TAA), and the altered region of the fast neutron mutant sid2-2 is underlined.

FIG. 12 is an alignment of plant and bacterial isochorismate synthases (SEQ ID NOS: 1, 2, 9, 10, and 22) and shows the location of the point mutation in sid2-1.

FIG. 16B are charts that show the relative SA (free and sugar conjugated SA) levels and ICS1 and PR1 gene expression levels in mutant or transgenic *Arabidopsis* compared to wild type plants. ICS1 and PR1 gene expression was accessed by Northern blot analysis of total RNA from leaves infected with Erysiphe. Relative values are indicated as <0.1×(−−), 0.5×(−), wild type (w.t.), >2×(+), and >10×(++) compared to wild type.

DETAILED DESCRIPTION

Figure 1:
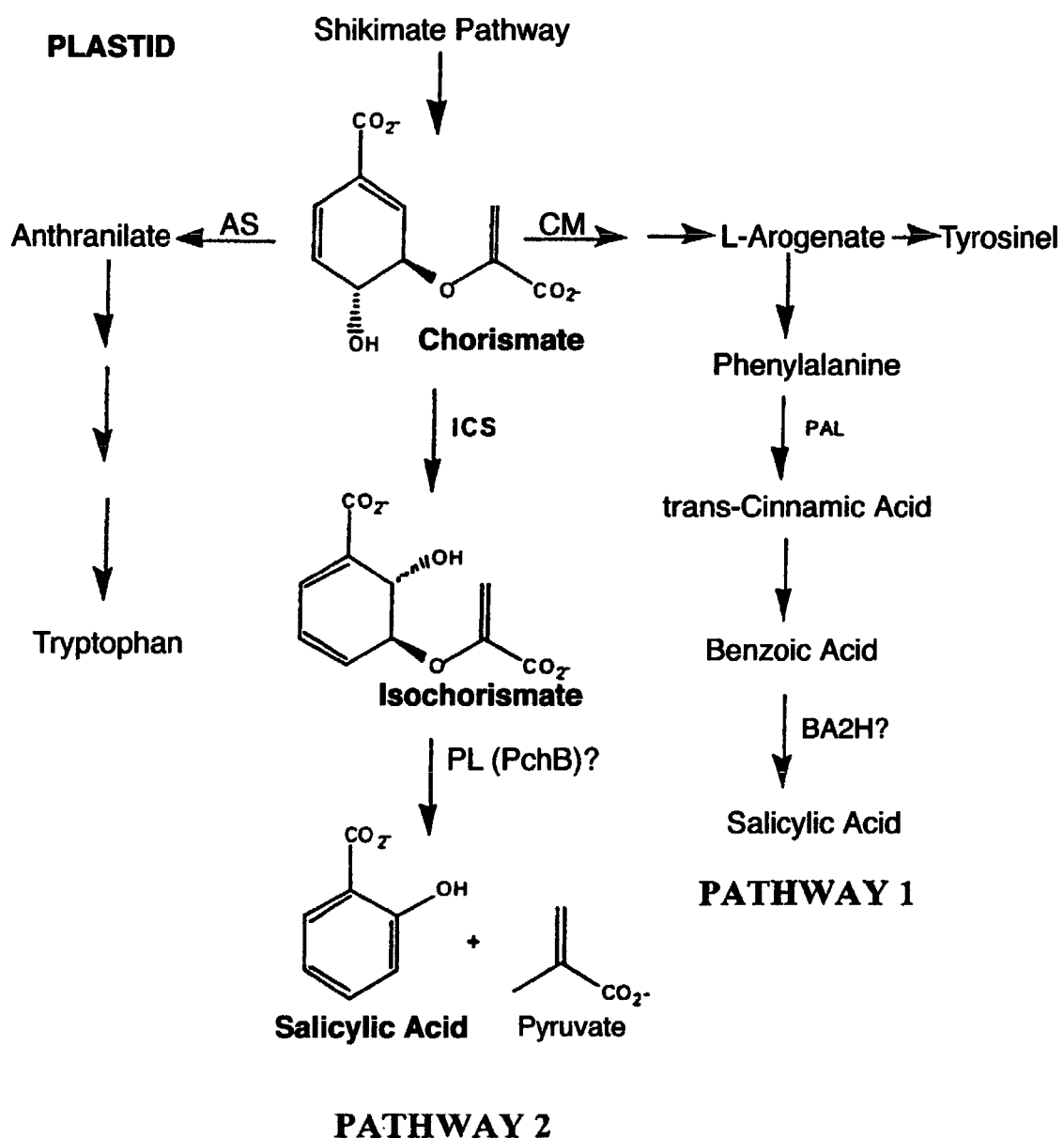
FIG. 1 is a schematic representation of salicylic acid biosynthetic pathways.

We have identified a novel pathway that leads to the production of salicylic acid in *Arabidopsis*. In particular, we have identified an *Arabidopsis* eds16-1/sid2-2, which is characterized by decreased levels of salicylic acid. Our analysis of this mutant revealed that it is characterized by a mutation in a gene encoding isochorismate synthase (ICS), which converts chorismate to isochorismate, and, more specifically, that the mutation is in the *Arabidopsis thaliana* isochorismate synthase 1 (At ICS1) gene (SEQ. ID. NO.: 3). In addition, we determined that the sid2-1 mutant (Nawrath et al., supra) also contains a mutation in this isochorismate synthase gene. Thus, we have determined that isochorismate is a component of a pathway leading to the production of salicylic acid in *Arabidopsis*. As noted above, salicylic acid plays an important role in disease resistance in plants. Thus, the invention provides novel methods and plants that can be used in the development of approaches for inducing or increasing disease resistance in plants. Examples of these approaches are described as follows.

The invention provides methods of conferring enhanced disease resistance on a plant or plant component to pathogens. For example, enhanced disease resistance to powdery mildew (e.g., *Erysiphe orontii* or *Erysiphe cichoracearum*) or a leaf-spotting bacterial pathogen (e.g., a virulent or avirulent form of *Pseudomonas syringae*) can be conferred on a plant by introducing into a plant cell a nucleic acid molecule encoding an isochorismate synthase (e.g., ICS1; SEQ. ID. NO.: 1 or PchA; SEQ. ID. NO.: 9). Additionally, enhanced disease resistance can be conferred on a plant by introducing into a plant cell a nucleic acid molecule encoding an isochorismate synthase gene and a nucleic acid molecule encoding a pyruvate lyase gene (e.g., PchB).

For example, enhanced disease resistance to powdery mildew (e.g., *Erysiphe orontii* or *Erysiphe cichoracearum*) or a leaf-spotting bacterial pathogen (e.g., a virulent or avirulent form of *Pseudomonas syringae*) can be conferred on a plant by introducing into a plant cell a nucleic acid molecule encoding an isochorismate synthase (e.g., ICS1; SEQ. ID. NO.: 1 or PchA; SEQ. ID. NO.: 9) and a nucleic acid molecule encoding a pyruvate lyase (e.g., PchB). As described further below, a plant or plant component can be generated from such a plant cell. Additional genes involved in siderophore production (see below) can also be introduced into such a plant. For example, nucleic acid molecules encoding a salicyl AMP ligase (e.g., PchD), a dihydroaeruginoic acid synthetase (e.g., PchE), or a pyochelin synthetase (e.g., PchF) can be introduced into the plant cell, alone or in combination.

Also included in the invention is a method of conferring disease resistance on a plant or plant component by introducing a nucleic acid molecule encoding encoding a salicyl AMP ligase (e.g., PchD), a dihydroaeruginoic acid synthetase (e.g., PchE), or a pyochelin synthetase (e.g., PchF) into a plant cell, and then growing a plant or plant component from the cell. Optionally, a nucleic acid molecule encoding an isochorismate synthase (e.g., ICS1; SEQ. ID. NO.: 1 or PchA; SEQ. ID. NO.: 9) or a nucleic acid molecule encoding a pyruvate lyase (e.g., PchB) can be introduced into such a plant cell, alone or in combination.

The invention also provides methods in which plants having a mutation in an isochorismate synthase gene are used to determine whether a particular pathogen induces the isochorismate pathway of salicylic acid production in an infected plant. In one example of this method, a plant having a mutant isochorismate synthase gene is contacted with a pathogen, and the level of salicylic acid produced in the mutant plant is analyzed. Detection of decreased levels of salicylic acid in the mutant plant, compared to a control plant, having a wild type isochorismate synthase gene, indicates that the pathogen induces a disease resistance pathway involving isochorismate synthase in the plant. In a variation of this method, the level of infection of the plant by the pathogen is determined. In a related method, the level of isochorismate synthase mRNA or protein is compared between a wild type plant that has been contacted with a pathogen and a wild type plant that has not been contacted with the pathogen.

If a pathogen is identified as inducing the ICS pathway of salicylic acid production, plants that are infected by the pathogen, or plants that are at risk of being infected by the pathogen, can be treated so as to increase their resistance to the pathogen. As is discussed further below, this can be accomplished by, for example, introduction of a gene encoding isochorismate synthase into the plant. This can also be accomplished by introduction of a gene that is involved in the ICS pathway (e.g., a gene downstream from ICS in this pathway; see below) into a plant. Alternatively, a gene encoding a transcription factor that induces expression of the isochorismate synthase gene of the plant can be introduced into the plant (see below). These genes can be introduced into plants alone or in combination.

Another example of a method in which plants having a mutation in an isochorismate synthase gene can be used involves the identification of additional genes that play a role in disease resistance in plants. This method can involve, for example, screening RNA populations obtained from such mutant plants to identify other genes having altered (e.g., decreased) expression in the mutant plants in response to pathogen infection. As is discussed further below, a preferable format in which the screening takes place involves the use of a microchip that includes an ordered array of the genome of the plant. Genes that are identified as playing a role in disease resistance using this method can be used, for example, to impart disease resistance to, or to increase disease of, a plant. This can be accomplished by introducing the gene into the plant or, alternatively, by introducing a gene encoding a transcription factor that controls expression of the novel disease resistance gene into a plant.

Another approach to increasing or inducing disease resistance in plants that is included in the invention relates to pathways involved in siderophore production. Siderophores are compounds that bind iron. Iron is required by many pathogens to effectively infect plants. Thus, compounds that chelate iron, such as siderophores, may play a role in plant defense mechanisms. The invention thus provides a method of increasing or inducing disease resistance in a plant by introducing a gene involved in siderophore production into the plant. Examples of genes that can be used in this method include pchA, pchB, pchC, pchD, pchE, and pchF, which have been identified as playing a role in the production of the siderophore pyochelin in *Pseudomonas aeruginosa*. Genes that are involved in siderophore production in other plants can be identified, for example, using the methods described below, and such genes can be used in this method. Alternatively, transcription factors that are identified, as is described below, as inducing expression of genes that are involved in siderophore production can be used in this method.

The methods described above can be conducted using the following methods.

Engineering Plants Having Decreased Expression of Isochorismate Synthase

Plants having decreased expression of ICS can be used in the screening methods described above, and can be generated according to standard gene silencing methods including, without limitation, co-suppression and antisense methodologies, expression of dominant negative gene products, and creation of plants having mutated genes encoding an isochorismate synthase. eds16 (see below) and sid2 (Nawrath et al., supra) are examples of *Arabidopsis* mutants that can be used in the invention (also see FIG. 10).

Co-Suppression

One preferred method of silencing gene expression is co-suppression, which is also referred to as "sense suppression." This technique, which involves introduction of a nucleic acid molecule that is configured in the sense orientation, has been shown to effectively block the transcription of target genes (see, for example, Napoli et al., Plant Cell 2:279–289, 1990; Jorgensen et al., U.S. Pat. No. 5,034,323).

Generally, sense suppression involves transcription of an introduced sequence. However, co-suppression can also occur when the introduced sequence contains no coding sequence per se, but only intron or untranslated sequences homologous to sequences present in the primary transcript of the endogenous gene to be repressed. The introduced sequence generally will be substantially identical to the endogenous gene targeted for repression. Such identity is typically greater than about 50%, but higher identities (for example, 80% or even 95%) are preferred, because they can result in more effective repression. The effect of co-suppression can also be applied to other proteins within a similar family of genes exhibiting homology or substantial homology. Segments from a gene from one plant can be used directly, for example, to inhibit expression of homologous genes in different plant species.

In sense suppression, the introduced sequence, requiring less than absolute identity, need not be full length, relative to either the primary transcription product or to fully processed mRNA. A higher identity in a shorter than full-length sequence can compensate for a longer sequence having less identity. Furthermore, the introduced sequence does not need to have the same intron or exon pattern, and identity of non-coding segments can be equally effective. Sequences of at least 50 base pairs are preferred, with introduced sequences of greater length being more preferred (see, for example, the methods described by Jorgensen et al., supra.)

Antisense Suppression

In antisense technology, a nucleic acid molecule segment from a desired plant gene is cloned and operably linked to an expression control region, such that an antisense strand of RNA is synthesized. The construct is then transformed into a plant in which the antisense strand of RNA is produced. In plant cells, it has been shown that antisense RNA can inhibit gene expression.

The nucleic acid segment to be introduced in antisense suppression is generally substantially identical to at least a portion of the endogenous gene or genes to be repressed, but need not be identical. Vectors that can be used in the present invention thus can be designed such that the inhibitory effect applies to other proteins within a family of genes exhibiting homology or substantial homology to the target gene. Segments from a gene from one plant can be used, for example, directly to inhibit expression of homologous genes in different plant species.

The introduced sequence also need not be full length relative to either the primary transcription product or to fully processed mRNA. Generally, higher homology can be used to compensate for the use of a shorter sequence. Moreover, the introduced sequence does not need to have the same intron or exon pattern, and homology of non-coding segments will be equally effective. In general, such an antisense sequence will usually be at least 15 base pairs, preferably about 15–200 base pairs, and more preferably 200–2,000 base pairs in length or greater. The antisense sequence can be complementary to all or a portion of the gene to be suppressed (for example, ICS), and, as will be appreciated by those of skill in the art, the particular site or sites to which the antisense sequence binds, as well as the length of the antisense sequence, can vary, depending upon the degree of inhibition desired and the uniqueness of the antisense sequence. A transcriptional construct expressing an isochorismate synthase antisense nucleotide sequence can include, in the direction of transcription, a promoter, the sequence coding for the antisense RNA on the sense strand, and a transcriptional termination region. Antisense sequences can be constructed and expressed as described, for example, by van der Krol et al. (Gene 72:45–50, 1988); Rodermel et al. (Cell 55:673–681, 1988); Mol et al. (FEBS Lett. 268: 427–430, 1990); Weigel et al. (Nature 377:495–500, 1995); Cheung et al., (Cell 82:383–393, 1995); and Shewmaker et al. (U.S. Pat. No. 5,107,065).

Dominant Negatives

Dominant negative transgenes are constructed according to methods known in the art. Typically, a dominant negative gene encodes a mutant isochorismate synthase, which, when overexpressed, disrupts the activity of the wild type polypeptide. Transgenic plants expressing a transgene encoding a dominant negative gene product of an isochorismate synthase are assayed in artificial environments or in the field to demonstrate that the transgene confers disease resistance on the transgenic plant.

Mutants

Plants having decreased expression of an isochorismate synthase gene can also be generated using standard mutagenesis methodologies. Such mutagenesis methods include, without limitation, treatment of seeds with ethyl methylsulfate or fast neutron irradiation, as well as T-DNA insertion methodologies. Expression of an isochorismate synthase gene and disease resistance phenotypes in mutated and non-mutated lines are evaluated according to standard procedures (for example, those described herein). When compared to non-mutated plants, mutated plants having decreased expression of a gene encoding an isochorimsate synthase exhibit decreased disease resistance.

Microarray Gene Expression Monitoring and Discovery of Additional Disease Resistance Genes As mentioned above, the plants, plant components, plant cells, and methods described herein can be used in conjunction with standard microarray technologies (for example, cDNA microarrays or DNA chips) for monitoring the expression of genes controlled by, or associated with, isochorismate synthase activity. In particular, microarray expression monitoring provides a basis for identifying genes that involved in plant defense mechanisms associated with isochorismate synthase gene expression. For example, target genes that regulate or are regulated by isochorismate synthase can be identified by correlating changes in gene expression with specific changes in cells having either reduced or increased levels of isochorismate synthase. Genes exhibiting altered expression levels in such cells are identified, and subsequently serve as specific targets whose expression is modified (e.g., increased) to generate transgenic plants having increased resistance to a pathogen.

In general, microarray technology utilizes organized DNA libraries of interest (for example, a cDNA library), the members of which are arrayed on a solid support (e.g., a glass slide). Such cDNAs are amplified by polymerase chain reaction, purified, and small quantities are deposited onto known locations of a microchip using standard methods, such as high-speed robotics. Microarrays of cDNAs thus provide expression information for each gene represented on the microchip. Arrayed sequences, in turn, serve as targets for hybridization to cDNA probes prepared from RNA samples of plant cells or tissues of interest (e.g., cells or tissue from a plant mutant for ICS). Multi-color fluorescence labeling of cDNA probes further provides a means facilitating comparative differential expression analysis of a variety of plant tissues under different physiological and environmental conditions. Typically, a gene having expression that is increased or decreased in an appropriate genetic background is considered as a useful target involved in plant disease resistance.

Exemplary microarray methods for differential and quantitative monitoring of gene expression and for identifying novel genes are provided in Schena et al. (Science 270: 467–470, 1995), Schena et al. (Proc. Natl. Acad. Sci. U.S.A. 93:10614–10619, 1996), Heuller et al. (Proc. Natl. Acad. Sci. U.S.A. 94:2150–2155, 1997), and Case-Green et al. (Curr. Opin. Chem. Biol. 2:404–410, 1998). Also see Cho et al., Nature Genetics 23:203–207, 1999.

In one particular example, microarrays can be used to examine gene expression in plant tissue (e.g., a leaf or root) having reduced levels of isochorismate synthase. For example, plants having a mutation in an isochorismate synthase gene (e.g., eds16 or sid2), plants expressing a dominant-negative isochorismate synthase gene, or plants that express antisense isochorismate synthase RNA can be used. Total mRNA from leaves of pathogen-exposed wild type (control) and ICS mutant plants is fluorescently labeled using a single round of reverse transcriptase. Fluorescently labeled mRNA is then hybridized to a microarray containing target DNA, such as expressed sequence tags from a plant cDNA library. The array is washed under high stringency conditions and scanned with a confocal laser scanning device to detect hybridization via emission of the fluorescently labeled DNA. Comparative expression of control and test plants is then analyzed, and array elements displaying altered fluorescence ratios are selected for further analysis. For example, genes that are highly induced in the test plants, as compared to wild type plants, are selected and characterized by sequencing. Such genes can then be used to engineer disease resistant plants.

Alternatively, microarrays can be used to examine gene expression in plant tissue having increased levels of an isochorismate synthase gene. In such plants, salicylic acid production is increased, increasing pathogen resistance. Accordingly, these plants provide a means for identifying novel target genes that regulate isochorismate synthase.

Identification of Transcription Factors Involved in Controlling Expression of Isochorismate Synthase Transcription factors involved in controlling the expression of At ICS1 can be identified using any of a number of well-known techniques. For example, the At ICS1 promoter can be analyzed for known cis-acting elements by using, for example, a publicly available program and database, such as PLACE, A Database of Plant Cis-acting Regulatory DNA Elements. Alternatively, mutation analysis of the At ICS1 promoter can be carried out to define cis-acting elements necessary for induction, and such elements can be assessed using an At ICS1 mutated promoter-reporter construct.

Once a putative cis-acting regulatory element is identified, the cognate trans-acting factor can be identified by numerous methods, including binding assays, in which the ability of a given transcription factor to bind to the At ICS1 cis-acting element is ascertained. An alternative approach is to utilize an At ICS1 reporter construct in which the At ICS1 reporter is linked to a gene such as green fluorescent protein (GPF), which is easily detected, to screen for mutants that have altered expression of At ICS1. In *Arabidopsis*, pathogen-induced tryptophan biosynthesis was found to be regulated by the expression of ASA1. A transcription factor (ATR1) responsible for the activation of this pathway was found by screening for mutants with deregulated ASA1 expression (Bender et al., Proc. Natl. Acad. Sci. U.S.A. 95:5655–5660, 1998; and Niyogi et al., Plant Cell 4:721–733, 1992).

Isolation of Other Genes Encoding Isochorismate Synthase

Figure 10:
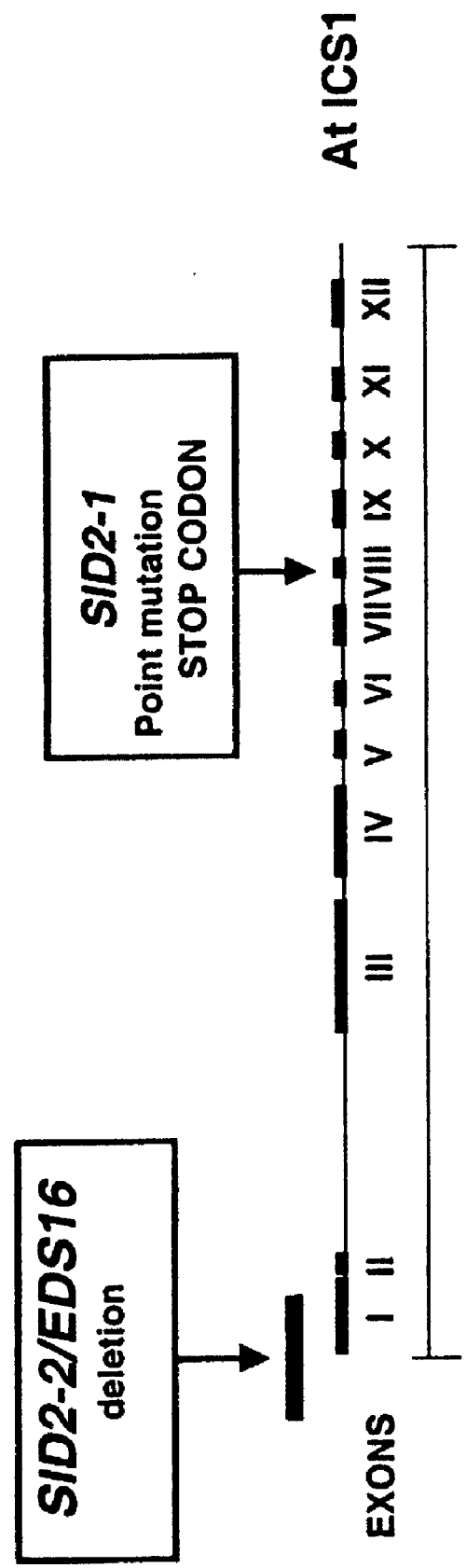
FIG. 10 is a schematic representation of the At ICS1 gene that shows that eds16-1/sid2-2 and sid2-1 are null mutants in At ICS1, as well as the positions of the mutations in these mutants. In particular, sid2-1 contains a point mutation of C (wild type) to T (sid2-1) resulting in a change from CAA encoding the amino acid Gln (Q) to TAA encoding a STOP codon. This alteration occurs in residue 387 of exon 8, as depicted in FIG. 12. The truncated product produced because of this early STOP codon is not expected to be active, based on conservation of the remaining exons in bacterial and plant isochorismate synthases.

As noted above, according to the invention, a plant that is infected, or is at risk of being infected, by a particular pathogen can be made resistant to the pathogen by introduction of an ICS gene into the plant. For example, an *Arabidopsis* ICS gene (see, e.g., GenBank Accession No. AF078080; Meng et al., supra; FIG. 10; and SEQ. ID. NO.: 5) can be introduced into the plant. The following methods can be used to isolate genes encoding ICS from other sources. Also, these methods can be used to isolate other genes that are useful in the invention, including genes that encode other members of the ICS pathway, genes that are involved in siderophore production, and genes encoding transcription factors that are involved in controlling expression of genes in the ICS or siderophore production pathways (see above).

Any plant cell can serve as the nucleic acid molecule source for the molecular cloning of a gene encoding an isochorismate synthase. Isolation of such a gene can be accomplished using conventional screening methods, involving use of nucleic acid hybridization screening. Such hybridization techniques and screening procedures are well known to those skilled in the art, and are described, for example, in Benton et al., Science 196:180–182, 1977; Grunstein et al., Proc. Natl. Acad. Sci. U.S.A. 72:3961–3695, 1975; Ausubel et al., 1999, *Current Protocols in Molecular Biology*, Wiley Interscience, New York; Berger et al., *Guide to Molecular Cloning Techniques*, 1987, Academic Press, New York; and Sambrook et al., *Molecular Cloning: A Laboratory Manual*, Cold Spring Harbor Laboratory Press, New York.

In one particular example, all or part of a known isochorismate synthase cDNA can be used as a probe to screen a recombinant plant or bacterial DNA library. Hybridizing sequences are detected by plaque or colony hybridization, according to the methods described below. Alternatively, using all or a portion of the amino acid sequence of an isochorismate synthase, one can readily design specific oligonucleotide probes, including degenerate oligonucleotide probes (i.e., a mixture of all possible coding sequences for a given amino acid sequence). The sequence of these oligonucleotides can be based upon the sequence of either DNA strand and any appropriate portion of the isochorismate synthase polypeptide gene sequence. General methods for designing and preparing such probes are provided, for example, in Ausubel et al. (supra) and Berger et al. (supra). These oligonucleotides are useful for gene isolation, either through their use as probes capable of hybridizing to complementary sequences or as primers for various amplification techniques, for example, polymerase chain reaction (PCR) cloning strategies. If desired, a combination of different oligonucleotide probes can be used for the screening of a recombinant DNA library. The oligonucleotides can be detectably-labeled using methods known in the art and used to probe filter replicas from a recombinant DNA library. Recombinant DNA libraries are prepared according to methods that are well known in the art, for example, as described in Ausubel et al. (supra), or they may be obtained from commercial sources.

In one particular example of this approach, gene sequences having greater than 80% identity to isochorismate synthase gene of *Arabidopsis*, as described herein, are detected or isolated using high stringency conditions. High stringency conditions can include hybridization at about 42° C. and in about 50% formamide, 0.1 mg/ml sheared salmon sperm DNA, 1% SDS, 2×SSC, and 10% Dextran sulfate, a first wash at about 65° C., in about 2×SSC and 1% SDS, followed by a second wash at about 65° C. and in about 0.1×SSC. Alternatively, high stringency conditions can include hybridization at about 42° C. and about 50% formamide, 0.1 mg/ml sheared salmon sperm DNA, 0.5% SDS, 5×SSPE, and 1× Denhardt's, followed by two washes at room temperature in 2×SSC, 0.1% SDS, and two washes at between 55–60° C. in 0.2×SSC, 0.1% SDS.

In another approach, low stringency hybridization conditions for detecting isochorismate synthase genes having about 30% or greater sequence identity to the *Arabidopsis* isochorismate synthase gene described herein include, for example, hybridization at about 42° C. in 0.1 mg/ml sheared salmon sperm DNA, 1% SDS, 2×SSC, and 10% Dextran sulfate (in the absence of formamide), and a wash at about 37° C. in 6×SSC, about 1% SDS. Alternatively, the low stringency hybridization can be carried out at about 42° C.

in 40% formamide, 0.1 mg/ml sheared salmon sperm DNA, 0.5% SDS, 5×SSPE, and 1× Denhardt's, followed by two washes at room temperature in 2×SSC, 0.1% SDS, and two washes at room temperature in 0.5×SSC, 0.1% SDS. These stringency conditions are exemplary; other appropriate conditions can be determined by those skilled in the art.

As discussed above, oligonucleotides can also be used as primers in amplification cloning strategies, for example, using PCR. PCR methods are well known in the art and are described, for example, in Innis et al. *PCR Technology*, Erlich, ed., Stockton Press, London, 1989; *PCR Protocols: A Guide to Methods and Applications*, Innis et al., eds., Academic Press, Inc., New York, 1990; and Ausubel et al. (supra). Primers encoding specific structural features of an isochorismate synthase gene are useful for isolating genes having similar structural domains. Primers are optionally designed to allow cloning of the amplified product into a suitable vector, for example, by including appropriate restriction sites at the 5' and 3' ends of the amplified fragment, as described herein. If desired, isochorismate synthase gene sequences can be isolated using the PCR "RACE" technique, or Rapid Amplification of cDNA Ends (see, for example, Innis et al., supra). By this method, oligonucleotide primers based on an isochorismate synthase gene sequence are oriented in the 3' and 5' directions and are used to generate overlapping PCR fragments. These overlapping 3'- and 5'-end RACE products are combined to produce an intact full-length cDNA. This method is described in Innis et al. (supra) and Frohman et al., Proc. Natl. Acad. Sci. U.S.A. 85:8998–9002, 1988.

Alternatively, any plant cDNA or cDNA expression library can be screened by functional complementation of a plant having a mutation in a gene encoding an isochorismate synthase according to standard methods that are described herein.

Confirmation of the relatedness of a sequence to the isochorismate synthase gene family can be accomplished by a variety of conventional methods including, but not limited to, functional complementation assays and sequence comparison of the gene and its expressed product. In addition, the activity of the gene product can be evaluated according to any of the techniques described herein, for example, the functional or immunological properties of its encoded product.

In addition, the isochorismate synthase sequence disclosed herein provides a basis for searching databases such as Genbank to identify homologs. Once a gene encoding an isochorismate synthase is identified, it is cloned according to standard methods, and can be used for the construction of plant expression vectors as described below.

Polypeptide Expression

Those skilled in the field of molecular biology will understand that any of a wide variety of expression systems can be used to express isochorismate synthase genes of the invention. The polypeptide can be produced, for example, in any of a number of plant cells or whole plants including, without limitation, algae, tree species, ornamental species, temperate fruit species, tropical fruit species, vegetable species, legume species, crucifer species, monocots, dicots, or in any plant of commercial or agricultural significance. Particular examples of suitable plant hosts include, but are not limited to, conifers, petunia, tomato, potato, pepper, tobacco, *Arabidopsis*, lettuce, sunflower, oilseed rape, flax, cotton, grape, citrus, sugarbeet, celery, soybean, alfalfa, Medicago, lotus, Vigna, cucumber, carrot, eggplant, cauliflower, horseradish, morning glory, poplar, walnut, apple, grape, asparagus, cassava, rice, maize, millet, onion, barley, orchard grass, oat, rye, and wheat.

Such cells and plants are available from a wide range of sources including the American Type Culture Collection (Rockville, Md.), or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil, *Cell Culture and Somatic Cell Genetics of Plants*, Vol I, II, III, *Laboratory Procedures and Their Applications*, Academic Press, New York, 1984; Dixon, *Plant Cell Culture-A Practical Approach*, IRL Press, Oxford University, 1985; and Green et al., *Plant Tissue and Cell Culture*, Academic Press, New York, 1987.

Construction of Plant Transgenes

ICS genes, as well as genes encoding other members of the ICS pathway, genes involved in siderophore production, and genes encoding transcription factors involved in these pathways, can be cloned into any of a number of suitable vectors for expression of these genes in plants. A number of vectors suitable for stable or extrachromosomal transfection of plant cells or for the establishment of transgenic plants are available to the public. Such vectors are described in Pouwels et al. (*Cloning Vectors: A Laboratory Manual*, 1985, Supp. 1987), Weissbach et al. (*Methods for Plant Molecular Biology*, Academic Press, 1989), and Gelvin et al. (*Plant Molecular Biology Manual*, Kluwer, Academic Publishers, 1990). Methods for constructing such cell lines are described in, for example, Weissbach et al. (supra) and Gelvin et al. (supra).

Typically, plant expression vectors include (1) a cloned plant gene under the transcriptional control of 5' and 3' regulatory sequences, and (2) a dominant selectable marker. Such plant expression vectors can also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal. Once a desired nucleic acid molecule is obtained, as described above, it can be manipulated in a variety of ways known in the art. For example, where the sequence includes non-coding flanking regions, the flanking regions can, if desired, be subjected to mutagenesis or deleted.

The isochorismate synthase sequence can, if desired, be combined with other DNA sequences in a variety of ways. For example, the DNA sequence of the invention can be employed with all or part of the gene sequences normally associated with the expression of isochorismate synthase. In its component parts, a DNA sequence encoding an isochorismate synthase is combined in a DNA construct having a transcription initiation control region capable of promoting transcription and translation in a host cell.

In general, the constructs will include regulatory regions that are functional in plants and provide for modified production of an isochorismate synthase as discussed herein. The open reading frame coding for the isochorismate synthase or functional fragment thereof will be joined at its 5' end to a transcription initiation regulatory region, such as the sequence naturally found in the 5' upstream region of the gene. Numerous other transcription initiation regions are available, which provide for constitutive or inducible regulation.

For applications in which developmental, cell, tissue, hormonal, or environmental expression is desired, appropriate 5' upstream non-coding regions are obtained from other genes, for example, from genes regulated during meristem development, seed development, embryo development, or leaf development.

Regulatory transcript termination regions can be provided in DNA constructs of this invention as well. Transcript termination regions can be provided by the DNA sequence encoding the isochorismate synthase or any convenient transcription termination region derived from a different gene source. The transcript termination region will contain, preferably, at least 1–3 kilobases of sequence 3' to the structural gene from which the termination region is derived.

Plant expression constructs having an isochorismate synthase gene as the DNA sequence of interest for expression (in either the sense or antisense orientation) can be employed with a wide variety of plant life. Such genetically-engineered plants are useful for a variety of industrial and agricultural applications as discussed infra, including the generation of disease resistant plants. Importantly, this invention is applicable to dicotyledons and monocotyledons, and will be readily applicable to any new or improved transformation or regeneration method.

The expression constructs include at least one promoter operably linked to at least one isochorismate synthase gene. An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. Examples of plant expression constructs using these promoters are described in Fraley et al., U.S. Pat. No. 5,352,605. In most tissues of transgenic plants, the CaMV 35S promoter is a strong promoter (see, for example, Odell et al., Nature 313:810–812, 1985). The CaMV promoter is also highly active in monocots (see, for example, Dekeyser et al., Plant Cell 2:591–602, 1990). Moreover, activity of this promoter can be further increased (i.e., between 2–10 fold) by duplication of the CaMV 35S promoter (see, for example, Fang et al., Plant Cell 1:141–150, 1989; and McPherson et al., U.S. Pat. No. 5,378,142).

Other useful plant promoters include, without limitation, the nopaline synthase (NOS) promoter (Rogers et al., U.S. Pat. No. 5,034,322), the octopine synthase promoter (Fromm et al., Plant Cell 1:977–984, 1989), figwort mosiac virus (FMV) promoter (Rogers, U.S. Pat. No. 5,378,619), the rice actin promoter (Wu et al., WO 91/09948), and the ubiquitin promoter system (Quail et al., U.S. Pat. No. 5,614,399). Exemplary monocot promoters include, without limitation, commelina yellow mottle virus promoter, sugar cane badna virus promoter, rice tungro bacilliform virus promoter, maize streak virus element, and wheat dwarf virus promoter.

For certain applications, it may be desirable to produce the isochorismate synthase in an appropriate tissue, at an appropriate level, or at an appropriate developmental time. For this purpose, there are an assortment of gene promoters, each with its own distinct characteristics embodied in its regulatory sequences, shown to be regulated in response to inducible signals, such as the environment, hormones, and/or developmental cues. These include, without limitation, gene promoters that are responsible for heat-regulated gene expression, light-regulated gene expression (for example, the pea rbcS-3A; the maize rbcS promoter; the chlorophyll a/b-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and Arabidopsis); and wound-induced gene expression (for example, of wunI), organ-specific gene expression (for example, of the tuber-specific storage protein gene; the 23-kDa zein gene from maize; or the French bean phaseolin gene), or pathogen-inducible promoters (for example, the PR-1, prp-1, or glucanase promoters, the fungal-inducible wirla promoter of wheat, and the nematode-inducible promoters, TobRB7-5A and Hmg-1, of tobacco and parsley, respectively).

Preferred promoters for use in the invention are rapidly induced promoters. The success of plant defense against pathogens is dependent upon the timing of the response. In fact, in many cases, virulent and avirulent pathogens (i.e., pathogens harboring an avr gene recognized specifically by the plant) activate similar pathogenesis-related proteins (e.g., PR1, BGL2, and PDF1.2). However, the avirulent pathogens are recognized/detected more rapidly by the plant and, in response, these plant pathogenesis-related proteins are induced more rapidly than in an incompatible (virulent pathogen) interaction. For example, the edr1 mutant was isolated in a screen for Arabidopsis mutants that are more resistant to pathogens, and pathogenesis-related proteins (such as PR1) are more rapidly induced in response to pathogen in this mutant.

In the case of augmented plant resistance against pathogen using transgenic plants expressing salicylic acid via isochorismate synthase (e.g., ICS; SEQ. ID. NO.: 1 or PchA; SEQ. ID. NO.: 9) and pyruvate lyase (e.g., PchB), or expressing pyochelin via isochorismate synthase, pyruvate lyase, salicyl AMP ligase (e.g., PchD), dihydroaeruginoic acid synthetase (e.g., PchE), and pyochelin synthetase (e.g., PchF), the use of rapid response pathogen-induced promoters to drive expression of these constructs is particularly valuable.

At ICS1, which is responsible for endogenous production of salicylic acid via isochorismate is expressed more rapidly in response to avirulent pathogens than to virulent pathogens (e.g., Psm+/−avrRpt2). The rapid induction of At ICS1 in the incompatible interaction leads to plant resistance, whereas the slower induction of At ICS1 in the compatible interaction may allow the virulent pathogen to colonize the plant, resulting in disease. This rapid induction of At ICS1 in an incompatible interaction (avirulent pathogen) is then associated with the rapid induction of PR1 and other pathogenesis-related proteins that result in enhanced resistance to pathogens. The induction of these other proteins may result directly or indirectly from salicylic acid. For example, the exogenous application of salicylic acid has been shown to induce pathogenesis-related proteins including PR1 and to increase plant resistance to pathogens. In addition, the induction of these pathogenesis-related proteins may result directly or indirectly from yet undefined products derived from pathogen-inducible isochorismate. To illustrate this point, in the Arabidopsis sid2 mutants (sid2-2/leds16-1 and sid2-1), which are null mutants in ICS1, meaning that they do not express active ICS1, PR1 induction in response to pathogen is minimal (e.g., <1% of wild-type induction of PR1 in response to the powdery mildew Erysiphe orontii).

The channeling of plant resources (e.g., carbon) to secondary products (e.g., isochorismate, salicylic acid, and pyochelin) incurs an associated cost to the plant that may negatively impact plant growth and yield if these products are expressed constitutively (e.g., using the CaMV 35S promoter). In addition, the three major secondary metabolic pathways from chorismate are tightly regulated and coupled. Of interest, secondary products derived from each of these three pathways (from anthranilate, from isochorismate, and from prephenate) are involved in plant defense against pathogen and response to environmental stress. One primary level of regulation controlling allocation to these different pathways and products involves differential induction of the anthranilate synthase, isochorismate synthase, and chorismate mutase genes, each of which exist in a pathogen-inducible form in plants. The characterized pathogen-inducible AS, ICS, and CM plant proteins have relatively high and similar $K_m$'s for chorismate. $K_m$, the Michaelis constant, is defined as the substrate concentration that is sufficient to give half the maximum velocity for an enzyme, and is a general indicator of an enzyme's operational range in vivo. Because of the relatively high $K_m$ of isochorismate synthase for chorismate, it is preferable to express it only when the entire shikimate pathway resulting in the production of chorismate is upregulated. In addition, this would limit the associated cost of draining resources to this pathway when it is not needed.

Preferably, salicylic acid (via ICS, SEQ. ID. NO.: 1 and PchB) and pyochelin (via ICS, PchB, PchD, PchE, and PchF) is expressed only upon exposure to pathogen, very rapidly. The timing of optimal expression is such that these genes should be expressed before the onset of visible disease symptoms, at which point it is typically too late to effectively limit pathogen spread. Therefore, we propose expressing salicylic acid and pyochelin by the methods described above under the control of a rapid response pathogen inducible promoter. Ideally, these promoters would respond to a broad range of virulent and avirulent pathogens and induce salicylic acid and pyochelin within hours of exposure (preferably 12 hours or less, with more preference for 6 hours or less, with greater preference for 1 hour or less, and with highest preference for 30 minutes or less).

One example of a rapid response pathogen inducible promoter is the parsley WRKY1 promoter, which is induced within 15 minutes of elicitation. Other rapid response pathogen inducible promoters include the tobacco EREBP1 promoter (Horvath et al., MPMI 11:895–905, 1998), the BiP (lumenal binding protein) promoter, which is induced by cell-wall degrading enzymes more rapidly than PR proteins (Jelitto-Van Dooren et al., Plant Cell 11:1935–1943, 1999), and the *Arabidopsis* SA-glucosyltransferase promoter (Accession No. AC006248.3, PID g4335715).

Plant expression vectors can also, optionally, include RNA processing signals, e.g, introns, which have been shown to be important for efficient RNA synthesis and accumulation (Callis et al., Genes and Dev. 1:1183–1200, 1987). The location of the RNA splice sequences can dramatically influence the level of transgene expression in plants. In view of this fact, an intron can be positioned upstream or downstream of an isochorismate synthase coding sequence in the transgene, to modulate levels of gene expression.

In addition to the aforementioned 5' regulatory control sequences, the expression vectors can also include regulatory control regions that are generally present in the 3' regions of plant genes. For example, a 3' terminator region can be included in the expression vector to increase stability of the mRNA. One such terminator region can be derived from the PI-II terminator region of potato. Other commonly used terminators are derived from the octopine or nopaline synthase signals.

The plant expression vector also typically contains a dominant selectable marker gene used to identify cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis can also be used as selectable markers in photosynthetic-deficient strains. Finally, genes encoding herbicide resistance can be used as selectable markers; useful herbicide resistance genes include the bar gene, encoding the enzyme phosphinothricin acetyltransferase and conferring resistance to the broad spectrum herbicide Basta® (Hoechst Marion Rousel, Frankfurt, Germany).

Efficient use of selectable markers is facilitated by a determination of the susceptibility of a plant cell to a particular selectable agent and a determination of the concentration of this agent that effectively kills most, if not all, of the transformed cells. Some useful concentrations of antibiotics for tobacco transformation include, for example, 20–100 µg/ml (kanamycin), 20–50 µg/ml (hygromycin), or 5–10 µg/ml (bleomycin). A useful strategy for selection of transformants for herbicide resistance is described, for example, by Vasil et al., supra.

In addition, if desired, the plant expression construct can contain a modified or fully-synthetic structural isochorismate synthase coding sequence that has been changed to enhance the performance of the gene in plants. Methods for constructing such a modified or synthetic gene are described in Fischoff et al., U.S. Pat. No. 5,500,365.

It should be readily apparent to those skilled in the art of molecular biology, especially in the field of plant molecular biology, that the level of gene expression is dependent not only on the combination of promoters, RNA processing signals, and terminator elements, but also on how these elements are used to increase the levels of selectable marker gene expression.

Plant Transformation

Upon construction of a plant expression vector, several standard methods, as described above, are available for introduction of the vector into a plant host, thereby generating a transgenic plant. Although described in reference to vectors containing ICS genes, the following transformation and plant regeneration methods can be used for any of the other genes of interest described above (e.g., other genes in the ICS pathway, genes that are involved in siderophore production, and genes that encode transcription factors that are involved in controlling expression of genes that are in these pathways).

These methods include (1) *Agrobacterium*-mediated transformation (*A. tumefaciens* or *A. rhizogenes*) (see, for example, Lichtenstein et al., In: *Genetic Engineering*, vol. 6, Rigby, ed., London, Academic Press, 1987 and Lichtenstein, In: *DNA Cloning*, Vol II, D. M. Glover, ed., Oxford, IRI Press, 1985), (2) the particle delivery system, (3) microinjection protocols, (4) polyethylene glycol (PEG) procedures, (5) liposome-mediated DNA uptake, (6) electroporation protocols, (7) the vortexing method, or (8) the so-called whiskers methodology (see, for example, Coffee et al., U.S. Pat. No. 5,302,523). The method of transformation is not critical to the invention. Any method that provides for efficient transformation can be employed. As newer methods become available to transform crops or other host cells, they can be directly applied. Suitable plants for use in the practice of the invention include, but are not limited to, sugar cane, wheat, rice, maize, sugar beet, potato, barley, manioc, sweet potato, soybean, sorghum, cassava, banana, grape, oats, tomato, millet, coconut, orange, rye, cabbage, apple, watermelon, canola, cotton, carrot, garlic, onion, pepper, strawberry, yam, peanut, onion, bean, pea, mango, citrus plants, walnuts, and sunflower.

The following is an example outlining one particular technique, an Agrobacterium-mediated plant transformation. By this technique, the general process for manipulating genes to be transferred into the genome of plant cells is carried out in two phases. First, cloning and DNA modification steps are carried out in *E. coli*, and a plasmid containing the gene construct of interest is transferred by conjugation or electroporation into *Agrobacterium*. Second, the resulting *Agrobacterium* strain is used to transform plant cells. Thus, for a generalized plant expression vector, the plasmid contains an origin of replication that allows it to replicate in *Agrobacterium* and a high copy number origin of replication that is functional in *E. coli*. This permits facile production and testing of transgenes in *E. coli*, prior to transfer to *Agrobacterium* for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of *Agrobacterium*, delimit the DNA region that will be transferred to the plant.

In another example, plant cells can be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plant cells transformed with a plant expression vector can be regenerated, for example, from single cells, callus tissue, or leaf discs, according to standard plant tissue culture techniques. It is well known in the art that various cells, tissues, and organs from almost any plant can be successfully cultured to regenerate an entire plant; such techniques are described, for example, in Vasil, supra; Green et al., supra; Weissbach, supra; and Gelvin et al., supra.

In one particular example, an expression construct containing a cloned isochorismate synthase gene under the control of the 35S CaMV promoter and the nopaline synthase terminator and carrying a selectable marker (for example, kanamycin resistance) is transformed into *Agrobacterium*. Transformation of leaf discs (for example, of tobacco or potato leaf discs) with vector-containing *Agrobacterium* is carried out as described by Horsch et al. (Science 227:1229–1231, 1985). Putative transformants are selected after a few weeks (for example, 3 to 5 weeks) on plant tissue culture media containing kanamycin (for example 100 µg/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less medium and grown in a greenhouse. Kanamycin-resistant progeny are selected by sowing surfaced sterilized seeds on hormone-free kanamycin-containing media. Analysis for the integration of the transgene is accomplished by standard techniques (see, for example, Ausubel et al., supra; Gelvin et al., supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, for example, Ausubel et al., supra). The RNA-positive plants are then analyzed for protein expression by western immunoblot analysis using isochorismate synthase polypeptide-specific antibodies (see, for example, Ausubel et al., supra). In addition, in situ hybridization and immunocytochemistry according to standard protocols can be done using transgene-specific nucleotide probes and antibodies, respectively, to localize sites of expression within transgenic tissue.

Other Embodiments

The invention further includes the use of analogs of any naturally-occurring plant isochorismate synthase or other polypeptide of interest, as described above. Analogs can differ from the naturally-occurring polypeptide by amino acid sequence differences, by post-translational modifications, or by both. Analogs of the invention will generally exhibit at least 40%, more preferably 50%, and most preferably 60%, or even 70%, 80%, or 90% identity, with all or part of a naturally-occurring plant isochorismate synthase polypeptide amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, for example, acetylation, carboxylation, phosphorylation, or glycosylation; such modifications can occur during polypeptide synthesis or processing or following treatment with isolated modifying enzymes. Analogs can also differ from the naturally-occurring isochorismate synthase polypeptide by alterations in primary sequence. These include genetic variants, both natural and induced (for example, resulting from random mutagenesis by irradiation or exposure to ethyl methylsulfate or by site-specific mutagenesis as described in Sambrook et al., supra, or Ausubel et al., supra). Also included are cyclized peptides, molecules, and analogs which contain residues other than L-amino acids, for example, D-amino acids or non-naturally occurring or synthetic amino acids.

In addition to full-length polypeptides, the invention also includes use of isochorismate synthase polypeptide fragments, as well as fragments of the other polypeptides of interest described herein. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments can be generated by methods known to those skilled in the art or can result from normal protein processing (for example, removal of amino acids from the nascent polypeptide that are not required for biological activity or removal of amino acids by alternative mRNA splicing or alternative protein processing events).

Furthermore, the invention includes nucleotide sequences that facilitate specific detection of a gene encoding an isochorismate synthase or other polypeptide of interest, as described herein. Thus, the nucleic acid sequences described herein or portions thereof can be used as probes to hybridize to nucleotide sequences from other plants (for example, dicots, monocots, gymnosperms, and algae) by standard hybridization techniques under conventional conditions. Sequences that hybridize to an isochorismate synthase polypeptide coding sequence or its complement and that encode an isochorismate synthase polypeptide are considered useful in the invention. As used herein, the term "fragment," as applied to nucleic acid sequences, means at least 5 contiguous nucleotides, preferably at least 10 contiguous nucleotides, more preferably at least 20 to 30 contiguous nucleotides, and most preferably at least 40 to 80 or more contiguous nucleotides. Such fragments can be generated by methods known to those skilled in the art.

The methods described herein are based, in part, on the experimental results and methods described below. Three mutants are described below, but one of these, eds16, is the mutant upon which the methods and claims described herein are primarily based. Briefly, previous studies have shown that salicylic acid in plants is produced via Pathway 1, as shown in FIG. 1. Based on our characterization of eds16, we have shown that an alternate pathway, Pathway 2 in FIG. 1, exists in plants. In this pathway, chorismate, which is produced from the Shikimate pathway, is converted by iscochorismate synthase into isochorismate, which is, in turn, converted into salicyclic acid.

Experimental Results

To enhance our understanding of the mechanisms by which plants restrict growth of a biotrophic fungal pathogen, our laboratory has isolated a collection of *Arabidopsis* mutants that are specifically attenuated in defense responses. Here we describe a set of mutants that were identified on the basis that they are more susceptible to infection by *E. orontii*. Three of these eds mutants correspond to defense-response genes that had not been identified previously in our laboratory and have been characterized with regard to susceptibility to multiple pathogens and induction of defense responses that are mediated by different signaling pathways. These three mutants further illustrate the complexity and specificity of plant defense response pathways.

Isolation of Mutants with Enhanced Susceptibility to *E. orontii*

Figure 2:
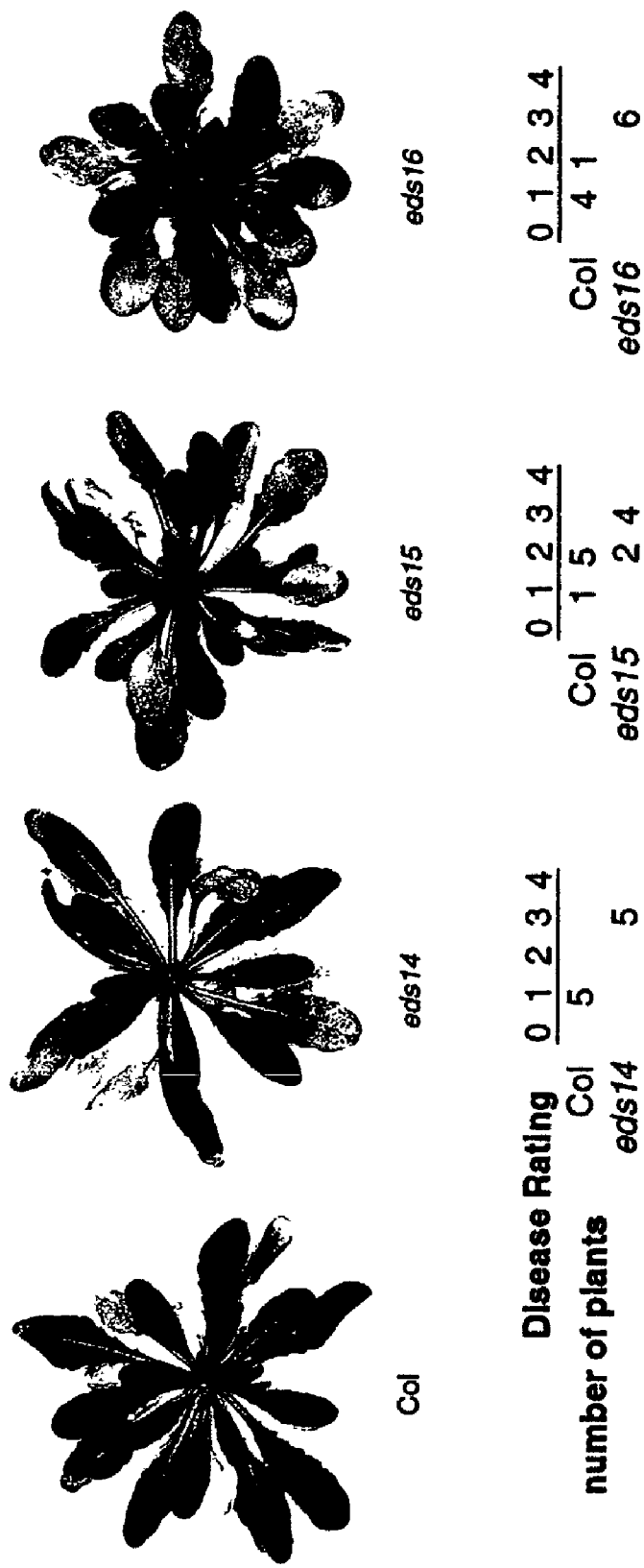
FIG. 2 shows the susceptibility of eds16-1/sid2-2 to *Erysiphe orontii*, by showing powdery mildew disease symptoms in eds mutants and wild type. The photographs show *E. orontii* infected plants at 17 day post inoculation (dpi). The Disease Rating charts show disease scores in side-by-side comparison between mutant plants and wild type plants. Plants were scored at 10 days after inoculation, using a scoring system developed by Reuber et al., supra. 0 indicates no visible symptoms of infection and 4 indicates approximately 100% coverage of infected leaves. For each line, mutant and wild type (Col-0) plants were intermingled in the same cell to minimize inoculum variability. M4 plants were used for the photographs but similar results were observed in mutant F2 progeny after backcrossing each line to Col-0.

Approximately 13,000 four-week old M2 plants from ecotype Columbia seed that had been mutagenized by EMS treatment or fast neutron bombardment were inoculated with *E. orontii* isolate MGH. Twelve to 14 days after inoculation, the amount of fungal growth was visually assessed. After one round of screening, 376 (2.8%) plants were selected for re-testing. Fifty-two lines were confirmed to have an enhanced disease susceptibility (eds) phenotype. Using a scoring system that ranks disease symptoms according to the amount of leaf area covered by powdery mildew (Reuber et al., supra), the mutants were found to vary in the severity of symptoms, from slightly more susceptible than Columbia to considerably more so (FIG. 2). Sixteen mutants with the most reproducible phenotypes were chosen for further characterization.

Prioritization of Mutants for Further Analysis

Each of the 16 mutants chosen for further analysis was backcrossed to the parental line, Col-0, and the F1 progeny were scored for enhanced disease susceptibility. For all 16 mutants, the F1 progeny were wild type in their susceptibility to *E. orontii*, indicating that all of the corresponding eds mutations were recessive.

To ascertain whether the 16 eds mutants represented new alleles of previously identified defense response mutants, which were known to be more susceptible to *E. orontii* (Reuber et al., supra and Volko et al., supra), a series of assays was performed (Table 1). To determine whether any were allelic to pad4, which is deficient in induction of the phytoalexin camalexin in response to *P. syringae* infection (Glazebrook, et al., 1996, supra), the mutants were assayed for camalexin levels in infected tissue. Because *E. orontii* induces only low levels of camalexin accumulation in wild type plants (Reuber et al., supra), plants were inoculated with Psm ES4326 for these assays. Three of the mutants (J1, J2, and R1) produced markedly lower levels of camalexin. Two of the mutants were not assayed for camalexin, as other tests suggested that they were not pad4 alleles (Table 1). To test further whether any of the 16 mutants were alleles of pad4, all but S5 (see below) were crossed to pad4 and the F1 progeny were scored for susceptibility to *E. orontii*. The three phytoalexin-deficient mutants failed to complement pad4, and were therefore eliminated from further analysis in this study. As two of these pad4 mutants were from the same batch of mutagenized seed, they are likely to be siblings, so we concluded that a total of two new pad4 mutants were isolated in this screen. These are further described by Jirage et al., supra.

Another class of mutants with attenuated defenses against some pathogens have lesions in ethylene signaling (Knoester et al., Proc. Natl. Acad. Sci. U.S.A. 95:1933–1937, 1998 and Thomma et al., 1999). In particular, ein2 is more susceptible to *E. orontii*. To test for deficiencies in ethylene signaling, the remaining 13 mutants were tested for sensitivity to ACC, an ethylene precursor. One of the 13 mutants, S5, was ethylene insensitive and discarded in the current study as a putative ein2 mutant.

TABLE 1

Assays for allelism with known defense related genes

| line | Psm induction of camalexin | SA induction of PR-1 | growth on ACC | complementation tests | | | | |
|---|---|---|---|---|---|---|---|---|
| | | | | pad4 | eds1 | eds5 | eds10 | eds13 |
| C2 (eds14) | wt | Wt | wt | + | + | nt | nt | + |
| Q1 (eds15) | ~wt | Wt | wt | + | + | nt | + | + |
| R2 (eds16) | ~wt | Wt | wt | + | + | + | + | + |
| H1 | wt | Wt | wt | + | + | | | |
| H2 | wt | Wt | wt | + | + | | | |
| J1 | low | Wt | nt | − | nt | | | |
| J2 | low | Nt | wt | − | nt | | | |
| J5 | wt | Nt | wt | + | + | | | |
| K16 | nt | Wt | wt | + | nt | | | |
| O3 | wt | Wt | wt | + | + | | | |
| O6 | wt | Wt | wt | + | + | | | |
| R1 | low | Wt | nt | − | nt | | | |
| S5 | nt | Nt | Insensitive | nt | nt | | | |
| S14 | wt | Wt | wt | + | + | | | |
| S23 | wt | Wt | wt | + | + | | | |
| T7 | wt | Wt | wt | + | + | | | |

"+" indicates complementation and "−" indicates failure to complement
"wt" indicates wild type; "nt" indicates not tested The product of the NPR1 gene has also been shown to have a vital role in plant defenses, as mutations in NPR1 cause plants to become more susceptible to a variety of pathogens, including E. orontii (Cao et al., supra; Delaney et al., supra; Glazebrook et al., 1996; Reuber et al., supra; and Volko et al., supra). One of the characteristics of npr1 plants is their inability to induce PR-1 expression after treatment with salicylic acid (Cao et al., supra; Delaney et al., supra; and Shah et al., supra) Mutants other than those identified as pad4 or ACC insensitive were assayed for PR-1 mRNA accumulation after treatment with 0.5 mM SA, with the exception of one mutant (J5), which failed to grow on SA plates. In all the lines tested, PR-1 levels were comparable to those in wild type (Table 1). Therefore we concluded that none of the mutations were in NPR1. In addition to pad4, npr1, and ein2, the mutant eds1 (Parker et al., The Plant Cell 8:2033–2046, 1996) is also more susceptible to E. orontii. After discontinuing the analysis of the pad4 and putative ein2 mutants plus one mutant (K16) that did not have a strong phenotype in the backcrossed line, the remaining 11 mutants were crossed to eds1. According to the disease susceptibility phenotype in the F1 progeny, none of the mutants that we tested were alleles of eds1.

We chose three of the mutants to study in detail for this study. Mutants C2, Q1, and R2 appeared to be novel based on the assays described above, maintained a moderate to strong phenotype after being backcrossed to Col-0, and segregated in the F2 progeny of the backcross as single recessive mutations (Table 2). We confirmed that none of these three mutants were allelic to each other by pairwise crosses. In all cases, E. orontii susceptibility in the F1 progeny was no greater than in wild type, demonstrating that these mutants are not allelic to each other.

TABLE 2

Segregation analysis of the eds phenotype

| line | wt | mutant | chi$^2$ | P |
|---|---|---|---|---|
| C2 (eds14) | 88 | 22 | 1.72 | 0.2 > P > 0.05 |
| Q1 (eds15) | 65 | 22 | 0.0038 | 0.99 > P > 0.95 |
| R2 (eds16) | 39 | 12 | 0.061 | 0.95 > P > 0.80 |

Segregation was scored in E orontii infected F2 progeny from the backcross to Col.

Next, we tested C2, Q1, and R2 for allelism with three additional eds mutants, eds5 (Rogers et al., supra), eds10 (Volko et al., supra), and eds13 (Id.), which are also more susceptible to E. orontii (Reuber et al., supra and Volko et al., supra). Based on the phenotype of C2 in a bacterial growth assay (see below), we concluded that C2 does not correspond to eds5, eds10, or eds13. Q1 and R2 were each crossed to eds10 and eds13. The F1 progeny were scored for E. orontii growth and in all cases the F1 susceptibility was wild type (Table 1), indicating that Q1 and R2 are not allelic to these eds loci. On the basis of defense related gene induction patterns (see below), we reasoned that, of the three mutants being analyzed, only R2 might be allelic to eds5, as both show a significant deficiency in PR-1 induction. The wild type phenotype of the F1 from a R2×eds5 cross indicates that they represent different loci.

Based on these analyses, we concluded that C2, Q1, and R2 represent new loci that play a role in defense of Arabidopsis against fungal pathogens, and have re-named them eds14 (C2), eds15 (Q1), and eds16 (R2). Mutations in eds15 and eds16 were generated by fast neutron bombardment and by EMS in eds14.

Mapping

To create mapping populations for each of the mutants, eds14, eds15, and eds16 were crossed to the Arabidopsis ecotype Landsberg erecta. However, the eds phenotype did not segregate 1:3, as expected, in any of the three crosses. In the eds14×La-er and eds15×La-er crosses, fewer than 1 in 4 F2s had an eds phenotype, although they segregated 1:3 in a backcross to Columbia. Without a correlative molecular marker such as PR gene expression to verify the genotype of the F2s, we felt that they did not constitute a good mapping population. We are currently working on developing an alternate mapping line that will provide a more compatible genetic background for detection of the eds phenotype. In the eds16 mapping population, the F2 progeny segregated approximately 1:3 for enhanced susceptibility. However, when these F2s were checked for loss of PR-1 induction, which co-segregated with the eds phenotype in the backcross to Columbia, only about 50% were found to express this trait, implying that only about 50% were homozygous for eds16. Twenty F2s that were homozygous were scored for a set of 22 CAPS markers distributed throughout the genome (Drenkard et al., In Caetano-Annollés et al. (eds.), DNA Markers Protocols, Applications and Overviews. Wiley-VCH, NY, pp. 187–197, 1997 and Konieczny et al., Plant Journal 4:403–410, 1993). The results indicated that the mutation was located on the lower arm of chromosome 1. To obtain a finer map position, we scored 65 F2s that were homozygous (based on RNA blot analysis to score PR-1 expression) with the CAPS marker PAB5 and the SSLP markers nga111 and AthATPase (Bell et al., Genomics 19:137–144, 1994). Markers PAB5 and AthATPase showed 1.54% and 1.56% recombination, respectively, with eds16, while no recombination was observed between eds16 and nga111. The mutation in eds16 was also mapped in collaboration with Cho et al. to test a newly developed microarray-based mapping technique using biallelic SNP markers (Cho et al., supra). Results from the two methods localized eds16 to the same region of chromosome 1.

Backcrossed lines were generated for eds14, eds15, and eds16, and used in all subsequent experiments.

eds14, eds15, and eds16 Show Differential Susceptibility to Other Pathogens

Figure 3A:
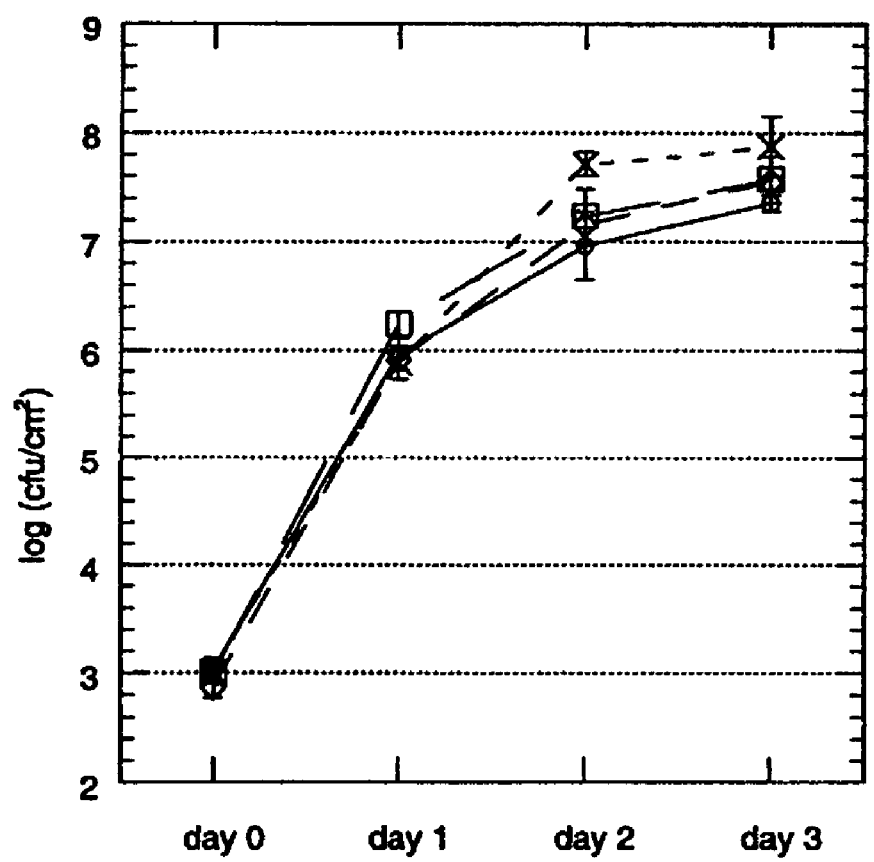
FIG. 3A is a line graph that shows the growth of virulent bacterial pathogens in the eds mutants. Leaves were inoculated with Psm at a dose of $10^3$ cfu/cm$^2$ and leaf disks harvested from 5 or 6 plants per line for growth assays at each of the times indicated. In the graph, the circles represent Col; the squares represent eds14; the diamonds represent eds15; and crosses represent eds16. Experiments were performed twice with similar results.

To determine whether the deficiencies in eds14, eds15, and eds16 defenses are specific to *E. orontii* or also compromise defenses against other pathogens, we assayed the growth of a variety of both compatible and incompatible pathogens. The bacterial pathogen Psm ES4326 causes disease characterized by water-soaked lesions and chlorosis on multiple *Arabidopsis* ecotypes, including Col-0 (Dong et al., The Plant Cell 3:61–72, 1991 and Whalen et al., The Plant Cell 3:49–59, 1991). Four and ½-week old eds14, eds15, and eds16 plants were inoculated with Psm at a dose of $10^3$ cfu/cm$^2$ and the infected tissue was analyzed for bacterial densities at 0, 1, 2, and 3 dpi (days post inoculation) (FIG. 3A). All three mutants are slightly, but reproducibly, more susceptible to Psm proliferation than wild type plants. However, only in eds16 was the difference ever statistically significant and that was not reproducible in all experiments. In the four F3 families that were scored, the enhanced Psm growth phenotype co-segregated with the *E. orontii* eds phenotype when eds16 was backcrossed to wild type plants, indicating that the same mutation in eds16 is responsible for enhanced susceptibility to both Psm and *E. orontii*.

Figure 3B:
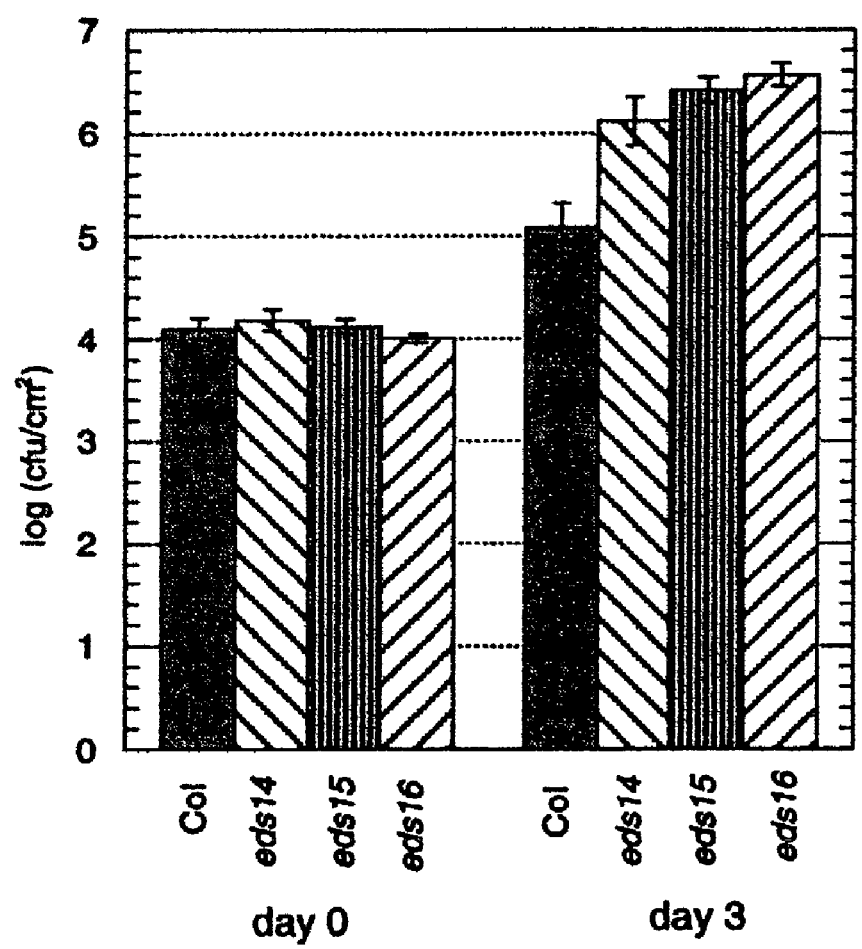
FIG. 3B is a bar graph that shows the growth of avirulent bacterial pathogens in the eds mutants. Leaves were inoculated with Psm at a dose of $10^4$ cfu/cm$^2$ and leaf disks harvested from 5 or 6 plants per line for growth assays at each of the times indicated. Experiments were performed twice with similar results.
Figure 3C:
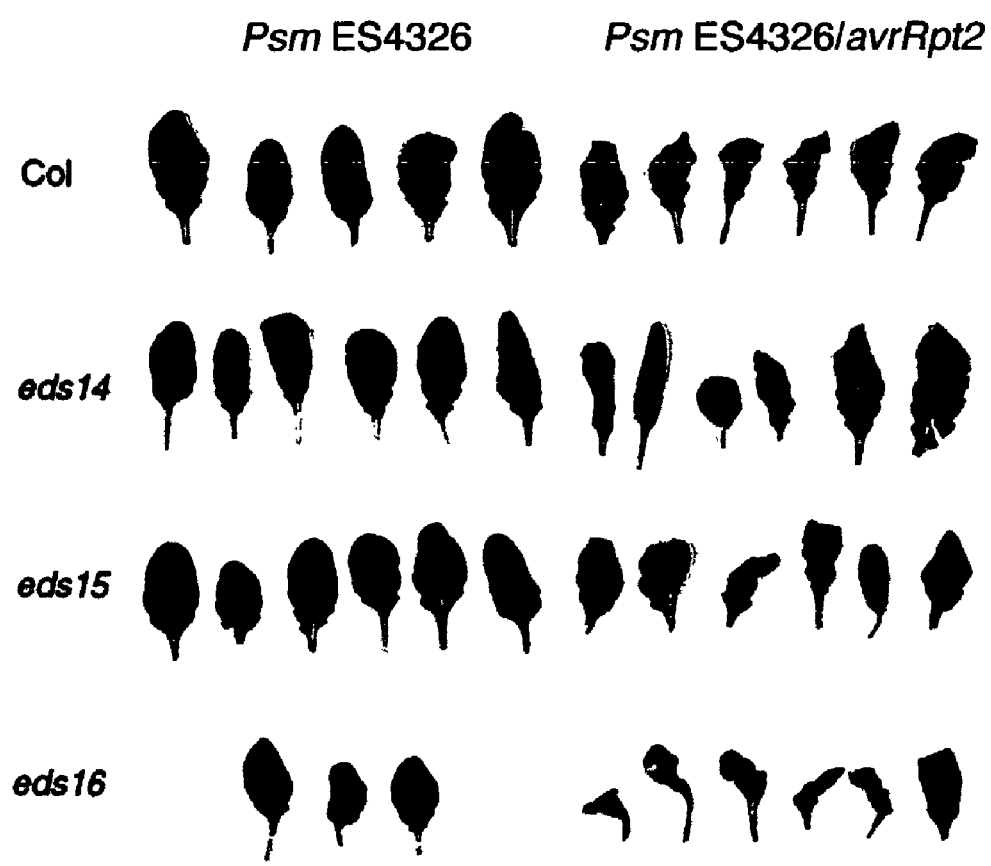
FIG. 3C are photographs that show the hypersensitive response in wild type and mutant plants inoculated with $10^5$ cfu/cm$^2$ Psm ES4326/avrRpt2. Leaves were photographed at 20 hours post inoculation (hpi).

An isogenic, incompatible strain of Psm expressing the avr gene avrRpt2 was also tested for growth in the mutants to determine whether any were compromised in R gene-mediated resistance. The avrRpt2 gene corresponds to RPS2, an R gene of the LZ-NBS/LRR class present in wild type Columbia. eds14, eds15, and eds16 were inoculated with a dose of $10^4$ cfu/cm$^2$ of Psm/avrRpt2 and analyzed for bacterial growth at 3 dpi (FIG. 3B). Although growth of this avirulent pathogen is not limited as much in the mutants (growth of 2 to 2.5 logs) as in wild type (growth of about 1 log), it is still restricted relative to the growth of the virulent strain (4.5 to 5 logs; FIG. 3A), indicating that R-avr-mediated resistance via the NDR1 pathway (Aarts et al., Proc. Natl. Acad. Sci. U.S.A. 95:10306–10311, 1998; Century et al., Proc. Natl. Acad. Sci. U.S.A. 92:6597–6601, 1995; and Century et al., Science 278:1963–1965, 1997) is functional in all three mutant lines. Using the same incompatible bacterial pathogen, all three lines were also tested for their ability to mount a hypersensitive response (HR). As shown in FIG. 3C, all of the mutants are capable of responding to avirulent Psm with an HR.

An alternative signaling pathway for R-avr gene mediated resistance is utilized by R genes in the TIR-NBS/LRR class (Aarts et al., Proc. Natl. Acad. Sci. U.S.A. 95:10306–10311, 1998). One of the components of this pathway is EDS1 (Aarts et al., Proc. Natl. Acad. Sci. U.S.A. 95:10306–10311, 1998). Mutations in EDS1 cause increased susceptibility to virulent *E. orontii* (Reuber et al., supra), as well as to some avirulent pathogens (Parker et al., The Plant Cell 8:2033–2046, 1996). Therefore, it was of interest to know if eds14, eds15, or eds16 was attenuated in resistance mediated by the EDS1 pathway. Growth of two different *Peronospora parasitica* isolates with avirulence genes that trigger resistance via TIR-NBS/LRR R genes in Columbia was assayed on the three mutants. In all cases, growth on the mutants was the same as on wild type Columbia.

Figure 4:
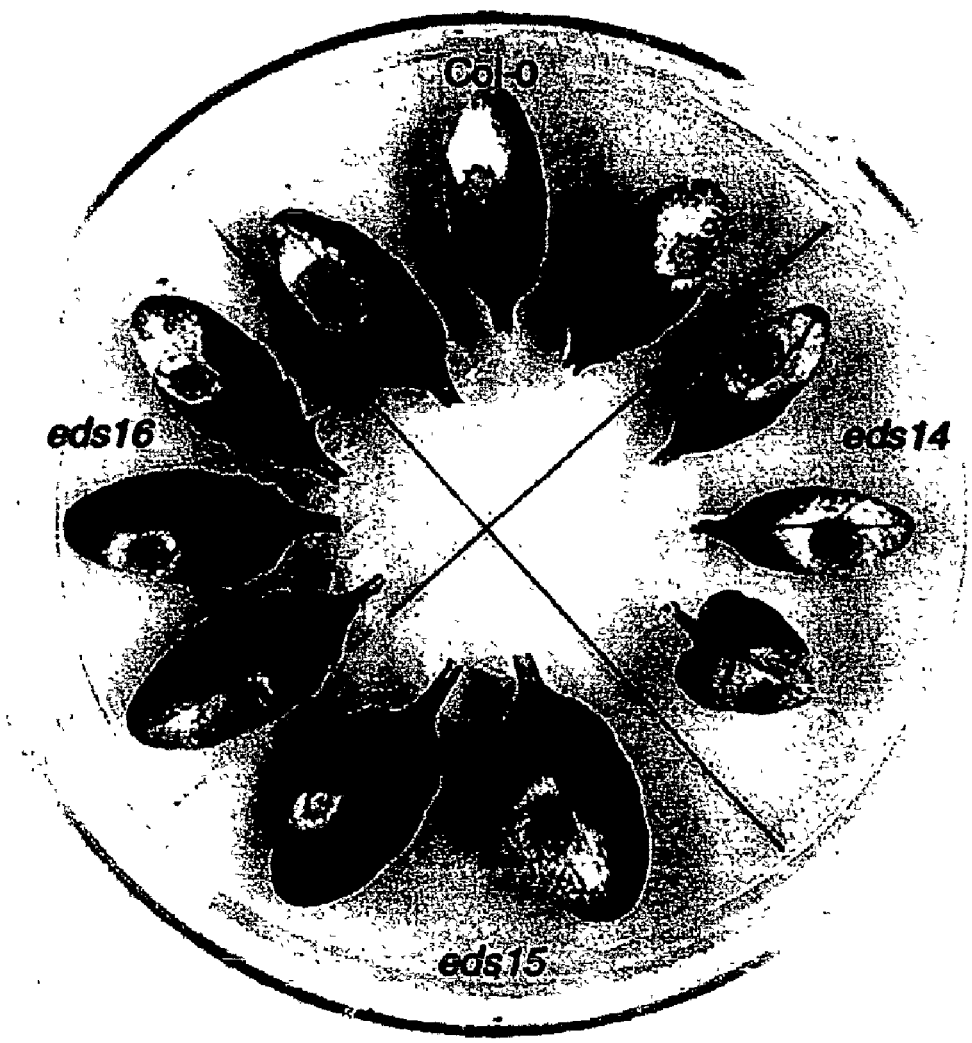
FIG. 4 is a photograph that shows the lack of enhanced susceptibility of eds16-1/sid2-2 to *Botrytis cinerea*. Disease symptoms in *B. cinerea* infected wild type and mutant leaves are shown. Leaf #7 was harvested, placed on water agar plates, and inoculated with a 5 μl drop of a 0.1×10$^6$ spores/ml suspension. Leaves were photographed at 4 dpi. Inoculations were done in 3 independent trials, using leaves from 9 to 12 plants in each trial, with similar results.

*E. cichoracearum* is closely related to *E. orontii* and, like *E. orontii*, is a biotrophic fungal pathogen that infects *Arabidopsis*. To assess the specificity of the effects of mutations in eds14, eds15, and eds16, they were tested for sensitivity to *E. cichoracearum*. eds14 and eds16 were both more susceptible than wild type plants. Surprisingly, however, eds15 was no more susceptible than the wild type control. To evaluate the consequences of the mutations in eds14, eds15, and eds16 on growth of a virulent necrotrophic fungal pathogen, detached leaves from wild type and mutant plants were inoculated with a suspension of spores from *Botrytis cinerea*. Mutations in the ethylene response pathway have been shown to increase susceptibility to this pathogen (Thomma et al., 1999). As shown in FIG. 4, none of the mutants in this study were more susceptible than wild type to *B. cinerea*.

Defense Responses are Altered in eds Mutants

Induction of Pathogenesis-related Genes

Figure 5:
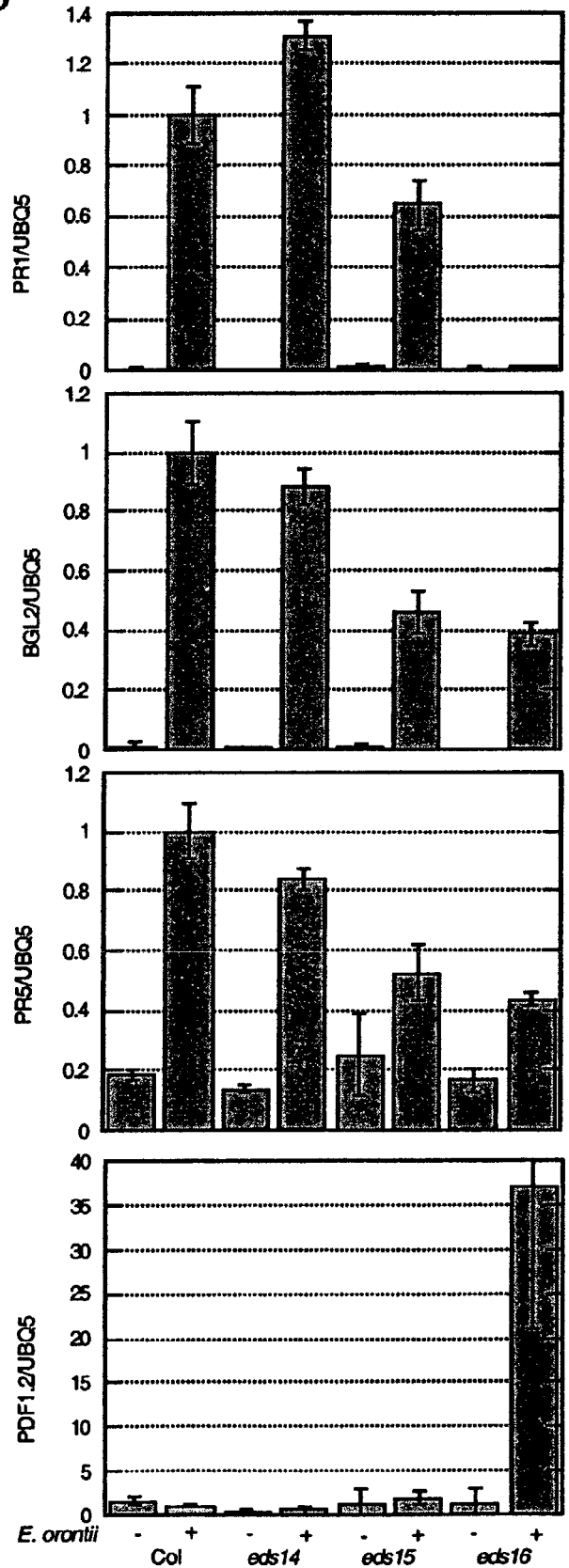
FIG. 5 are bar graphs that show that eds16-1/sid2-2 has altered defense gene induction in response to pathogen. Northern blot analysis of PR-1, BGL2, PR-5, and PDF1.2 mRNA accumulation is shown. Plants were inoculated 4.5 weeks after planting and harvested 7 dpi. Results from two samples of uninfected leaves and three samples of infected leaves were averaged. Each sample represents leaves from 3 to 4 plants. Expression was quantitated by phosphorimager, the ratio of defense related gene expression to UBQ5 expression calculated, and that ratio is expressed as a percentage of the ratio in wild type. The experiment was performed once with backcrossed lines, and the results were consistent with those in M4 plants. The particular defense genes monitored in each bar graph is as follows: PR-1 in "PR1/UBQ5;" BGL2 in "BGL2/UBQ5;" PR-5 in "PRR/UBQ5;" and PDF1.2 in "PDF1.2/UBQ5."

The defense related genes PR1, BGL2, PR5, and GST1 are induced by *E. orontii* infection in wild type Columbia, whereas PDF1.2 and Thi2.1 are not (Reuber et al., supra). Expression of PR1, BGL2, and PR5 in eds14, eds15, and eds16 was monitored by Northern blot analysis. No significant differences were seen between the mutant lines and Columbia in uninoculated samples. However, as shown in FIG. 5, all three mutants showed alterations in PR gene expression in infected leaves. In eds14, PR1 was reproducibly hyperinduced, whereas in eds16 PR-1, induction was dramatically reduced. BGL2 and PR-5 expression were also reduced in eds 16, by approximately 61% and 57%, respectively. In eds15, the induction of all three PR genes was low, ranging between 46% and 65% of wild type levels.

PDF1.2 mRNA accumulation was also assayed. Although not expressed at detectable levels in *E. orontii*-infected leaves of wild type plants, PDF1.2 was induced to relatively high levels in infected eds16 but not eds14 or eds15 leaves (FIG. 5). In an independent experiment, expression of PDF1.2 was as high in *E. orontii* infected eds16 as in Columbia tissue infected with *B. cinerea*, a pathogen that is known to induce this defense-response gene. The significance of this finding is that it suggests that *E. orontii* is capable of activating the JA/ethylene defense response pathway in addition to the salicylic acid pathway, which was not apparent in previous studies with wild type *Arabidopsis*.

Accumulation of Salicylic Acid

Figure 6:
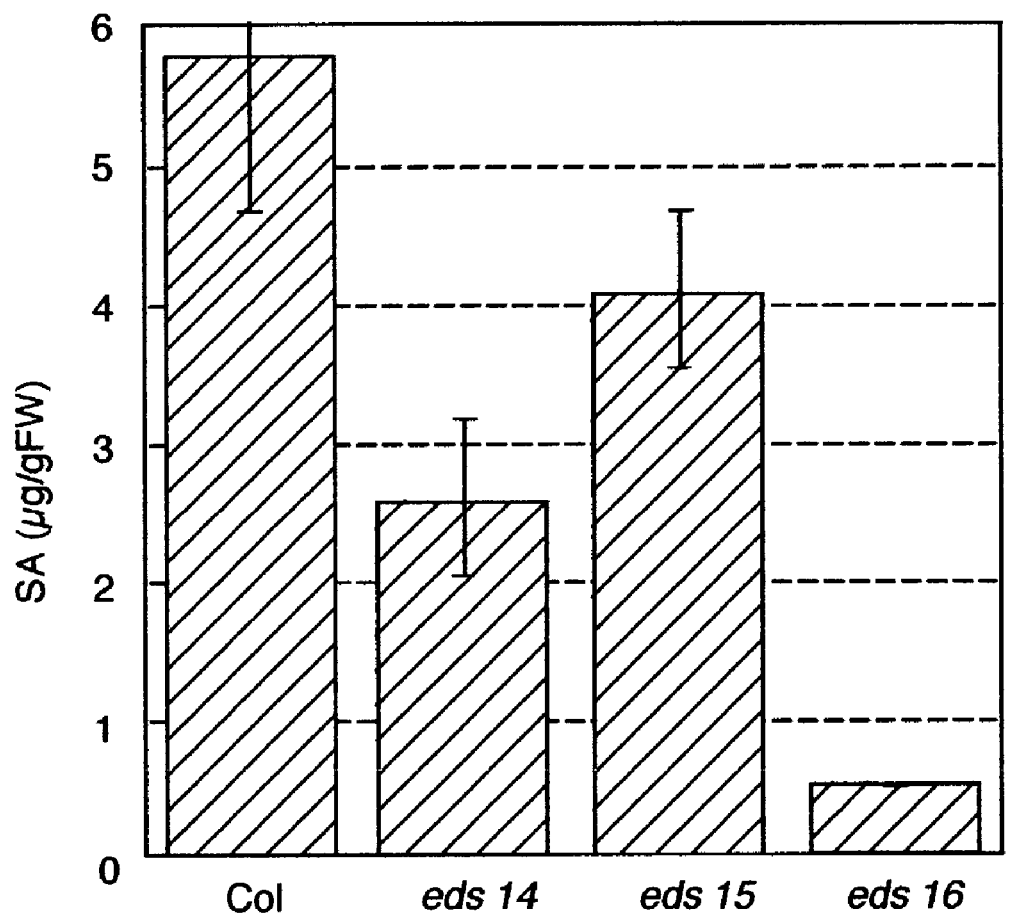
FIG. 6 is a bar graph that shows that eds16-1/sid2-2 is deficient in SA accumulation in response to pathogen. HPLC analysis of salicylic acid in mutants infected with *E. orontii* is shown. Plants were inoculated at 4.5 weeks old and harvested 7 dpi. Results for three samples, each representing several plants, were averaged for each line. The experiment was done once with M4 plants and once with backcrossed plants, with similar results.

The importance of salicylic acid (SA) as a signaling molecule in defense responses has been demonstrated in numerous experiments (reviewed in Dong, supra; Draper, supra; Glazebrook, 1999; and Wobbe et al., Plant Gene Research, Springer, pp. 167–196, 1996). To determine if SA levels were low in any of the mutants, extracts from *E. orontii*-infected leaves were analyzed by HPLC (FIG. 6). In Col-0, the concentration of total SA at 7 dpi was 5.6±1.0 μg/gFW (gram fresh weight). Total SA in *E. orontii*-infected leaves of each of the three mutants was lower than in wild type plants. The deficiency was greatest in eds16, which accumulated only 0.5 μg/gFW total SA, less than 10% of wild type levels. In eds14, SA concentrations were also significantly diminished relative to wild type, with accumulations of approximately 2.6 μg/gFW. Although the deficiency in SA accumulation was not as strong in eds15 as in the other two mutants, it too consistently accrued less than wild type plants.

Production of Camalexin

Previous analysis indicated that E. orontii infection did not elicit the accumulation of the phytoalexin camalexin (Reuber et al., supra). However, using a more sensitive HPLC assay, we have found that small amounts of camalexin are synthesized in E. orontii-infected Col-0 leaves. None of the mutants in this study consistently produced less camalexin than wild type plants and, in fact, eds16 reproducibly accumulated more.

Pathogen-induced Senescence

Pathogen infection can initiate senescence in leaves, which may be a form of programmed cell death that limits pathogen growth (Gan, supra and Pontier et al., Plant Molecular Biology 39:1243–1255, 1999). Mutant lines were scored for senescence by comparing the number of senescent leaves on mutant and wild type plants at intervals of several days up to 28 days after E. orontii inoculation. In intact plants, no differences were observed between any of the mutant lines and wild type. Interestingly, in a detached leaf assay, eds16 leaves, both infected and uninfected, were less senescent than wild type leaves at 11 dpi. It was observed that eds16 detached leaves were also more proficient at rooting than were wild type leaves, which may be the basis for delayed senescence in this line.

Callose Deposition

Figure 7:
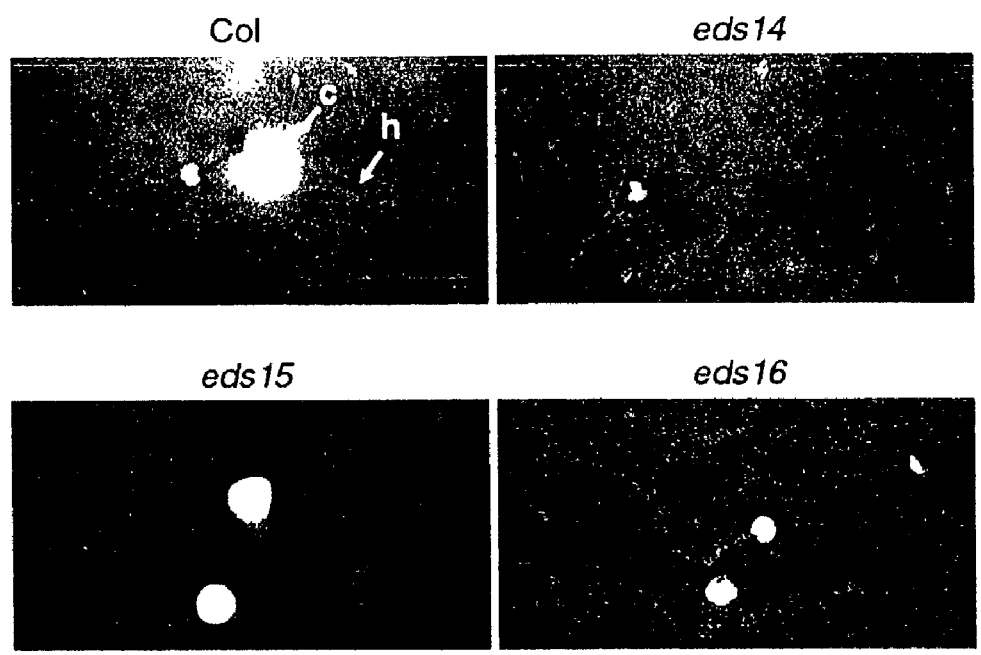
FIG. 7 is a photograph that shows that eds16-1 shows wild type papillae formation in response to *E. orontii*. Plants were inoculated with *E. orontii* at 4.5 weeks old and the leaves harvested 2 days later. Samples were stained with aniline blue to detect callose and then trypan blue to stain fungal structures. In the photograph the bar equals 0.1 mm, "c" represents cell wall apposition, and "h" represents fungal hypha.

Formation of cell wall appositions, or papillae, at sites of attempted penetration has been correlated with resistance to powdery mildew infections (Bayles et al., Physiological and Molecular Plant Pathology 36:63–72, 1990; Kobayashi et al., The Plant Journal 11:525–537, 1997; and Stanghellini et al., Phytopathology 83:1498–1501, 1993). eds14, eds15, and eds16 were evaluated for the formation of papillae during E. orontii infection by staining for callose, which is a major component of these cell wall reinforcements. Leaves were assayed at 1, 2, 3, and 5 days post-inoculation. No substantial differences between the mutants and wild type were seen. All of the mutant lines accumulated callose in discrete papillae beginning by 24 hpi (hours post inoculation), as in wild type, and continuing through 5 dpi. The response at 2 dpi is shown in FIG. 7.

The phenotypes of eds14, eds15, and eds16 are summarized in Table 3.

TABLE 3

Summary of phenotypic analysis of eds14, eds15, and eds16

|  | eds14 | eds15 | eds16 |
|---|---|---|---|
| Susceptibility to virulent pathogens | | | |
| E. orontii[1] | ++ | + | ++ |
| E. chichoracearum[1] | + | wt | ++ |
| Psm ES4326[2] | +0.2 | +0.2 | +0.5 |
| B. cinerea | wt | wt | wt |
| Resistance to avirulent pathogens | | | |
| LZ-NBS-LRR R gene mediated | yes | yes | yes |
| TIR-NBS-LRR R gene mediated | yes | yes | yes |
| Defense responses | | | |
| E. orontii induction of pathogenesis-related genes[3] | | | |
| PR-1 | 130% | 65% | <1% |
| BGL2 | 88% | 46% | 39% |
| PR-5 | 84% | 52% | 43% |
| PDF1.2 | 59% | 190% | 3700% |
| E. oronti-induced accumulation of salicylic acid[3] | ~50% | ~75% | <10% |
| E. orontii-induced senescence | wt | wt | wt |
| Callose deposition | yes | yes | yes |

"wt" indicates wild type
[1]susceptibility relative to Col-0, with +++ being the most susceptible
[2]log difference in growth relative to Col-0
[3]percentage of levels in wild type Complementation Analysis with sid2

The map position and low salicylic acid levels in infected tissue suggested that eds16 might be allelic to sid2 (Nawrath et al., supra). F1 and F2 progeny from a cross between the two mutants all had an eds phenotype when scored for E. orontii susceptibility. Accordingly, eds16 has been renamed sid2-2.

ICS1 Gene Expression is Deficient in sid2-2 Mutants

Figure 8:
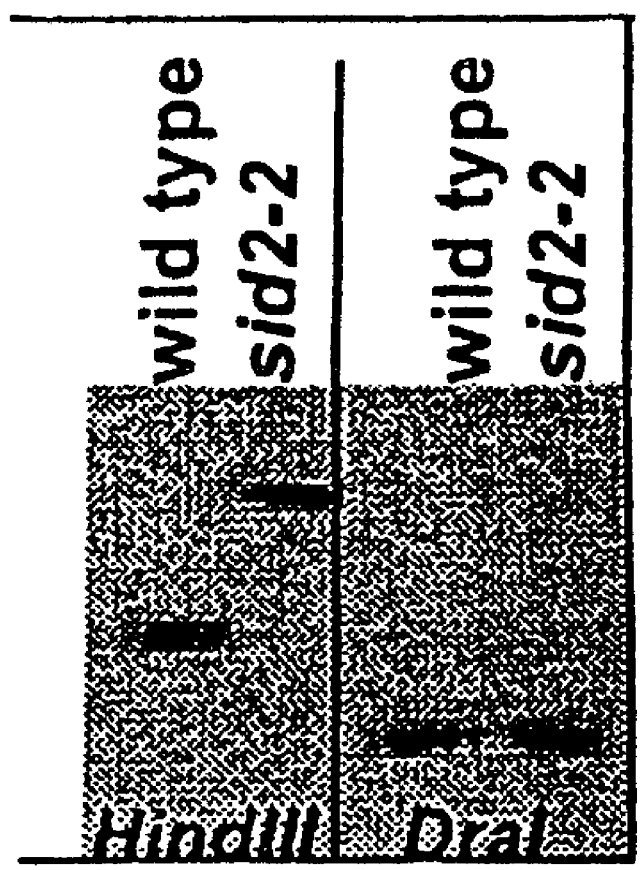
FIG. 8 is an autoradiograph that shows a polymorphism between sid2-2 and wild type *Arabidopsis* in the digestion pattern for HindIII. Wild type and sid2-2 show the same digestion pattern for DraI site that is found in ICS1 exon IX.
Figure 9A:
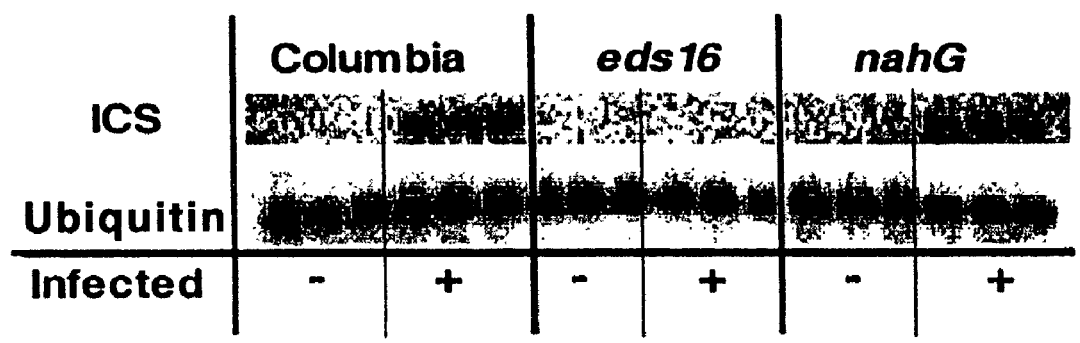
FIG. 9A is an autoradiograph that shows that eds16-1 is a null mutant in *Arabidopsis thaliana* isochorismate synthase 1(At ICS1). Expression of ICS RNA from eds16 was analyzed following infection with *E. orontii*. Columbia and nahG plants served as controls. sid2-2/eds16-1 is a fast neutron-generated mutant that contains a large deletion resulting in no mRNA transcript. The location of this deletion was characterized by PCR and sequencing using eds16-1 genomic DNA in comparison with Columbia (wild type) DNA.
Figure 12:
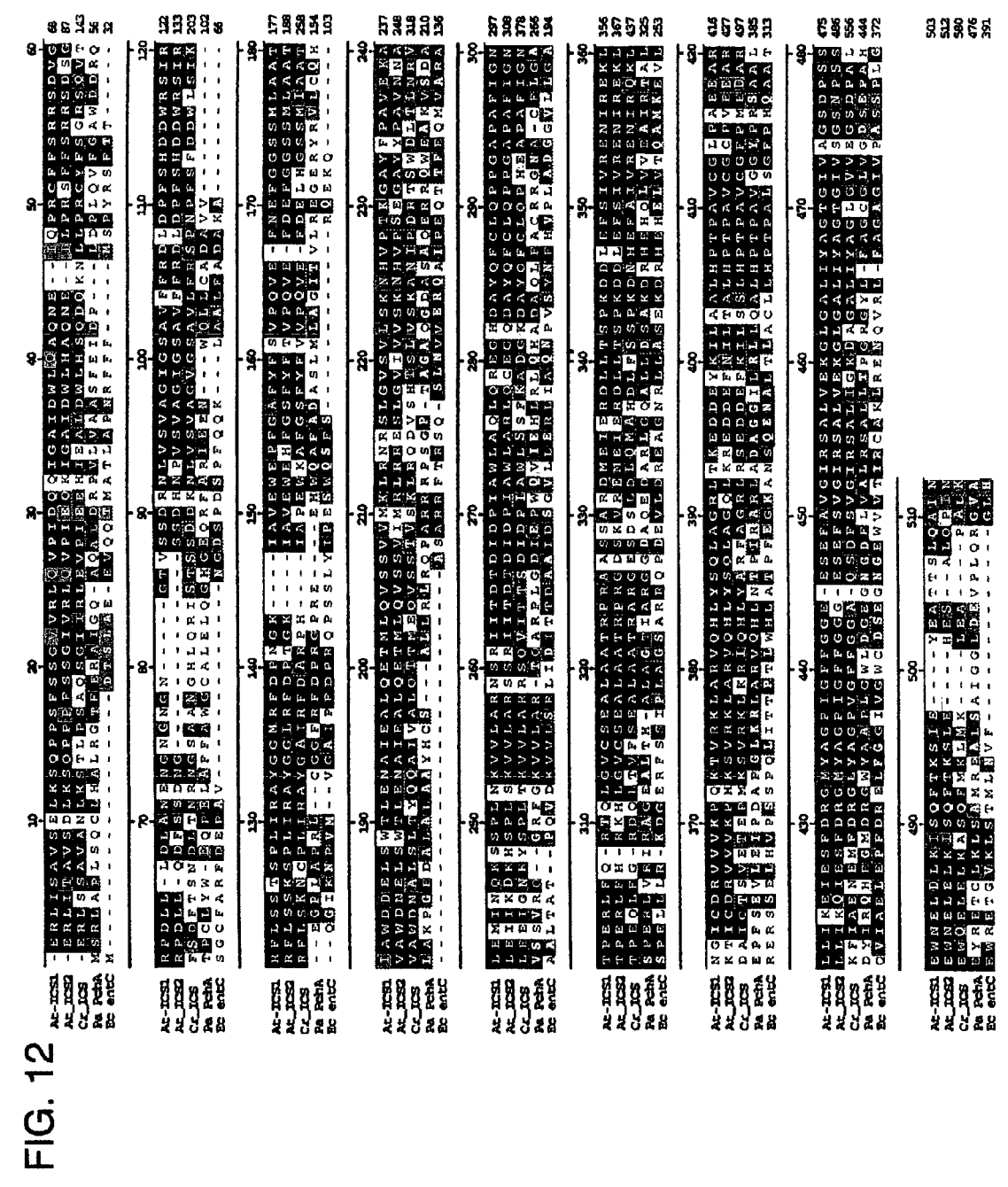

If the product of the pathogen-inducible ICS1 gene is involved in defense-related SA biosynthesis, we reasoned that an Ics1 mutant should exhibit reduced SA accumulation in response to pathogens, reduced PR gene expression, and enhanced susceptibility to pathogens. Two allelic Arabidopsis mutants, sid2-1 (Nawrath & Metraux Plant Cell 11:1393–1404, 1999) and sid2-2/eds16-1 (Dewdney et al., supra) have been identified that exhibit these phenotypes and have been mapped to the bottom of Chromosome I, near the ICS1 locus. To ascertain whether the sid2 mutants contain mutations in ICS1, we first examined the fast neutron-generated sid2-2 mutant. Fast neutron mutagenesis typically causes deletions resulting in loss of transcription of the affected gene. Indeed, ICS1 transcript was not detected in Erysiphe-infected leaves of sid2-2 (FIG. 9A). Specifically, Northern blot analysis of total RNA from Erysiphe-infected (+) and uninfected (−) leaves of sid2-2 was compared to the controls wild type (Columbia) and nahG transgenic Arabidopsis. Moreover, aberrant PCR products were obtained when sid2-2 genomic DNA was amplified using a series of ICS1-specific primers. Specifically, altered products using primers in exon IX of ICS1 suggested that a region of at least 50 nucleotides was affected (data not shown). The presence of a significant deletion/rearrangement in the sid2-2 mutant compared to wild type at exon IX was confirmed by DNA blot analysis (FIG. 8). The unaltered DraI cleavage pattern indicates that this deletion/rearrangement does not extend into the next gene (FIG. 8). These data demonstrate that eds16/sid2-2 encodes ICS and specifically At ICS1. In addition, the genomic DNA encoding At ICS1 was sequenced from the sid2-1 mutant isolated by Nawrath et al. (The Plant Cell 11:1393–1404, 1999). This mutant was shown to be allelic to eds16-1 (sid2-2) based on non-complementation, similar map position, and phenotypes. sid2-2 contains a point mutation of a T instead of an C in exon 8, residue 387 (FIGS. 10 and 12).

Figure 9B:
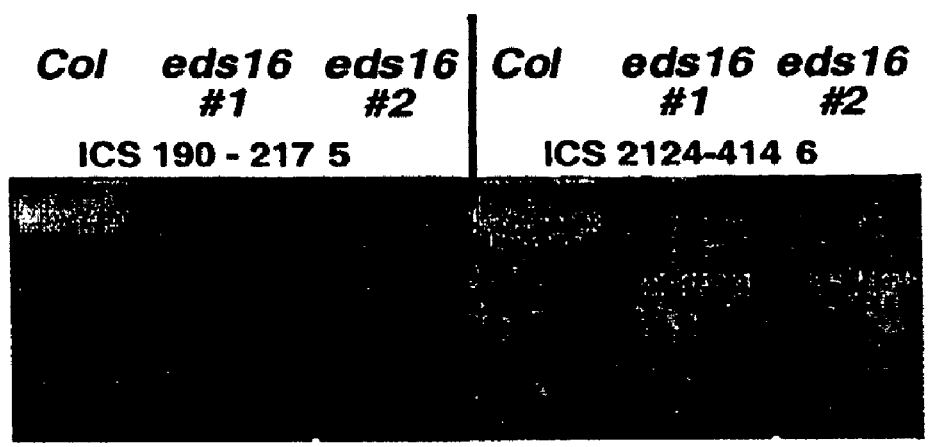
FIG. 9B is a photograph that shows PCR analysis of the ICS gene in eds16 mutants. Two different regions of the ICS gene were amplified from two independent eds16 DNA preparations.

EDS16 Encodes Isochorismate Synthase, an Enzyme in a Novel SA Biosynthetic Pathway As described above, eds16 accumulates significantly reduced levels of SA following pathogen attack, suggesting that eds16 may encode an enzyme in a SA biosynthetic pathway. In thinking about a putative role for EDS16 in SA biosynthesis, we postulated that SA may be synthesized by two independent biosynthetic pathways in plants. We reached this conclusion on the basis of the following observations. First, no *Arabidopsis* mutants have been isolated that mimic transgenic plants expressing nahG. Second, in a variety of labeling studies based on the assumption that SA is synthesized from phenylalanine, the specific activity of SA was considerably lower than expected (see, e.g., Coquoz et al., Plant Physiol. 117:1095–1101, 1998 and Yalpani et al., supra). Third, studies utilizing transgenic *Arabidopsis* plants expressing bacterial nahG (which degrades SA) and experiments in which defense-responses were induced with SA or the SA analogs INA and BTH often resulted in complicated and sometimes conflicting results. Fourth, all of the previous systems used for the study of SA biosynthetic pathway employed incompatible plant-pathogen interactions whereas our screens were carried out using compatible pathogens. In sum, these findings led us to postulate that a second alternate SA biosynthetic pathway existed. We hypothesized that this alternate SA biosynthetic pathway derived from isochorismate, similar to SA biosynthesis in some bacteria (Serino et al., supra). Other plant plastid-localized biosynthetic pathways are derived from bacteria (e.g., plastidic isoprenoid biosynthesis (Lichtenthler, Annu. Rev. Plant Physiol. Plant Mol. Biol. 50:47–65, 1999). The key bacterial enzyme involved in this alternative pathway, isochorismate synthase (ICS), was recently identified in plants (van Tegelen et al., supra). Moreover, a putative *Arabidopsis* ICS homolog is present in the region on chromosome 1 to which we mapped the EDS16 gene using a specially manufactured Affymetrix mapping chip (Cho et al., supra). Because eds16 had been generated by fast neutron mutagenesis, it seemed likely that if EDS16 encoded an *Arabidopsis* ICS homolog, it would be possible to quickly test this hypothesis by RNA blot analysis and PCR of the ICS mRNA and gene, respectively, in eds16. Importantly, as shown in FIG. 9A, the *Arabidopsis* ICS gene is induced in response to *E. orontii* infection in wild type plants, but no ICS mRNA could be detected in eds16. Moreover, as shown in FIG. 9B, aberrant ICS amplification products were obtained using eds16 genomic DNA as template and delimited the area included in the deletion.

Figure 11A:
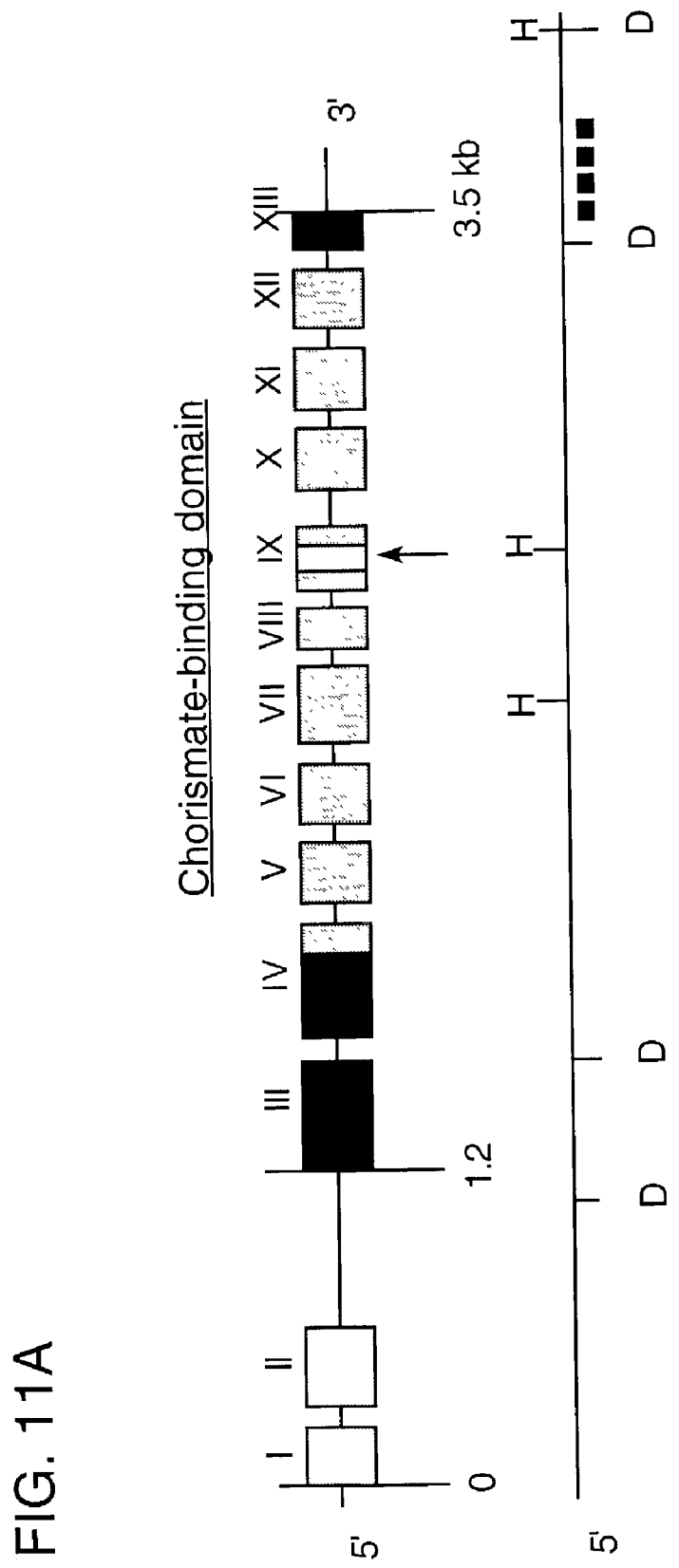
FIG. 11A is a schematic representation of the ICS1 gene that shows the exon structure of ICS1. In the schematic the restriction enzyme digestion sites of ICS1 are HindIII (H) and DraI (D); the dashed line represents the probe used in FIG. 8; sid2-2 is represented by the red box; and sid2-1 is represented by the arrow.
Figure 11B:
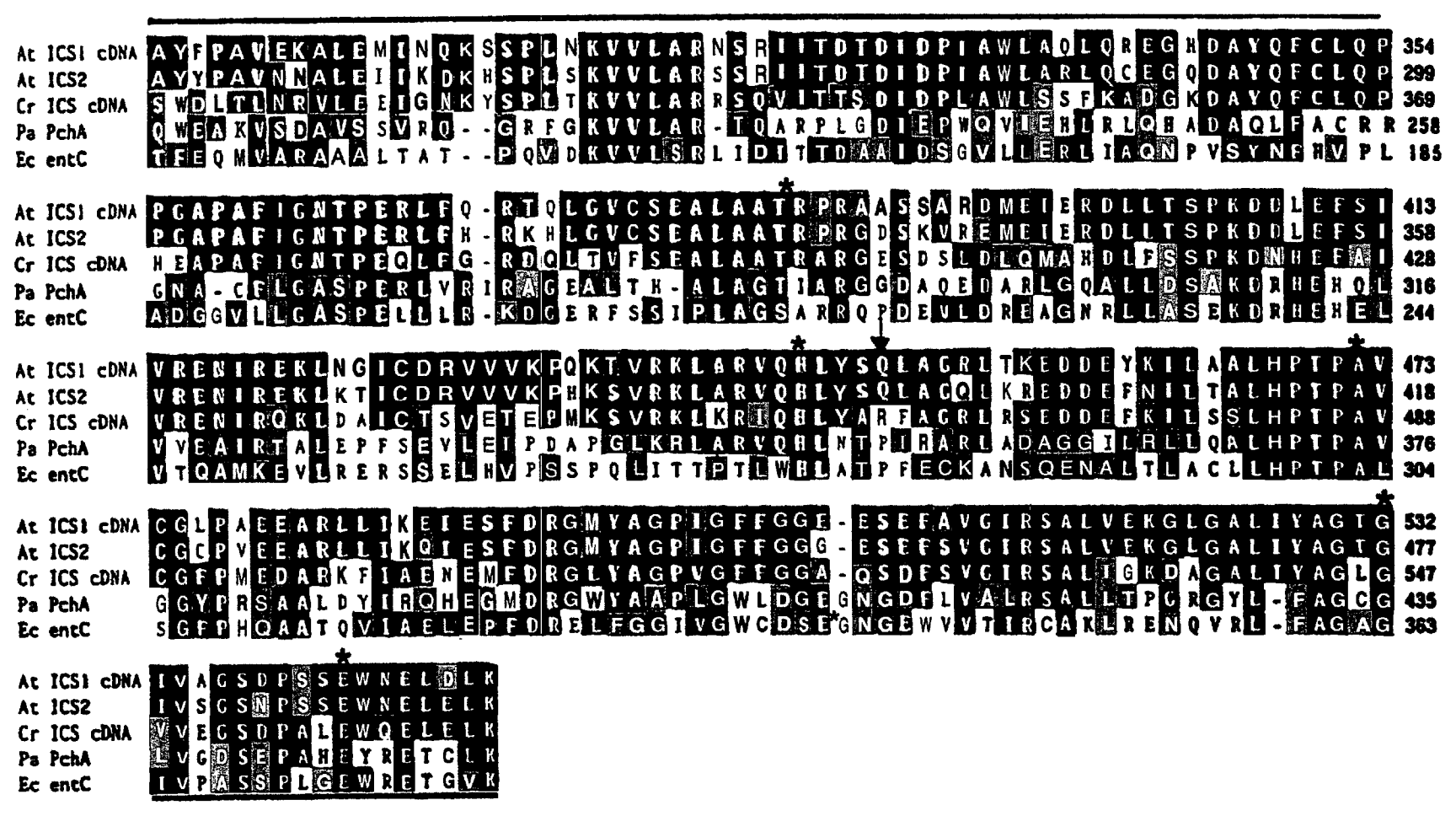

To determine whether sid2-1, an ethylmethane sulfonate-generated mutant, contains a mutation in ICS1, we sequenced ICS1 genomic DNA from sid2-1 and wild type plants. sid2-1 contains a single base pair mutation resulting in a STOP codon in exon IX (FIGS. 11A and 11B). The mutations in both sid2 alleles are predicted to disrupt the function of the highly conserved chorismate-binding domain (FIGS. 11A and 11B). Experiments with additional restriction enzymes and probes gave results consistent with an alteration in this region of exon IX.

Comparison of *Arabidopsis* ICS1 with plant ICS mRNA sequences (SEQ. ID. NO.: 6; (AJ006065 (van Tegelen et al. Plant Physiol. 119:705–712, 1999) and AF078080 (SEQ. ID. NO.: 5) (Meng et al. Plant Physiol. 118:1536, 1998)) revealed that *Arabidopsis* ICS1 likely contains an additional N-terminal extension of ~65 amino acids not reported in GenBank for *Arabidopsis* ICS1. We therefore sequenced *Arabidopsis* ICS1 cDNA isolated using RACE-PCR and confirmed that an extra N-terminal extension is present in ICS1; SEQ. ID. NO.: 16). This extension, absent from bacterial ICS sequences, is characteristic of chloroplast transit sequences and contains a putative cleavage site (FIG. 11A).

Figure 13:
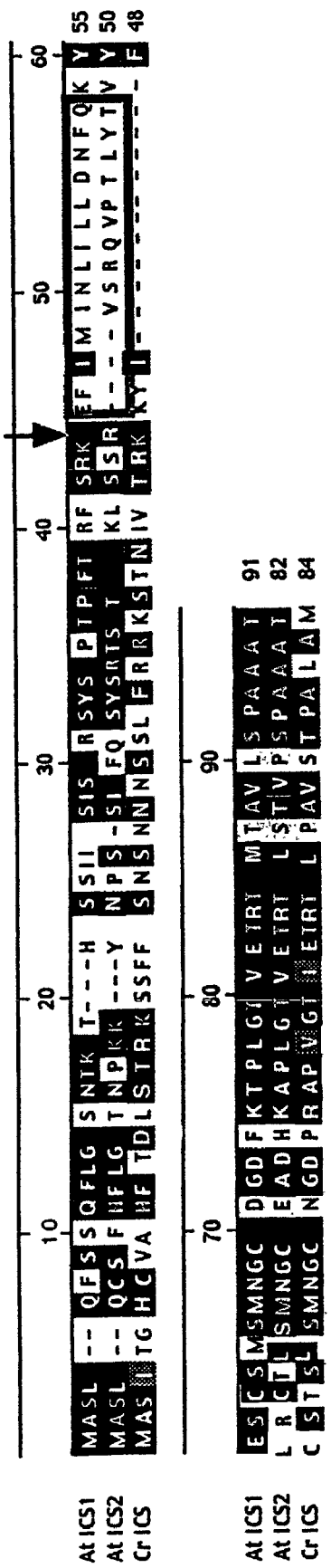
FIG. 13 is an alignment of plant isochorismate N-terminal sequences that include chloroplast transit peptides (SEQ ID NOS: 23, 24, and 25).

We also characterized the N-terminal putative ICS chloroplast transit peptide of At ICS1 by aligning it with transit peptides of At ICS2 and *C. roseus* ICS (FIG. 13). As shown in FIG. 13, the ICS1 gene contains a putative plastid transit sequence and cleavage site consistent with its use of plastid-synthesized chorismate as a substrate. Plastid-localized synthesis of SA mediated by ICS is consistent with the observations that many nuclear-encoded, plastid-localized metabolic pathways derive from prokaryotic endosymbionts. A prokaryotic origin of ICS1 is supported by the presence of an ICS gene in the chloroplast genome of the red algae *Cyanidium caldarium* (NC001840).

Figure 11C:
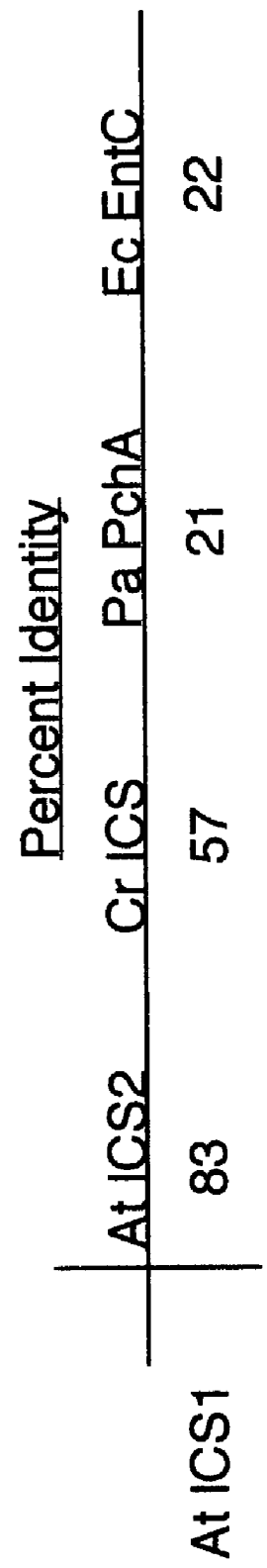
FIG. 11C is a chart that shows the amino acid sequence similarity of protein encoded by *Arabidopsis* ICS1 mRNA and selected isochorismate synthases. N-terminal extensions (putative plastid transit sequences) of plant isochorismate synthases were not included in this analysis. The DNAStar MegAlign Clustal analysis program was utilized. The *Arabidopsis* sequence is compared with *Cr* (*C. roseus*) ICS cDNA (AJ00605; SEQ ID NO: 8), *Pa* (*P. aeruginosa*) PchA (CAA57969; SEQ ID NO: 9), and *Ec* (*E. coli*) EntC (AAA16100; SEQ ID NO: 10).

The C-terminal region of *Arabidopsis* ICS1 contains the highly conserved chorismate-binding domain (FIG. 11B). Residues essential for activity of another chorismate-binding enzyme, anthranilate synthase (Bohlmann et al. Plant J. 7:491–502, 1995), are conserved in ICS1, except that ICS1 has an Ala rather than a Thr residue at position 472 consistent with other ICS sequences. Overall, the *Arabidopsis* ICS1 sequence is 57% identical to an ICS from *Catharanthus roseus* (Madagascar periwinkle) and >20% identical to bacterial isochorismate synthases (FIG. 11C).

Figure 14:
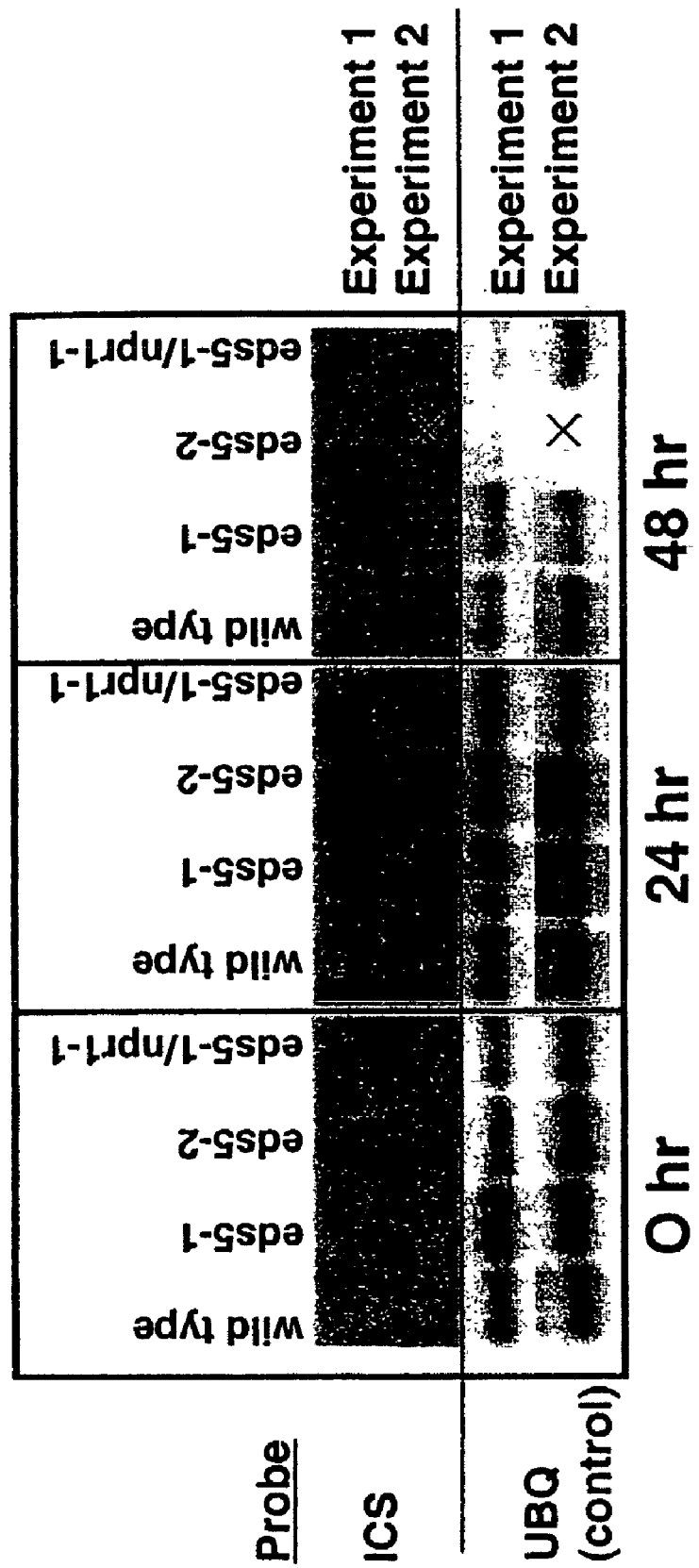
FIG. 14 shows that *Pseudomonas syringae* specifically induces At ICS1. Shown here is the mRNA probed with At ICS1-specific probe derived from the 3' untranslated region of the AT ICS1 mRNA. No At ICS1 gene induction was observed when an At ICS2-specific probe from the 3' untranslated region of At ICS2. The probes were derived from the 3' untranslated regions because the coding sequence of At ICS1 and At ICS2 is highly conserved as shown in FIG. 12.

As noted above, we showed that ICS expression is induced in *Arabidopsis* plants exposed to the pathogen *Erysiphe orontii* (FIG. 9A). Our further studies have shown that other pathogens induce ICS in *Arabidopsis* as well. For example, FIG. 14 shows that ICS was induced in *Arabidopsis* by *Pseudomonas aeroginosa* 4326.

Role of ICS1 and ICS2 in SA Synthesis

Figure 15A:
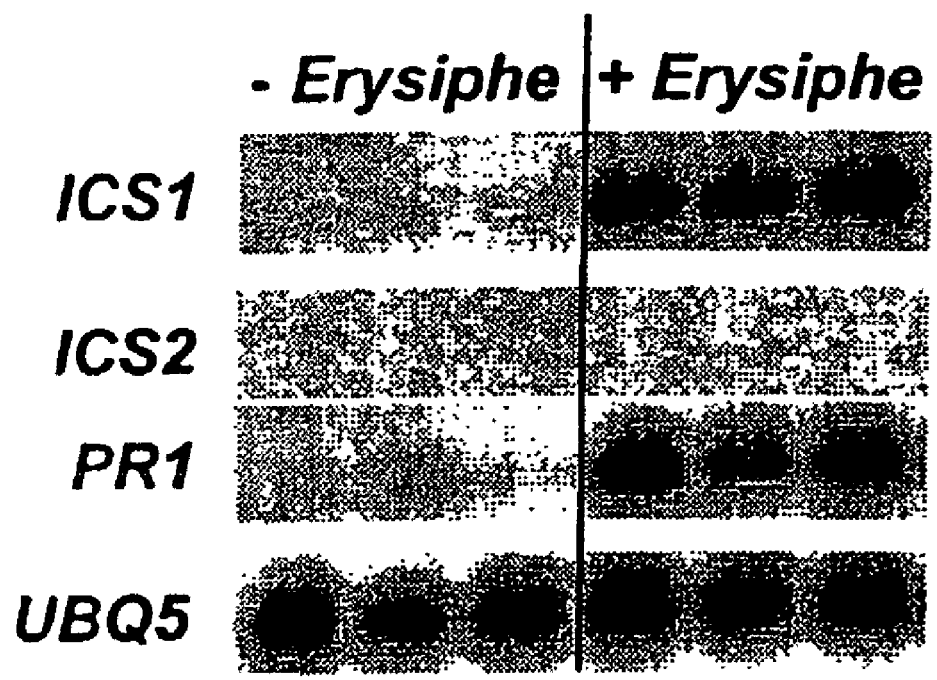
FIG. 15A shows that ICS1 and PR-1 but not ICS2 or UBQ5 RNA expression is induced by Eryisphe infection as measure at 7 dpi. Triplicate samples are shown.
Figure 15B:
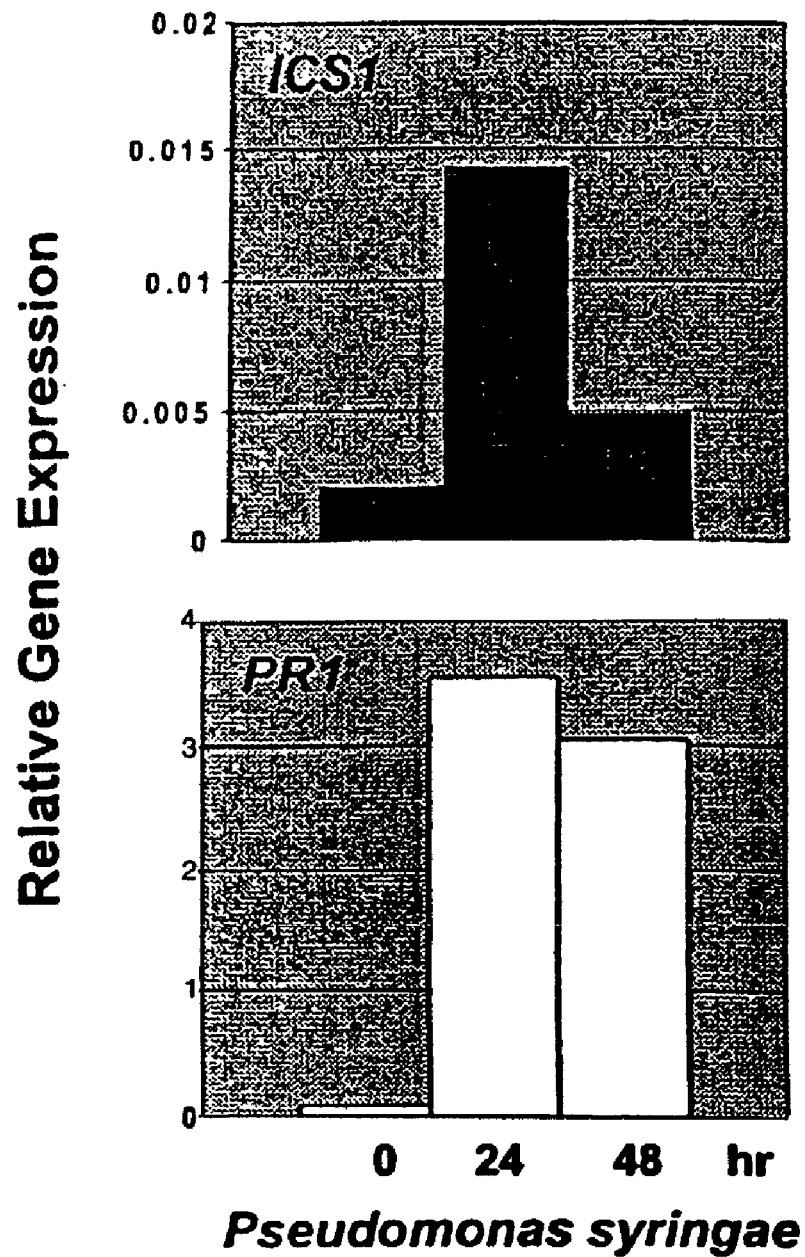
FIG. 15B shows bar graphs of the relative expression of ICS1 and PR1 RNA at 0, 24, and 48 hours after *Pseudomonas syringae* infection.
Figure 17:
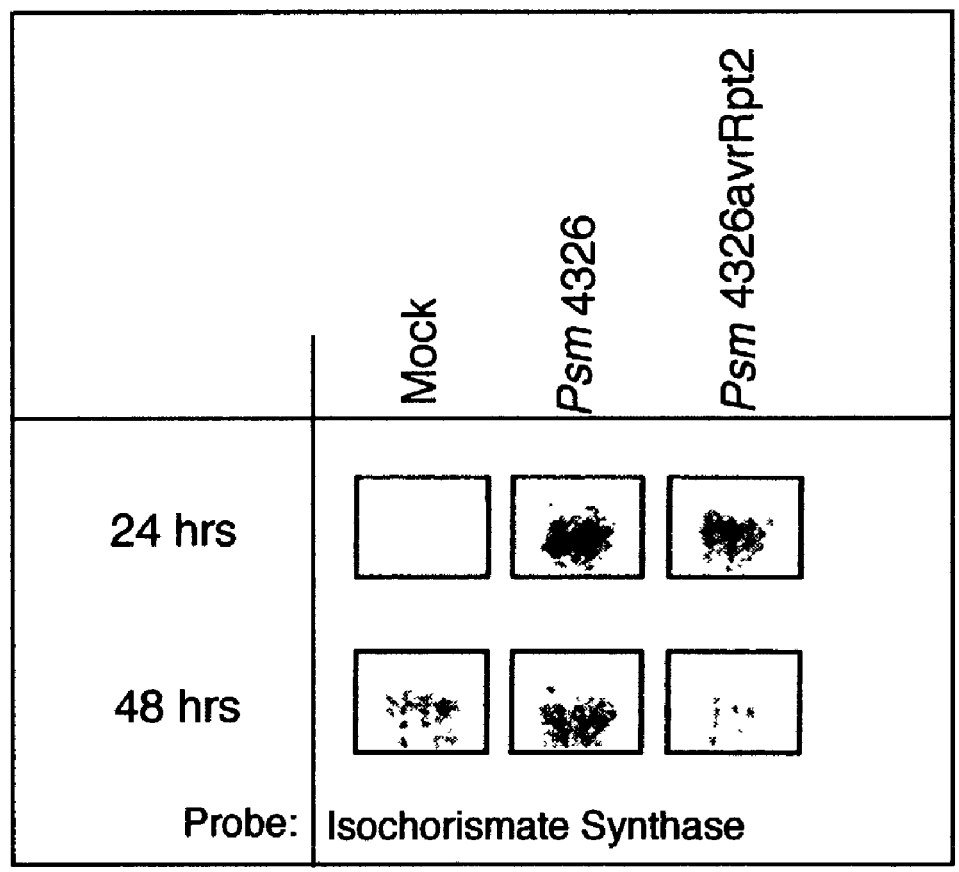
FIG. 17 is an autoradiograph that shows that virulent and avirulent *Pseudomonas syringae* specifically induce At ICS1. *Pseudomonas syringae* pv. *maculicola* avrRpt2 is recognized by an *Arabidopsis* R gene in the Columbia ectoype of *A. thaliana* resulting in the hypersensitive response and systemic acquired resistance.

In *Arabidopsis*, two putative ICS genes, ICS1 and ICS2, are localized to the bottom and top of Chromosome I, respectively. To test the hypothesis that plants utilize ICS to synthesize SA, we first examined whether either *Arabidopsis* ICS gene is induced in response to pathogen treatment. As shown in FIG. 15A, ICS1 expression was induced in leaves infected with the fungal biotroph *Erysiphe orontii* or the bacterial necrotroph *Pseudomonas syringae* pv. *maculicola* (*Psm*). The timing of ICS1 expression is similar to that of SA accumulation in these infected leaves. In addition, when *Arabidopsis* plants were inoculated with an avirulent strain of *Psm* that induces SA accumulation and SAR in systemic leaves, ICS1 was also systemically induced. Similarly, both virulent and avirulent strains of *Pseudomonas*, *Psm* 4326 and *Psm* 4326avrRpt2, induce ICS expression in *Arabidopsis* Col-0 (FIG. 17). A transcript corresponding to ICS2 was not detected in either infected or uninfected *Arabidopsis* leaves (FIG. 15A). We compared the relative expression of ICS1 and PR1 a various times after *Pseudomonas syringae* infection as shown in FIG. 15B. Similar to the findings represented in FIG. 15A, no ICS2 signal was detected. The experiments were performed as in (Dewdney et al., Plant J. 24:205–218, 2000). ICS1 and ICS2-specific primers correspond to the 3'-untranslated region. Forward and reverse primers used to make the ICS probe templates and probes are as follows:

ICS1F: GGGGATAAGGGGTTCTCACAATA (SEQ. ID. NO.: 11),
ICS1R: CTGCCCTAGTTACAACCCGAAAAG (SEQ. ID. NO.: 12),
ICS2F: TGTGTTTGGTCATTGGTGT (SEQ. ID. NO.: 13),
ICS2R: TCATAGAGTCATAGTCGCTTCA (SEQ. ID. NO.: 14).

Figure 16A:
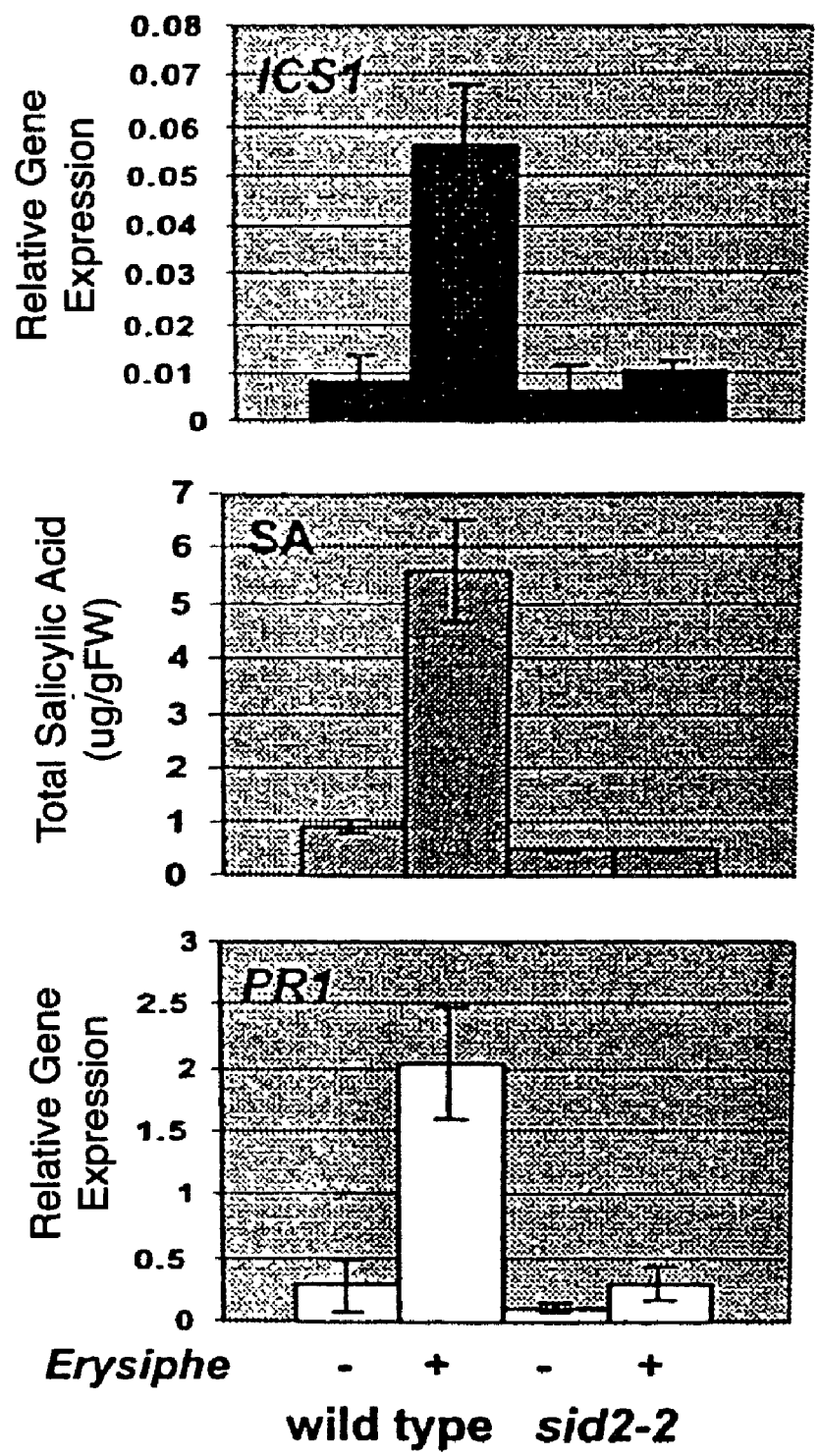
FIG. 16A are bar graphs that show the relative gene expression of ICS1 and PR1 and SA accumulation in wild type or sid2-2 after infection by Erysiphe at 7 dpi.

In *Arabidopsis*, the addition of SA is sufficient to induce SAR and the removal of SA by the bacterial transgene nahG abolishes SAR (Dempsey et al. Crit. Rev. Plant Sci. 18:547–575, 1999 and Ryals et al. Plant Cell 8:1809–1819, 1996). In sid2 mutants, total SA accumulation in response to the virulent biotroph *Erysiphe* or avirulent strains of *Pseudomonas syringae* is ~5–10% of wild type (Nawrath et al., supra and Dewdney et al., supra) and similar in magnitude to that of uninfected plants (FIG. 16A). In FIG. 16A, ICS1, total SA (free and sugar conjugated SA) levels, and PR1 gene expression were measured in wild type and sid2-2 plants infected or not infected with *Erysiphe* at 7 dpi. In addition, the pathogenesis related gene PR1, which is considered to be the most robust molecular marker of SAR in *Arabidopsis* (Uknes et al. Mol. Plant Microbe Interact. 6:692–698, 1993 and Maleck et al. Nature Genetics 26:403–410, 2000), is induced at very low levels in sid2 mutants, ~1–10% of wild type (Nawrath et al., supra and Dewdney et al., supra; FIG. 16A). Consistent with these observations, sid2 mutants do not exhibit SAR in systemic leaves when infected with an avirulent pathogen (Nawrath et al., supra) or induction of SAR-like responses in leaves infected with the fungal biotroph *Erysiphe* (Dewdney et al, supra). These results suggest that SA synthesized using ICS1 is required for *Arabidopsis* SAR defense responses.

Genetic analyses identified NPR1/NIM1 (Cao et al. Plant Cell 6:1583–1592, 1994 and Delaney et al. Proc. Natl. Acad. Sci. USA 92:6602–6606, 1995) as a requisite regulator of SAR that acts downstream of SA. NPR1/NIM1 interacts with transcription factors to alter the expression of genes (such as PR1) in response to pathogen attack (Despres et al. Plant Cell 12:279–290, 2000). FIG. 16B indicates that ICS1 acts upstream of NPR1/NIM1 as ICS1 mRNA is still expressed in the npr1 mutant, consistent with SA accumulation via ICS1 acting upstream of NPR1. Relative total SA (free and sugar conjugated SA) levels and ICS1 and PR1 gene expression levels in mutant or transgenic *Arabidopsis* were compared to wild type plants. ICS1 and PR1 expression were assessed by Northern blot analysis of total RNA infected with *Erysiphe*. Northern blot analysis was performed and quantified as in FIGS. 15A and 15B. SA extraction and HPLC analysis was performed as in (Dewdney et al., supra). *Arabidopsis* mutants and transgenics are in Columbia ecotype. cpr mutant data is from 4 week old plants. The nahG transgenic *Arabidopsis* line is described in (Asai et al. Plant Cell 12:1823–1839, 2000). Infection with *Psm* ES4326 ($OD_{600}$=0.002, 24 hpi) gave similar results. Relative PR1 expression agreed with reported values (Nawrath et al., supra, Dewdney et al., supra, Cao et al., supra, Delaney et al., supra, Bowling et al., 1994, Bowling et al., 1997, and Clarke et al., supra). Total SA levels are compiled from new data (sid2 (FIG. 16A) and nahG (FIG. 8 and data not shown)) and published work values (Nawrath et al., supra, Dewdney et al., supra, Delaney et al., supra, Bowling et al., 1994, Bowling et al., 1997, and Clarke et al., supra). Our data also supports a role for NPR1 as a negative feedback regulator of ICS1 expression and SA accumulation. This role for NPR1 was first proposed when elevated SA levels were observed in infected leaves of npr1/nim1 plants (Delaney et al., supra). We found that ICS1 expression was also elevated in infected leaves of npr1 plants (FIG. 16B).

We were also interested in determining whether SA regulates the expression of ICS1. nahG transgenic plants convert SA to catechol; they do not accumulate SA, express little PR1 in response to pathogen, and do not exhibit SAR (Dempsey et al., supra and et al., supra). Importantly, ICS1 expression was not altered in nahG transgenic plants (FIGS. 9A and 16B). The simplest interpretation of this result is that SA alone is not required for the induction or repression of ICS1 expression and hence there is no direct autoregulation. To further support the conclusion that SA synthesized via ICS1 mediates SAR, we examined ICS1 (and PR1 expression) in the *Arabidopsis* cpr mutants (cpr1 (Bowling et al. Plant Cell 6:1845–1857, 1994), cpr5 (Bowling et al. Plant Cell 9:1573–1584, 1997), and cpr6 (Clarke et al. Plant Cell 10:557–569, 1998)) which exhibit constitutively elevated SA levels, PR1 expression, and SAR. As anticipated, ICS1 is constitutively expressed in the cpr mutants (FIG. 16B).

Figure 16C:
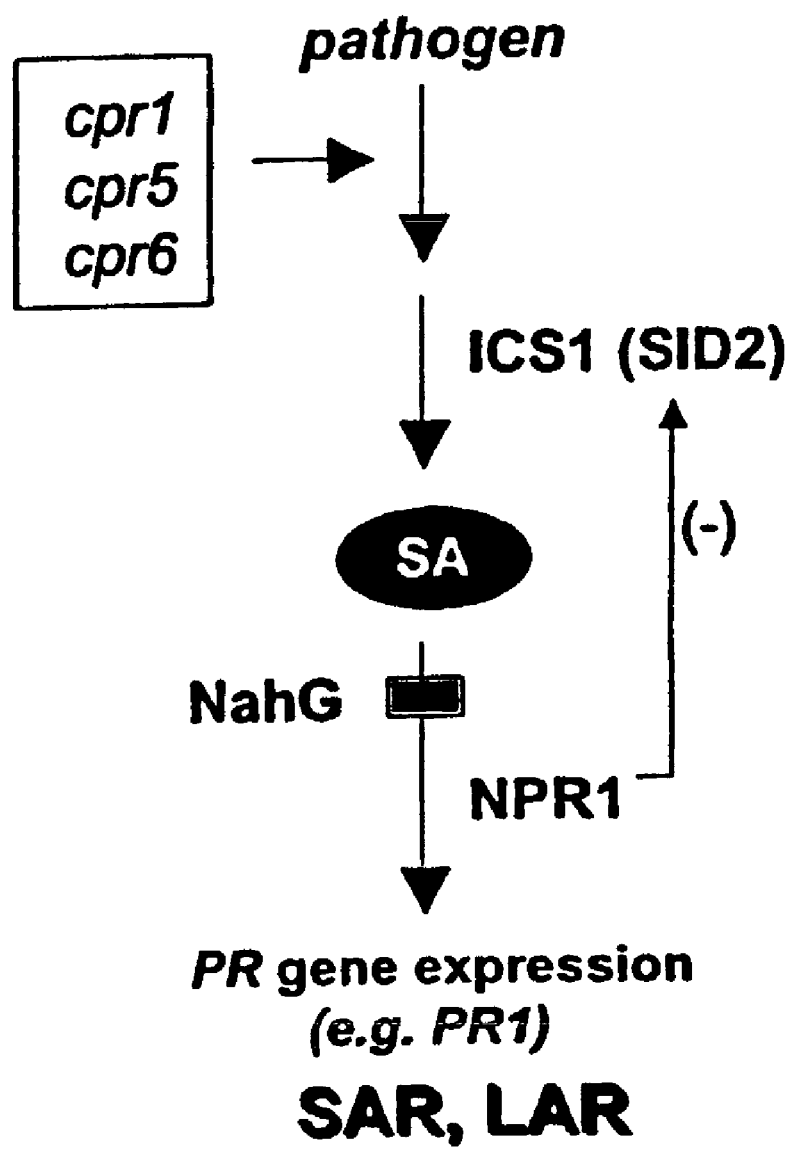
FIG. 16C is a schematic that depicts the proposed placement of ICS1 in SAR induction based on results tabulated in FIG. 16B.

FIG. 16C presents a model depicting the placement of ICS1 in SAR induction in *Arabidopsis*. The cpr mutants likely function upstream of ICS1 expression and SA accumulation. ICS1 expression is upstream of SA accumulation as sid2 mutants accumulate little SA and nahG transgenics, which degrade SA, still express ICS1. npr1 mutants have elevated SA and ICS1 expression in response to pathogen. Therefore, in addition to its role as a regulator of PR gene expression, NPR1, or some effector downstream of NPR1, may also act to negatively regulate ICS1 and SA accumulation. The SA-dependent, NPR1-independent component of LAR/SAR is not explicitly shown. However, as PR1 mRNA levels are lower in leaves of *Erysiphe*-infected sid2 than in npr1 mutants, ICS1 likely participates in SA-mediated npr1-dependent and -independent pathways.

Figure 16D:
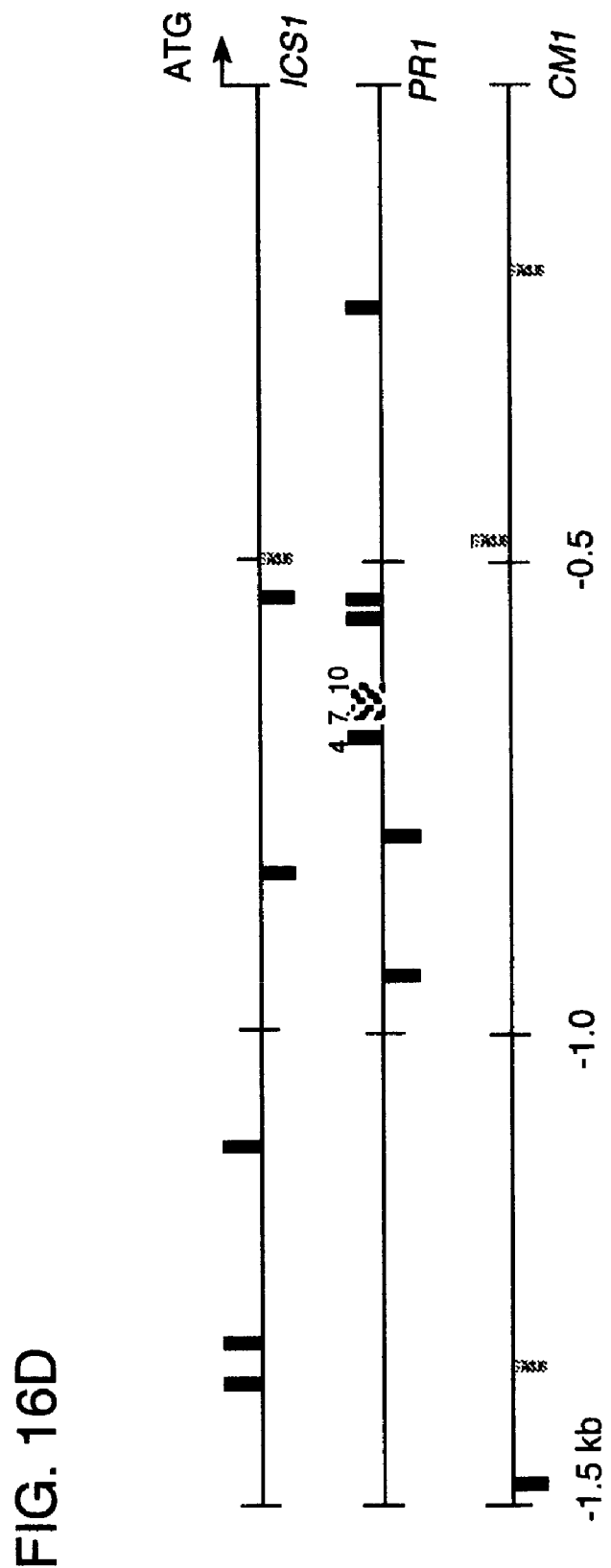
FIG. 16D is a schematic that depicts the cis-acting DNA regulatory elemts 1.5 kb upstream of translation start site of ICS1, compared with PR1, and CMI (chorimate mutase).

Because our results indicate that SA synthesized via ICS1 acts upstream of NPR1/NIM1 in the induction of SAR, we analyzed the ICS1 promoter for known cis-acting regulatory elements associated with defense responses in plants (FIG. 16D and Table 4 below). We were therefore surprised to find that the ICS1 promoter is enriched in W-box elements similar to promoters of genes in the SAR regulon such as PR1 (Maleck et al., supra). As shown in FIG. 16D, the cis-acting DNA regulatory elements 1.5 kb upstream of translation start of ICS1, compared with PR1, and CM1 (chorismate mutase) reveal 1) the W-box core (TTGAC) or extended core (TTGAC(C/T)) (Black box; Euglem et al. supra); 2) the Myb-binding site (MBS) II consensus (G(G/T)T(A/T)G(G/T)T) (gray box; Yang et al., supra); 3) the 2,6-dichloroisonicotinic acid-inducible (INA; SA analog) elements in linker scanning (LS) regions LS10 (NF-kB: GGACTTTTC) or LS7 (bZIP: ACGTCA) of the PR1 promoter (hatched box; Lebel et al., supra). The LS4 region (containing a W-box) negatively regulates INA-inducible expression of PR1. Box above line represent elements found on forward (becomes the coding) strand. Further details are provided in Table 4.

TABLE 4

Sequence and position of notable cis- acting elements present in the promoters of Arabidopsis ICS1, PR1, and CM1

| GENE | MOTIF | SEQUENCE | Begin (−) | End (−) |
|------|-------|----------|-----------|---------|
| ICS1 | ERELEE4[1] | tttgaatt | 1106 | 1099 |
| ICS1 | MYBII[2] | accaac | 493 | 487 |
| ICS1 | WRKYcore[3] | gtcaa | 543 | 539 |
| ICS1 | WRKYextcore | gtcaa | 823 | 819 |
| ICS1 | WRKYextcore[3] | ttgacc | 1157 | 1152 |
| ICS1 | WRKYextcore | ttgact | 1348 | 1343 |
| ICS1 | WRKYcore | ttgact | 1393 | 1388 |
| CM1 | ERELEE4 | atttcaaa | 1349 | 1342 |
| CM1 | MYBII | acctacc | 133 | 127 |
| CM1 | MYBII | ggtagtt | 453 | 447 |
| CM1 | MYBII | aacaacc | 1371 | 1365 |
| CM1 | WRKYcore | gtcaa | 1462 | 1458 |
| PR1 | BZIP[4] | acgtca | 681 | 676 |
| PR1 | BZIP | acgtca | 698 | 693 |
| PR1 | ERELEE4 | tttgaaat | 414 | 407 |
| PR1 | ERELEE4 | aattcaaa | 422 | 415 |
| PR1 | NF-kB[4] | ggactttc | 650 | 642 |
| PR1 | WRKYcore | ttgac | 217 | 213 |
| PR1 | WRKYextcore | ttgact | 554 | 549 |
| PR1 | WRKYextcore | ttgact | 580 | 575 |
| PR1 | WRKYextcore | ttgact | 712 | 707 |

TABLE 4-continued

Sequence and position of notable cis- acting elements present in the promoters of Arabidopsis ICS1, PR1, and CM1

| GENE | MOTIF | SEQUENCE | Begin (−) | End (−) |
|------|-------|----------|-----------|---------|
| PR1 | WRKYcore | gtcaa | 783 | 779 |
| PR1 | WRKYextcore | agtcaa | 929 | 924 |

Genomic sequence corresponding to 1.5 kb upstream of the predicted translation start codon (ATG) were analyzed for the presence of known cis-acting elements.
Elements within the first 1.5 kb have been shown to modulate expression in plants (e.g. GST1 of carnation, in (1)).
Numbering is relative to the translation start for each gene.
GenbankAccession numbers: ICS1 (AC011765), PR1 (AF096294), CM1 (AJ242647).
[1]Itxhaki, H., Maxson, J. M., & Woodson, W. R. An ethylene-responsive enhancer element is involved in the senescence-related expression of the carnation glutathione-S-transferase (GST1) gene. Proc. Natl. Acad. Sci. USA 91, 8925–8929 (1994).
[2]Yang, Y. & Klessig, D. F. Isolation and characterization of a tobacco mosaic virus-inducible myb oncogene homolog from tobacco. Proc. Natl. Acad. Sci. USA 93, 14972–14977 (1996).
[3]Eulgem, T., Rushton, P. J., Robatzek, S. & Somssich, I. E. The WRKY superfamily of plant transcription factors. Trends Plant Sci. 5, 199–206 (2000).
[4]Lebel, E. et al. Functional analysis of regulatory sequences controlling PR-1 gene expressin in Arabidopsis. Plant J. 16, 223–233 (1998).

Reported in Table 4 (above) are those cis-acting elements most likely to be relevant to defense-related expression of ICS1 (SEQ ID NOS: 4 and 15). Analysis was performed using i) a pattern matching program PromoterScan, ii) PLACE SignalScan Higo et al., *Nucleic Acids Research* 27:297–300, 1999), and iii) PlantCARE Search for CARE Rombauts et al., *Nucleic Acids Res.* 27: 295–296, 1999). In addition, we used Alibaba2 Grabe, In Silico Biol. 1 (2000)) to search for possible plant variants of the NF-kB binding element. Motifs examined were known cis-acting elements reported in the literature as being involved in defense (e.g. above and in (Maleck, K. et al., *Nature gentics* 26:403–4 10, 2000)) and those in the PLACE and PlantCARE databases. Using Alibaba2, no NF-kB-like element was discovered in the iCS1 promoter; however, the NF-kB-like element in the promoter of PR1 was confirmed. The ethylene responsive element ERELEE4 (consensus sequence: A(A/T)TTCAAA) was also studied. It is involved in the senescence-related expression of carnation glutatione-S-transferase (GST; Itxhaki et al., Proc. Natl. Acad. Sci. USA 91:8925–8929, 1994). GSTs and many genes associated with senescence are part of the SAR regulon (Maleck, K. et al., *Nature Genetics* 26:403–410, 2000). W-boxes are recognized by WRKY plant-specific transcription factors that regulate pathogen and stress responses (Eulgem et al. Trends Plant Sci. 5:199–206, 2000). One explanation consistent with an enrichment of W-box elements in both the promoters of ICS1 and genes downstream of ICS1 and SA accumulation such as PR1 is that different WRKY factors regulate these responses. Reports of a variety of early- and late-acting WRKY factors activated by SA, elicitors, and/or pathogens support this view (Id). Alternatively, shared WRKY factor(s) may suppress both ICS1 and PR1 expression. The location of a W-box element in a region (LS4) shown to negatively regulate PR1 expression in response to a SA analog (Lebel et al. Plant J. 16:223–233, 1998) is consistent with this explanation.

Although the ICS1 promoter is enriched in W-box elements, it does not contain the cis-acting regulatory elements in linker scanning (LS) region 7 (bZip motif) or LS10 (NF-κB motif) required for the induction of PR1 by SA (Id.). This is consistent with our observation that ICS1 expression was not affected by SA levels (FIG. 16C) and supports the hypothesis that a systemic signal other than SA is required for ICS1 induction, SA accumulation, and SAR (Vernooij et al. Plant Cell 6:959–965, 1994). Another feature distinguishing the ICS1 and PR1 promoters is that ICS1 contains a Myb binding site (MBSII) at a position (∼−500 bp) similar to that of the other inducible chorismate-utilizing enzymes, CM1 (FIG. 16D) and ASA1 (data not shown). Myb factors play a role in SA-mediated plant defenses (e.g. Myb1; Yang et al., Proc. Natl. Acad. Sci. USA 93:14972–14977, 1996) and in the regulation of secondary metabolism including modulation of pathogen-inducible ASA1 expression (Bender et al., supra). As the chorismate-utilizing enzymes are critical control points of pathways resulting in a myriad of defensive compounds (see FIG. 1), it is highly likely that ICS1 expression is regulated by a Myb factor(s).

Isolation and Characterization of Mutants

Multiple factors determine the outcome of attempted pathogen infection of a plant. Defense responses, including expression of PR genes and formation of cell wall appositions, are critical in limiting infection. Biotrophic pathogens may require specific host susceptibility factors for development and colonization. Additionally, other aspects of the host environment, such as nutrient content, may influence growth of a biotrophic pathogen. Therefore, mutants that support enhanced growth of a biotrophic pathogen may be different from wild type in any of these traits. In a screen for mutants that have enhanced susceptibility to *E. orontii*, we isolated both new alleles of genes that have previously been shown to function in defense response pathways (pad4 and sid2) and novel genes (eds14 and eds15) that have a role in defense. Nine mutants that were identified in the screen have not been sufficiently characterized to determine whether they are defense-related or affect other traits that influence the outcome of an interaction with a biotrophic pathogen. Although the three mutants, eds14, eds15, and sid2/eds16, described in detail in this work are all aberrant in some aspect of defense responses, each of them has a unique phenotype (summarized in Table 3).

In sid2/eds16, the loss of PR-1 induction indicates that this mutation affects the salicylic acid signal transduction pathway, since all induction of PR-1 during a compatible interaction with *E. orontii* occurs via an SA-dependent pathway (Reuber et al., supra). Furthermore, the low SA levels and the ability of sid2/eds16 to respond to exogenous SA suggest that the sid2/eds16 product functions upstream of SA. The level of BGL2 and PR-5 expression in infected sid2/eds16 leaves is similar to the portion of induction of these PR genes that previous studies indicated was SA-independent (Reuber et al., supra).

Similarly, eds15 appears to act upstream of SA, as it fails to accumulate wild type levels of PR-1 mRNA and salicylic acid. The resemblance between eds15 and eds16 suggests that both may function in the same pathway, with eds15 having a less critical role. However, in eds15 the attenuation of BGL2 and PR-5 expression is almost as great as in eds16, while there are large differences between the two mutants in PR-1 induction. eds14 is unusual in several aspects. First, it is more susceptible despite accumulating PR-1 mRNA to higher levels than in wild type. One possible explanation for the increase in PR-1 mRNA accumulation is that more cells are infected in eds14 than in wild type plants. However, we do not favor this interpretation because levels of the signaling compound that is required for PR-1 induction, salicylic acid, are reduced in eds14 relative to wild type. This is the second unusual feature of eds14, namely, that PR-1 induction appears to be uncoupled from both SA accumulation and from induction of BGL2 and PR-5.

Role of SA in Response to *E. orontii* Infection

The isolation of eds14, eds15, and sid2/eds16 reinforces the theory that SA signaling has a critical role in limiting *E. orontii* growth, as was previously suggested by Reuber et al. (The Plant Journal 16:473–485, 1998). pad4, eds5, npr1, and NahG plants are all deficient in SA signal transduction (Cao et al., supra; Gaffney et al., supra; Nawrath et al., supra; and Zhou et al., supra) and are all more susceptible to *E. orontii* (Reuber et al., supra). In pad4, eds5, NahG, eds15, and sid2/eds16, the accumulation of SA is attenuated, whereas npr1 fails to activate responses downstream of SA. As a result of SA signaling deficiencies, the production of PR-1 mRNA in these lines is reduced. Several studies have shown that PR-1 has antifungal activity (Niderman et al., Plant Physiology 108:17–27, 1995; and Rauscher et al., The Plant Journal 19:625–633, 1999) and can associate with fungal cell walls (Cordier et al., MPMI 11:1017–1028, 1998). On the other hand, the phenotype of eds14 indicates that PR-1, although it may be an important defense against *E. orontii*, is not the only determinant of susceptibility. However, the importance of SA-mediated defenses is not refuted by this mutant, as SA concentrations in infected eds14 leaves are lower than in infected wild type plants, in contrast to PR-1 levels being higher.

Role of JA/ethylene Pathways in Response to *E. orontii*

In sid2/eds16, but not wild type, PDF1.2 is induced by *E. orontii* infection. Therefore, there must be a mechanism by which *E. orontii* activates the JA/ethylene signaling pathway, which was not apparent from previous studies. A second implication is that PDF1.2 is only induced when SA levels are low, suggesting that there is suppression of the JA/ethylene signaling pathway by SA. Similar antagonistic effects have been reported by other groups. PDF1.2 expression is higher in NahG plants than in wild type (Penninckx et al., 1996), and PDF1.2 mRNA accumulation is higher in the mutant ssi1 in the absence of functional NPR1 (Shah et al., The Plant Cell 11:191–206, 1999). In addition, the biosynthesis of both jasmonic acid and ethylene are reportedly inhibited by exogenous acetyl salicylate and SA, respectively (Leslie et al., Plant Physiology 88:833–837, 1988 and Peña-Cortés et al., Planta 191:123–128, 1993). On the other hand, there is also evidence for synergistic interactions between the two pathways. Ethylene may potentiate SA-mediated induction of PR-1 (Lawton et al., MPMI 8:863–870, 1995; Lawton et al., The Plant Cell 6:581–588, 1994; and Xu et al., The Plant Cell 6:1077–1085, 1994) and there are at least two reports of genes (EREBP1 in tobacco and an ACC oxidase gene in *Nicotiana glutinosa*) that are inducible by both SA and ethylene (Horvath et al., supra and Kim et al., Plant & Cell Physiology 39:565–573, 1998).

Intimations of an Additional Defense Response Pathway

Loss of suppression could also be the basis for the elevated levels of PR-1 in eds14. However, BGL2 and PR-5, which are induced via both SA-dependent and SA-independent pathways (Reuber et al., supra), are not hyperinduced, so it seems unlikely that the eds14 mutation results in inactivation of a pathway or compound that normally inhibits the SA signaling pathway. Alternatively, there might be limitations on PR-1, but not BGL2 or PR-5, expression that are released in eds14. Because the JA/ethylene pathway does not seem to be activated during *E. orontii* infection unless SA concentrations are abnormally low, it is unlikely that it is the source of this hypothesized inhibition. The existence of an additional defense response pathway has been suggested by the isolation of the pmr3 mutant (Vogel et al., Proc. Natl. Acad. Sci. U.S.A. 97:1897–1902, 2000). In this mutant, which is more resistant to *E. cichoracearum* and *E. orontii*, PR-1 expression is suppressed (Vogel et al., Proc. Natl. Acad. Sci. U.S.A. 97:1897–1902, 2000). The lesion in eds14 may lie in this pathway, but have the opposite effect of the pmr3 mutation, that is, increased susceptibility and elevated PR-1.

Salicylic Acid and the Hypersensitive Response

There are conflicting reports about the requirement for SA in the hypersensitive response (Glazebrook, 1999, Lam et al., Current Opinion in Plant Biology 2:502–507, 1999; and Rate et al., The Plant Cell 11:1695–1708, 1999). Although SA levels are severely reduced in sid2/eds16, it is still capable of producing an HR. In this work, we have only measured SA in leaves infected with a virulent pathogen, but data from Nawrath and Metraux on the sid2-1 mutant indicate that SA levels are also low during an incompatible interaction (Nawrath et al., supra. However, in both our experiments and those reported by Nawrath and Métraux, SA was not measured until 2 dpi (Id.) or 7 dpi. In other work, avirulent pathogens have been shown to trigger a rapid and transient rise in SA, beginning as early as 1 hpi, in addition to a later, more sustained increase (reviewed in Draper, supra). This avr stimulated early increase in SA may not be attenuated in sid2/eds16. It is logical to think that the same determinants of recognition of a virulent pathogen are also present during interaction with an isogenic avirulent pathogen, and that the response to an avirulent pathogen is a combination of R-avr gene mediated responses and responses that would be stimulated by the corresponding virulent pathogen. Both may contribute to limitations on pathogen growth. In the sid2/eds16 mutant, only the second pathway may be altered, causing increased susceptibility to a virulent pathogen but leaving R-avr gene mediated resistance intact. According to this model, the phenotype of sid2/eds16 is not inconsistent with SA being required for the HR.

Specificity of Mutations on Susceptibility to Various Pathogens

Are the lesions in eds14, eds15, and sid2/eds16 specific to interactions with a biotrophic fungal pathogen? For sid2/eds16, the answer is clearly no, as growth of Psm is also less restricted, although the significance of this difference varied among experiments. Similarly, eds14 allows more growth of Psm, although in this mutant the effect on Psm growth is minor, while the effects on *Erysiphe* species are significant. There is some inconsistency in the data for eds15, which indicates that restrictions on growth are slightly relaxed for Psm, but not for *E. cichoracearum*, which is closely related to *E. orontii*. It may be that the phenotype of eds15 is not strong enough for differences in growth of *E. cichoracearum* to be apparent, whereas the assay used to quantify Psm growth may be more sensitive to small variations. None of the mutants is more susceptible to the necrotrophic fungal pathogen *B. cinerea*.

In summary, the lesions in all three mutants affect defenses against more than one class of pathogen, but susceptibility to different pathogens is enhanced to different extents. The unique phenotype of each of the mutants described herein indicates that each can provide new information about the controls that govern plant defense responses and about the defenses that are effective in limiting growth of specific pathogens.

The experimental results described above were obtained using the following experimental methods.

Experimental Methods

Growth of *Arabidopsis thaliana*

For most experiments, *Arabidopsis* plants were grown in Metro-Mix 200 (Scotts-Sierra Horticultural Products Co., Marysville, Ohio, U.S.A.) under a 12 hour light-dark cycle either in a greenhouse with supplemental fluorescent lighting (19±2° C.) or in a Percival AR-601 growth chamber (20° C., 80% relative humidity, illumination approximately 100 µE m$^{-2}$ s$^{-1}$). For assays of *E. cichoracearum* susceptibility, plants were grown in Levington Multipurpose compost (Ipswich, U.K.) in growth chambers with an 8 hour photoperiod (150 µE m$^{-2}$ s$^{-1}$) and a temperature of 22° C. *Arabidopsis* accession Col-0 was obtained from G. Redei (*Arabidopsis* Information Service). EMS and fast neutron mutagenized seed were obtained from Lehle Seeds, P.O. Box 2366, Round Rock, Tex.

To create backcrossed lines, the mutants were crossed to the parental line Col-0 and the F2 progeny were scored for *E. orontii* susceptibility. F3 families from F2 progeny with an eds phenotype were scored to confirm that the F2s were homozygous for the eds mutation. All experiments were performed at least once in the backcrossed lines, though some experiments were done first with M4 progeny and repeated in the backcrossed lines.

Fungal, Oomycete, and Bacterial Inoculations

*E. orontii* inoculations were done as described in Reuber et al., supra, except that all inoculations for experiments were done using a settling tower. For scoring susceptibility, a light inoculum (conidia from one infected leaf) was used per 206 cm$^2$ box of plants. A heavier inoculum (conidia from 3 infected leaves) was used for analysis of defense-related gene expression. *E. cichoracearum* was propagated as described in Vogel et al., Proc. Natl. Acad. Sci. U.S.A. 97:1897–1902, 2000. *Arabidopsis* plants were inoculated by dusting with conidia from 10–12 day old *E. cichoracearum* cultures. *B. cinerea* was isolated from cabbage and cultured on potato dextrose agar (Sigma) with a long photoperiod (16 hours of light). Spores were harvested from 9 to 10 day old cultures by flooding the plates with sterile water and centrifuging the suspension at 5000 rpm for 8 minutes. Spores were resuspended in potato dextrose broth to a concentration of 0.1×10$^6$ spores/ml. Leaf #7 was detached from 4.5 week old greenhouse grown plants and placed on water agar, and a single 5 µl drop of the spore suspension was placed on each leaf. Leaves were then returned to the greenhouse. *P. parasitica* inoculations were done as described in Warren et al., Genetics 152:401–412, 1999. Assays for growth of *Psm* ES4326 and *Psm* ES4326(avrRpt2) were done as described in Volko et al., supra.

Camalexin Assays

Camalexin was assayed in *Psm* ES4326-infected leaves by visualization on TLC plates as described in Glazebrook et al., Proc. Natl. Acad. Sci. U.S.A. 91:8955–8959, 1994.

ACC Sensitivity Assay

Mutants were tested for ACC sensitivity following the procedure used by Van der Straeten et al., Plant Physiology 102:401–408, 1993.

Salicylic Acid Induction of PR-1

Seeds were sterilized and plated on 0.5×MS (0.5×MS salts, Gibco 500-1117; 1× Gamborg's B-5 vitamins, Sigma G1019; 2% sucrose; 1 g/l 2-[N-Morpholino]ethane-sulfonic acid; 0.8% Phytagar, GibcoBRL 10675-031). At 9 days after sowing, seedlings were transferred to 0.5×MS plates containing 0.5 mM SA. Seven days after transfer, seedlings were harvested for RNA extraction.

Mapping

DNA extractions and detection of CAPS markers were done according to the method described in Drenkard et al., supra. Primers and amplification conditions for the SSLP markers are detailed in Bell et al., supra.

RNA Analysis

Four and ½ week old plants were inoculated via settling tower and harvested at 7 days post inoculation. RNA was prepared and RNA gel blot performed as described by Reuber et al., The Plant Cell 8:241–249, 1996. Probes were prepared as described by Rogers et al., supra. Expression was quantitated by phosphorimager and is stated as a ratio to UBQ5. mRNA accumulation in the mutant lines is shown as a percentage of wild type levels.

Salicylic Acid Analysis

Salicylic acid was extracted and analyzed by HPLC using a modification of the methods described in Meuwly et al., 1993. For salicylic acid analysis, 0.3 to 0.5 gFW leaf tissue from *E. orontii*-infected leaves (7 dpi) was frozen in glass tubes with liquid nitrogen and either used directly or stored at −80° C. The frozen tissue was ground in liquid nitrogen to a fine powder using a chilled glass rod. Three ml of 90% methanol and 250 ng o-anisic acid (internal standard) were added to each sample. Samples were vortexed, sonicated for 20 minutes, and centrifuged for 20 minutes at 3000 rpm in a table-top centrifuge. The supernatant was transferred to a new tube, and the pellet was re-extracted with 2 ml of 90% methanol. The two supernatants were combined, divided into two portions of equal volumes (for total SA and free SA measurements), vacuum dried, and frozen at −80° C. For total SA, 500 µl β-glucosidase (80 U/ml in 100 mM sodium acetate, pH 5.2; Sigma, St. Louis, Mo.) was added to each sample. The samples were sonicated for 5 minutes, vortexed, covered with foil, and incubated for 90 minutes at 37° C. For both total and free SA samples, 2.5 ml 5% trichloroacetic acid was added, and the samples were vortexed, sonicated for 5 minutes, and centrifuged at 3000 rpm for 15 minutes. The supernatant was extracted twice with 2.5 ml of a 1:1 (v/v) mixture of ethyl acetate:cyclopentane. The organic phases were combined, vacuum dried, and frozen at −80° C. Just prior to loading samples on the HPLC, each was resuspended in 250 µl of 20% methanol, vortexed, sonicated for 5 minutes, and filtered through a 0.22 µm nylon filter.

HPLC separation of o-anisic acid (oANI) and salicylic acid was performed on a Waters 600 system equipped with Waters 474 Scanning Fluorescence detector and 996 Photodiode Array Detector (Waters Corporation, Milford, Mass.). A 5 µm, 15 cm×4.6 mm ID Supelcosil LC-ABZPlus column (Supelco, Bellefonte, Pa.) preceded by a LC-ABZ-Plus guard column was maintained at 27° C. and equilibrated in 15% acetonitrile with 25 mM KH$_2$PO$_4$ (pH 2.6) at a flow rate of 1.0 ml/min. Fifty µl of each sample was manually injected. The elution program began with an isocratic flow of 15% acetonitrile with 25 mM KH$_2$PO$_4$ (pH 2.6) for 1 minute, followed by a linear increase to 20% acetonitrile over 5 minutes, isocratic flow at 20% for 10 minutes, a linear increase from 20% to 55% acetonitrile over 17.5 minutes, and to 90% in 5 minutes. (For the second sample set, subsequent to the linear increase to 55% acetonitrile, a 1 minute 50:50 (v/v) acetonitrile:water wash followed by 5 minutes 100% acetonitrile wash was utilized to reduce possible salt precipitation.) The column was then rinsed with water for 1–2 minutes prior to equilibration in 15% acetonitrile with 25 mM $KH_2PO_4$ for 15 minutes and injection of the subsequent sample. oANI and SA were quantified using the fluorescence detector programmed to 305 nm excitation/365 emission for oANI and 305/407 emission for SA. Calibration curves for SA and oANI (Sigma, St. Louis, Mo.) were y=4.26x+3.46 ($R^2$=1.0) for oANI and y=3.11x+6.76 ($R^2$=0.99) for SA, where y is ng and x is area units×$10^{-4}$. oANI eluted at ~11.4 minutes and SA eluted at ~25.2 minutes; the detection limits for both compounds were 4 ng, similar to those reported by Meuwly et al., 1993. Using this extraction and HPLC method, we were also able to resolve and quantitate benzoic acid (PDA detection), trans-cinnamic acid (PDA detection), o-coumaric acid (PDA detection), and camalexin (fluorescence detection).

Callose Detection

Leaves were stained and examined microscopically as described in Reuber et al., (supra). At each time point, leaves were harvested from 2 plants per line. Multiple colonies on each leaf were observed.

All publications and patent applications mentioned in this specification are herein incorporated by reference.

Other embodiments are within the following claims.

What is claimed is:

1. A method for determining whether the success of a pathogen in infecting a plant is affected by a plant disease resistance pathway involving isochorismate synthase, the method comprising the steps of:
   (a) contacting a mutant *Arabidopsis thaliana* plant comprising a sid-2-2 mutation with a pathogen; and
   (b) assessing the level of infection of the mutant plant with the pathogen, compared to a control *Arabidopsis thaliana* plant containing a wild-type inducible isochorismate synthase gene, wherein an altered degree of pathogen infection or disease symptoms in the mutant plant, as compared to the control plant, indicates that the success of the pathogen in infecting the control plant is affected by a plant disease resistance pathway involving isochorismate synthase.

2. A method for determining whether a pathogen induces a plant disease resistance pathway involving isochorismate synthase in a plant, the method comprising the steps of:
   (a) contacting a mutant *Arabidopsis thaliana* plant comprising a sid-2-2 mutation with a pathogen, and
   detecting the level of salicylic acid produced in the mutant plant, where detection of decreased levels of salicylic acid in the mutant plant, compared to a control *Arabidopsis thaliana* plant comprising a wild-type inducible isochorismate synthase gene, indicates that the pathogen induces a disease resistance pathway involving isochorismate synthase in the plant.

* * * * *

UNITED STATES PATENT AND TRADEMARK OFFICE
CERTIFICATE OF CORRECTION

| | | |
|---|---|---|
| PATENT NO. | : 7,070,772 B2 | Page 1 of 1 |
| APPLICATION NO. | : 09/908299 | |
| DATED | : July 4, 2006 | |
| INVENTOR(S) | : Wildermuth et al. | |

It is certified that error appears in the above-identified patent and that said Letters Patent is hereby corrected as shown below:

Column 1, line 9: Immediately before "BACKGROUND OF THE INVENTION" insert the following paragraph:

--STATEMENT AS TO FEDERALLY SPONSORED RESEARCH
    This invention was made with Government support under Grant No. GM018707 awarded be the National Institutes of Health. The Government may have certain rights in this invention.--

Signed and Sealed this

Fourth Day of September, 2007

JON W. DUDAS
*Director of the United States Patent and Trademark Office*

SEQUENCE LISTING

<160> NUMBER OF SEQ ID NOS: 16

<210> SEQ ID NO 1
<211> LENGTH: 503
<212> TYPE: PRT
<213> ORGANISM: Arabidopsis thaliana

<400> SEQUENCE: 1

```
Met Thr Ala Val Leu Ser Pro Ala Ala Ala Thr Glu Arg Leu Ile Ser
 1               5                  10                  15

Ala Val Ser Glu Leu Lys Ser Gln Pro Pro Ser Phe Ser Ser Gly Val
            20                  25                  30

Val Arg Leu Gln Val Pro Ile Asp Gln Gln Ile Gly Ala Ile Asp Trp
        35                  40                  45

Leu Gln Ala Gln Asn Glu Ile Gln Pro Arg Cys Phe Phe Ser Arg Arg
    50                  55                  60

Ser Asp Val Gly Arg Pro Asp Leu Leu Leu Asp Leu Ala Asn Glu Asn
65                  70                  75                  80

Gly Asn Gly Asn Gly Asn Gly Thr Val Ser Ser Asp Arg Asn Leu Val
                85                  90                  95

Ser Val Ala Gly Ile Gly Ser Ala Val Phe Phe Arg Asp Leu Asp Pro
            100                 105                 110

Phe Ser His Asp Asp Trp Arg Ser Ile Arg Arg Phe Leu Ser Ser Thr
        115                 120                 125

Ser Pro Leu Ile Arg Ala Tyr Gly Gly Met Arg Phe Asp Pro Asn Gly
    130                 135                 140

Lys Ile Ala Val Glu Trp Glu Pro Phe Gly Ala Phe Tyr Phe Ser Val
145                 150                 155                 160

Pro Gln Val Glu Phe Asn Glu Phe Gly Gly Ser Ser Met Leu Ala Ala
                165                 170                 175

Thr Ile Ala Trp Asp Asp Glu Leu Ser Trp Thr Leu Glu Asn Ala Ile
            180                 185                 190

Glu Ala Leu Gln Glu Thr Met Leu Gln Val Ser Ser Val Val Met Lys
        195                 200                 205

Leu Arg Asn Arg Ser Leu Gly Val Ser Val Leu Ser Lys Asn His Val
    210                 215                 220

Pro Thr Lys Gly Ala Tyr Phe Pro Ala Val Glu Lys Ala Leu Glu Met
225                 230                 235                 240

Ile Asn Gln Lys Ser Ser Pro Leu Asn Lys Val Val Leu Ala Arg Asn
                245                 250                 255

Ser Arg Ile Ile Thr Asp Thr Asp Ile Asp Pro Ile Ala Trp Leu Ala
            260                 265                 270
```

```
Gln Leu Gln Arg Glu Gly His Asp Ala Tyr Gln Phe Cys Leu Gln Pro
        275                 280                 285

Pro Gly Ala Pro Ala Phe Ile Gly Asn Thr Pro Glu Arg Leu Phe Gln
    290                 295                 300

Arg Thr Gln Leu Gly Val Cys Ser Glu Ala Leu Ala Ala Thr Arg Pro
305                 310                 315                 320

Arg Ala Ala Ser Ser Ala Arg Asp Met Glu Ile Glu Arg Asp Leu Leu
                325                 330                 335

Thr Ser Pro Lys Asp Asp Leu Glu Phe Ser Ile Val Arg Glu Asn Ile
            340                 345                 350

Arg Glu Lys Leu Asn Gly Ile Cys Asp Arg Val Val Lys Pro Gln
        355                 360                 365

Lys Thr Val Arg Lys Leu Ala Arg Val Gln His Leu Tyr Ser Gln Leu
    370                 375                 380

Ala Gly Arg Leu Thr Lys Glu Asp Asp Glu Tyr Lys Ile Leu Ala Ala
385                 390                 395                 400

Leu His Pro Thr Pro Ala Val Cys Gly Leu Pro Ala Glu Glu Ala Arg
                405                 410                 415

Leu Leu Ile Lys Glu Ile Glu Ser Phe Asp Arg Gly Met Tyr Ala Gly
            420                 425                 430

Pro Ile Gly Phe Phe Gly Gly Glu Glu Ser Glu Phe Ala Val Gly Ile
        435                 440                 445

Arg Ser Ala Leu Val Glu Lys Gly Leu Gly Ala Leu Ile Tyr Ala Gly
    450                 455                 460

Thr Gly Ile Val Ala Gly Ser Asp Pro Ser Ser Glu Trp Asn Glu Leu
465                 470                 475                 480

Asp Leu Lys Ile Ser Gln Phe Thr Lys Ser Ile Glu Tyr Glu Ala Thr
                485                 490                 495

Thr Ser Leu Gln Ala Ile Asn
            500

<210> SEQ ID NO 2
<211> LENGTH: 512
<212> TYPE: PRT
<213> ORGANISM: Arabidopsis thaliana

<400> SEQUENCE: 2

Met Asn Gly Cys Glu Ala Asp His Lys Ala Pro Leu Gly Thr Val Glu
1               5                   10                  15

Thr Arg Thr Leu Ser Thr Val Pro Ser Pro Ala Ala Thr Glu Arg
            20                  25                  30

Leu Ile Thr Ala Val Ser Asp Leu Lys Ser Gln Pro Pro Phe Ser
        35                  40                  45

Ser Gly Ile Val Arg Leu Gln Val Pro Ile Glu Gln Lys Ile Gly Ala
    50                  55                  60

Ile Asp Trp Leu His Ala Gln Asn Glu Ile Leu Pro Arg Ser Phe Phe
65                  70                  75                  80

Ser Arg Arg Ser Asp Ser Gly Arg Pro Asp Leu Leu Gln Asp Phe Ser
                85                  90                  95

Ser Asp Asn Gly Ser Ser Asp His Asn Pro Val Ser Val Ala Gly Ile
            100                 105                 110

Gly Ser Ala Val Phe Phe Arg Asp Leu Asp Pro Phe Ser His Asp Asp
        115                 120                 125

Trp Arg Ser Ile Arg Arg Phe Leu Ser Ser Lys Ser Pro Leu Ile Arg
```

```
                130             135             140
Ala Tyr Gly Gly Leu Arg Phe Asp Pro Thr Gly Lys Ile Ala Val Glu
145                 150                 155                 160

Trp Glu His Phe Gly Ser Phe Tyr Phe Thr Val Pro Gln Val Glu Phe
                165                 170                 175

Asp Glu Phe Gly Gly Ser Ser Met Leu Ala Ala Thr Val Ala Trp Asp
                180                 185                 190

Asn Glu Leu Ser Trp Thr Leu Glu Asn Ala Ile Glu Ala Leu Gln Glu
            195                 200                 205

Thr Met Leu Gln Val Ser Ser Val Ile Met Arg Leu Arg Arg Glu Ser
210                 215                 220

Leu Gly Val Ile Val Ser Lys Asn His Val Pro Ser Glu Gly Ala
225                 230                 235                 240

Tyr Tyr Pro Ala Val Asn Asn Ala Leu Glu Ile Ile Lys Asp Lys His
                245                 250                 255

Ser Pro Leu Ser Lys Val Val Leu Ala Arg Ser Arg Ile Ile Thr
                260                 265                 270

Asp Thr Asp Ile Asp Pro Ile Ala Trp Leu Ala Arg Leu Gln Cys Glu
            275                 280                 285

Gly Gln Asp Ala Tyr Gln Phe Cys Leu Gln Pro Pro Gly Ala Pro Ala
290                 295                 300

Phe Ile Gly Asn Thr Pro Glu Arg Leu Phe His Arg Lys His Leu Gly
305                 310                 315                 320

Val Cys Ser Glu Ala Leu Ala Ala Thr Arg Pro Arg Gly Asp Ser Lys
                325                 330                 335

Val Arg Glu Met Glu Ile Glu Arg Asp Leu Leu Thr Ser Pro Lys Asp
                340                 345                 350

Asp Leu Glu Phe Ser Ile Val Arg Glu Asn Ile Arg Glu Lys Leu Lys
            355                 360                 365

Thr Ile Cys Asp Arg Val Val Lys Pro His Lys Ser Val Arg Lys
370                 375                 380

Leu Ala Arg Val Gln His Leu Tyr Ser Gln Leu Ala Gly Gln Leu Lys
385                 390                 395                 400

Arg Glu Asp Asp Glu Phe Asn Ile Leu Thr Ala Leu His Pro Thr Pro
                405                 410                 415

Ala Val Cys Gly Cys Pro Val Glu Glu Ala Arg Leu Leu Ile Lys Gln
                420                 425                 430

Ile Glu Ser Phe Asp Arg Gly Met Tyr Ala Gly Pro Ile Gly Phe Phe
            435                 440                 445

Gly Gly Gly Glu Ser Glu Phe Ser Val Gly Ile Arg Ser Ala Leu Val
450                 455                 460

Glu Lys Gly Leu Gly Ala Leu Ile Tyr Ala Gly Thr Gly Ile Val Ser
465                 470                 475                 480

Gly Ser Asn Pro Ser Ser Glu Trp Asn Glu Leu Glu Leu Lys Ile Ser
                485                 490                 495

Gln Phe Thr Lys Ser Leu Glu His Glu Ser Ala Leu Gln Pro Ile Asn
                500                 505                 510

<210> SEQ ID NO 3
<211> LENGTH: 6915
<212> TYPE: DNA
<213> ORGANISM: Arabidopsis thaliana

<400> SEQUENCE: 3
```

-continued

| | |
|---|---|
| tcaaagtctt gaataacaat aaaattatgt tcagctgaga gtctgagacc gcgtccaaca | 60 |
| ttttaaaaca cttttaaaag tcatactata atatctgagg accgtgtcta gtttcagttt | 120 |
| attcggtttt acaacagcaa tgatgcttgt tgaattatgg tttcattcta ttggattatc | 180 |
| tgcaagactt cttaatttta atatatagct cgtgatgata aataacaat ttgacttcta | 240 |
| aagtctagtc ctttatagtc ttaacaatat tcattttgac caggttgagt aaatcagaca | 300 |
| aaaatctaaa gacaaagaat aatcgtttcc tcaaatatgt acttggtgag ccgtcttaat | 360 |
| caccatatgt acatgagaat aaatgtgtaa tttggtggtt atttcataga aattttgggg | 420 |
| aaattgttgc acctctccac tctttgccag tctcgtgtga tcttaattga ctcaaaatga | 480 |
| aagaaaaaaa aacatgaaat taaagcaaat attcctattt gaattatgtt cctttaagat | 540 |
| ttttaacaat attttttaaa tgataaaaac tggtctcaaa gagcctaagt gggtttccta | 600 |
| gcaaaaaaag atactcaaag taatttactc ctcaaaataa tgcaatgatc taatgaagat | 660 |
| ctgttcaaat agtattgatt ttccaaattt aattatactc aaagagtttt aaaatctgtt | 720 |
| cttgttattc tatgctttgt tttacatgta aagtacttaa attcacttga tatttgttat | 780 |
| tactataatt ttagaaatgt gtcaaaattt aaaggagcat gcgtgtaatg ccatatgcct | 840 |
| tatgtacgag aacttgtaat gcgtttgcaa tttgtagtga catgtaatgt tttttacgat | 900 |
| agtttaaagt gcaaaccgct tccgtatcaa acgagaagag tcgtctagca tacaacaccc | 960 |
| acacgagagg aaccgcttag aaagagaatc cacttgaaat tgctgtccat gcattgctca | 1020 |
| aattcattga tacttggtct atgcaatttt acactacctc atttctgact atttcaattt | 1080 |
| gtcaagatat tataacatgc atttataact tttttgtcga cgataaatca accaaacgaa | 1140 |
| tccggtctgt atgtttgata acatgcattc atacaaaacg attatctgtt ttttagtcta | 1200 |
| tttaatttgg tttctacttt ttacttttgt gaaactaata ataatagatc aaacaattaa | 1260 |
| ctgatataat ttattaattt aattcttaga ccaagtaaat gattcatgaa atattaaatg | 1320 |
| cacgactaac tttagaaaaa tgtttctttg tatacataaa gatagaatag aagaaaagta | 1380 |
| ggattagaag aaaaaaacga aaatttcaga gtagtttact aaagaaattc tgagaaattt | 1440 |
| tgtgtgaaaa tgaaatgaaa atcttcaatt ttagtgggcc cctgctacat cagtccccta | 1500 |
| tttatatctc ttctcaactc taaacccaaa ccaaaaaaaa acagaaagag caatctctct | 1560 |
| atactacaaa caccaaagtt taaaattaaa caaaatcttc aagaaacact ttacgaattt | 1620 |
| ctgcaatggc ttcacttcaa ttttcttctc agtttctggg ctcaaacact aaaacacaca | 1680 |
| gctctatcat ttccatctct cgtagttact ctccaactcc attcactaga ttctcccgca | 1740 |
| aggtcttttt tctgttttgt tttgtttttt tcaattctgt tctttttttt ggaggaattc | 1800 |
| ataatgatta acttaatttt attggataat tttcagaagt atgagtcatg ttcgatgtct | 1860 |
| atgaatggtt gtgatggaga tttcaagacg ccacttggta cagtggagac aaggactatg | 1920 |
| actgctgttt tatctccggc agccgccact gaaaggctaa tctccgccgt ctctgaactc | 1980 |
| aaatctcaac ctccgtcgtt ttcctccggc gtcgttcggt tacaggtaca tcactacatc | 2040 |
| atcatcatca tcatcatcct ctgttttttt cttctaagac acaatccgat ttgctgctgt | 2100 |
| atgtgaaaga atgagatcac gccacgtggt gttttacat tggtctgtgg tgatttcgtt | 2160 |
| ctctagcttg ctgtccttgct gcatcgttta tgcctaatca tttaagatcc taatcgttat | 2220 |
| gattattaaa atcatactat aaagcagagc tcacaacaac gataaatata tccaaatcta | 2280 |
| acagttaatc ataaactatt agaagatgac taataattat caaaaagata tggttattat | 2340 |
| atttcttatt agtttatgaa taaaacacac actcgaactc ggtcgtacaa gattccgtga | 2400 |

```
gtccatcgaa ctatttaatt gggacttttg ggacctttac atgtaaatta taatgaatat    2460
tttcttttag tcaattttac gtagactaaa tcaaatacat tttagaaaga ataatcatgt    2520 tttttttagtc ctcgaaatct aatttaacac tgttaacttt tagttagtgt ggccatgcta   2580
agataattta gctagaaaag taataatttt gtgttttgtg ggccagaaaa taagtaaaat    2640
aatgattaga atccaatttg ttgtaaaggc aaggcggcga tcaaatacag tcactctcat    2700
taaaacgcag agttttttaa aaaacccaaa tcacagtcga attttcccgc gcaataaacc    2760
ctaatttgga tttggtgcag gttccaattg accagcaaat cggagcaatt gattggcttc    2820
aagcccagaa tgagattcag cctcgctgtt tcttctctcg tcgcagtgac gttggtcgtc    2880
ccgatcttct tctcgatcta gctaacgaga acggaaacgg aaacgaaaac ggaacagtgt    2940
catctgatcg taatctggtt agcgttgctg gtatcggctc tgcagttttc ttccgtgacc    3000
ttgatccttt ctctcatgac gattggagat ccatcagaag ttttttgtct tcaacgtcac    3060
ctctgattcg tgcctatggt ggtatgcgtt ttgatcctaa tggcaagatc gctgttgaat    3120
gggaaccttt tggtgcattt tacttttcag tccctcaggt acctttaaag attgattctt    3180
tataagagat tttttgagtt tgtgttgttg tttaactggc tgatacatgt gcaggttgag    3240
tttaatgagt ttggtggaag ttcaatgttg gctgcaacta ttgcttggga tgatgaactc    3300
tcttggactc tggaaaatgc tattgaagca ctccaggaga ctatgcttca agtttcttct    3360
gttgtaatga agttgagaaa cagatcttta ggagtatctg ttttaagcaa gaatcatgtt    3420
cctaccaaag gagcttattt ccctgctgta gagaaggctt tagagatgat taaccagaaa    3480
agttcacccc ttaacaaggt agtttagact ttagagattg tgttcgtatc tattcttaaa    3540
acaagtttat aggtttcgtt ttaactgatg tttttggctc gtggaattag ttgttcttg    3600 ctcgtaacag caggataatt acggataccg acattgatcc cattgcttgg ctagcacagt    3660
tacaggtgtg ttttatctc tggatattat atagtagtca gttttcaatg tttagattta    3720
tatctcacta attttttgt gtgacagcgt gaagggcatg atgcatatca gttctgtctt    3780
caaccacctg gtgcaccagc ttttatcgga aacacggtag gtctttttat atgtagtctg    3840
tgataataag ttctgttgat aaagatatgt gcacatttgt tatttatttc taagaaatat    3900
gtttgtgaca tacatctttg tgaaacagcc tgagagacta ttccaaagga ctcaattagg    3960
tgtctgcagt gaagctttgg ctgcaactag gcctagagct gcttctagtg ctcgtgatat    4020
ggagatagag cgtgacttac taaccaggtc aattttttact tcaagtgctt tgaacaatta    4080
cagaatccag ttctccatta tcattttact gaatttttgc taaactgttg cagtccgaaa    4140
gacgacctcg agttctctat cgtacgagag aatataagag aaaagttaaa cgtaagttca    4200
atcttgatgc tctgcagctt caatgcttca tttcttggat aatagtttgg tatatttttt    4260
cttattatgc tttcttctgc tttgcagggt atatgtgaca gagttgttgt caagcctcaa    4320
aaaactgtga ggaagcttgc aagagtgcaa catctatatt ctcaattggc agggagactt    4380
acgaaggaag atgatgaggt gagataatag tattggaata gttttttacat ttccaagctc    4440 ttcatttctt cgaattagct ttaacccttt ttctttctat ctgtctatag tataaaatat    4500
tggctgctct gcatccaact ccagctgttt gtgggcttcc agcagaagaa gcaaggcttt    4560
tgattaagga gataggtaaa atatctacct tggttcaact atcttctagt aactatagat    4620
gtagagatta agaattatgc tgactcaaac attttgcttc ttctagaatc attcgataga    4680
ggaatgtatg cgggacctat tggatttttt ggtggcgagg agagtgaatt tgcagtcggg    4740
```

-continued

```
atcagatcag ctctagtcga aaaggtgagc ttatttgatc tctttctccc tttaaaaaac    4800
acactttaac actaattgtt atagcaaaat cgatcattac ggttttttgct acaacttgta   4860
aaaaaatgct gaactgtatt ttgatttaca gggtcttggg gcattgatct atgcggggac   4920
agggatagta gctggaagtg acccatcttc agagtggaat gagcttgatc ttaagatatc   4980
tcaggtacga gcttttgtcc agaaaatgtt tagtgacatc atggttctct gttaccaaaa   5040
tcctaatttt tattctctct tttgttgttg tttttgcagt tcaccaagtc aattgaatat   5100
gaagcaacaa catctctaca ggcgattaat tgaagaaaga gtaacatttg tatttgattg   5160
ttttgtttgt atgggggata aggggttctc acaataagaa agcaatgttg tctctcttgt   5220
aaattaaaaa agaaatgctt taatttgtta atgggccgag cctttttcggg ttgtaactag  5280
ggcaggccta tcatgaatgt tcataggcct agctgttatg attgttaatg agcttctata   5340
gtgtttttct tcaaagacag atatattcaa tatggatcta aaactgaact gaatttaact   5400
gacatgacaa tcgaatcaaa ttgaatttat tttttcaatt ttcatttagc aagaagtgac   5460
ccatcttcag agtgaagtaa tctatgctta ttatctcgat taagcaaaaa tccgtagaat   5520
gcttgggcct ttcaacgatg atgtagccgt gtaggacagg tttacggaat ctgcttttat   5580
gcaaatggta aatattaata ttcctttata agttagcgtt tcagatcatc ttctttcgtt   5640
agattaagaa actactttgt tattatataa ctataaatac catccaacaa ccttactcgc   5700
catatctttt catgtgtggt ggtttatagg aacattgaaa agtaccatat tataaaatga   5760
agaatcaaca cgtcaacaaa acacaaaata aaatgagata gtacaattaa aaaaatggag   5820
cgcatgtaaa aagtgaagaa tcaaacgaag gcttggcgat agagaatgga atcagatttc   5880
ccattatccc cactctaaca ccatatattc ctttcccttt ttaccctcca cctcaattag   5940
gtttattaat catatttaac actctaatta accaacccat ttcatctctt ttattttact   6000
aatcacaatg ctttggcctc attacgtttt acctagattt actttgtcac aaactacaca   6060
aatatgaacc taattatcta cactcgtgtc agaaacagtt ttagctaata tttagtaagt   6120
tttaattaaa actaatgaaa tgaataaata gtgtatagta cataggatt gttttagtt    6180
tattaatgga aattaagatt tcattagtac taaaaacatg taaataaaat aaagctttaa   6240
agaggaatat attcaaataa aaaaagcaag acctcgaaaa aaaaactttc tattatctct   6300
cttccgcgat taccgtaatc tctgtcacaa acaacaaaac cttctctctc tcactatctt   6360
aatgagagaa gaagcattc tcgagaaatg agaagactac cactacgatg aacacgacgc    6420
cgtttcactc ggatcctccg ccgtcgagga tccagcgtaa gctcgttgtc gaagttgttg   6480
aagctcgtaa tattctccct aaagatggtc aaggaagctc tagcgcttac gtcgttgtcg   6540
atttcgatgc tcagaagaaa cgaacctcca ctaagttccg tgacctaaac cctatttgga   6600
acgagatgct tgatttcgcc gtctccgatc ccaaaaacat ggattacgac gagctcgata   6660
tcgaggttta taacgataaa agatttggta acggaggtgg ccggaagaat catttctcg    6720
gtagggttaa gatctatgga agccagttct cgcgaagagg tgaagaaggt cttgtgtatt   6780
tccctttgga gaagaagagt gtgttcagct ggattcgcgg cgagattgga ctcaaaatct   6840
actattacga cgaagccgcc gacgaagaca cggcgggtgg aggtggagga cagcaacaac   6900
aacagcaaca gcaac                                                     6915
```

<210> SEQ ID NO 4
<211> LENGTH: 4328
<212> TYPE: DNA
<213> ORGANISM: Arabidopsis thaliana

<400> SEQUENCE: 4

```
ctcgagttat tttcaaaaag cagtatcggc tagagcatca agaaactcga ttaaaagttt      60
atcaaatgaa gctggaaaag tcttgacaga gttagaagac attaaaatag aggttgtgga     120
gtattgtaaa agaattatgc aagcgcaacc tacatgacta gtggagatat catatgacta     180
cttatcaggg ttggtgaatt ttaaatattc ccagactgct gctaaaacct taatgcatcc     240
aattggtgtt gacgagatgg ctatcctgct cagttttaa ttgctgcttg gtcgatcttg      300
gaaatgattt tataatagca gtgcagtcct tcttgatctt tggatgcatg cccaaaagtg     360
ttaaatcaac tattctgact cttgttccca aaacagatgg tgcacaaaat atgaaggagt     420
tcatactgat agcgtgatgc aatcttctat attaagtgat atataagata atagcaaacc     480
ggcttaaagt tactttacaa gaggcgatgg aaccgaatca gagcaccttt gtgaagggga     540
ggctcttact agagaacata ttttagcaa caaaactagt caaggactac cacaagcaat     600
cactctcatc tcgtttagca attaagcttg atatctctaa agcgtttgac atagagcaat     660
ggccgtttat tgctgctagg ctacgtgtga tgggttatcc atagctcttt atacactaga     720
taaatatatg catctctacg tcctcgtttt gttttttct ctagctcttg tggtataagg      780
aaaggatgct ctctttcacc gtacttctat gttatcatca acaatgtttt gtcgactatg     840
ttaaacagag cagctgttat gaaagagatt ggttctcacc cgttttgcaa ggagataaag     900
cttacacatc ttagttttgc tgatgatatt atggtcttca tggatggtac tcttggttct     960
ctctgcaaca tcatgatagt ggttgatgag tatgcccata tttcagtttt taacatcaat    1020
gtgtccaagt ccacaatatt tgatgcgggt cgagggaaga tgactttgga aataggggcc    1080
acatcagtag ggttagtagt aagttctctt cccatttggt accttgggct gcgctaacca    1140
caaaagcaat gacgagactt gactacaaac ctctacttga caagataagg tctcgttttt    1200
taattggaca agcaagcacc tctcacttga ggttgtctac aacttatgaa ctcagttata    1260
tgaagcatct taattttctg gtgttcagtc ttcaggcttc caaaaaatgt ttttagacat    1320
tgaaggagg tgtagttcat tcctctagag tggatcatcg cttgatgcaa ctaaagcaaa    1380
agtgtcttgg gaggaggttt gctactcaaa aaaggaaggg ggcttggggt tccgcgtatg    1440
atggagatgt ctttgattta tgcgttgagc ctaatatgga ggttatatac catgtcgggc    1500
tctctatggg tggcatagat aagtcattac cttctgcgcc aagaatcatt ttgggatatc    1560
aaagcaacgt cctagggtc ttcggttgga cgtaagctgc tcaagctttg cccacaagcc     1620
attgagttta taagaatgga agtaaaagat ggagttaaga cacgatccta gtcggatact    1680
tggttgtcaa tggggagtct tattgatcgt agttggagaa aggggaacat atgaattggg    1740
agtgcaccga gatgctacag ttgcagaggt tgtagcaaga ggtcactggt caatccgtcg    1800
tggtcagaac caacatataa gtttgattgt ggaccagatc atagctaaag acccgtccgt    1860
acactcggct agtcaagatc attgattagt atatatacat attgtattgc atgaaaagtg    1920
tttaaagtaa attgtgtcct atacaaagaa tatatataac gatcattgat tagtatatat    1980
acatattgta ttgtgtgttt aaagtaaatt gtgtcctata caaagaatat ctttgtggag    2040
aagcaaagag aatacatact tacgtaggaa tcttttttgtt ttctttttc acaacgtaag    2100
aatgtttgct tccttacaat tcatacttat taacttacat attatgtttt cttttaaata    2160
ttaaaaataa ctaattttta ttaggcagca agtcatttac aaagtaaaaa atttctccat    2220
gcatgtaacc ttcatttatc attcatttta gtttgtaact ttttattaga ttttgatcaa    2280
```

-continued

```
gttaaccgct aaaatctcat tttatccgtt cgcattaaag ttaaatagat tgctgacata    2340
ttttaaatct aatagaaaat gccatctggc aaataaacaa cggacacgat tttaaactaa    2400
attttaccaa aaagaaaaaa cttatacgac ttttcttgct tagaagtctt tgcattgtta    2460
atagattgtt gaaaaggttt attcattact ttcatgcaga gagataacat atcatcgcgt    2520
ggggatttat tcaatccaaa gaaaagcttc caaaaactga ctctgcttca tgaaacactc    2580
actctaattt gcttcatcaa tcttaggact gacttttcca awycaatatg cggaactatc    2640
ttctaattta cattggtttc gtgtttttc gaaggagac aactatcttt ttaaaagctt     2700
ttctatagtg tgatgacaaa aaaaaaatgt aattgttagt tgcaaaagaa aagtacaata    2760
gtcttttcta gttttgagag tttaaggttt atgatcggaa cttagagtkt aaatttaaac    2820
tattttgtta attttttggac tgataacagt ttttttttga aaatattgaa acgttgttta    2880
cctaatgtaa catgttattc tacttaaatt actttatatt ttaataacat ataatattga    2940
ataggatatc ataggatatt attacgtaat aatatcctat ggtgtcattt tataagttag    3000
cacaagcttg ttttaactta taaaatgatt ctccctccat ataaaaaagt ttgattttat    3060
agaatgttta taccgattaa aaaaataata atgcttagtt ataaattact atttattcat    3120
gctaaactat ttctcgtaac tattaaccaa tagtaattca tcaaattta aaattctcaa     3180 ttaattgatt cttgaaattc ataacctttt aatattgatt gataaaaata tacataaact    3240
caatcttttt aatacaaaaa aactttaaaa aatcaattt tctgattcgg agggagtata     3300
tgttattgct tagaatcaca gattcatatc aggattggaa aatttaaag ccagtgcata     3360 tcagtagtca aaattggtaa atgatatacg aaggcggtac aaaattaggt atactgaaga    3420
tagaagaaca caaagtaga tcggtcacct agagttttc aatttaaact gcgtattagt      3480
gtttggaaaa aaaaaacaaa gtgtatacaa tgtcaatcgg tgatctttt ttttttttt      3540 ttttttttt tctttttgg ataaatctca atgggtgatc tattgactgt ttctctacgt      3600
cactatttta cttacgtcat agatgtggcg gcatatattc ttcaggactt ttcagccata    3660
ggcaagagtg atagagatac tcatatgcat gaaacactaa gaaacaaata attcttgact    3720
tttttctttt tatttgaaaa ttgactgtag atataaactt ttattttttc tgactgtaaa    3780
tataatctta attgccaaac tgtccgatac gatttttctg tattatttac aggaagatat    3840
cttcacaaca ttttgaatga agtaatatat gaaattcaaa tttgaaatag aagacttaaa    3900
ttagaatcat gaagaaaaaa aaacacaaaa caactgaatg acatgaaaca actatataca    3960
atgtttctta ataacttca tttagggtat acttacatat atactaaaaa aatatatcaa     4020
caatggcaaa gctaccgata cgaaacaata ttaggaaaaa tgtgtgtaag gacaagattg    4080
acaaaaaaat agttacgaaa acaacttcta ttcatttgga caattgcaat gaatattact    4140
aaaatactca cacatggacc atgtatttac aaaaacgtga gatctatagt taacaaaaaa    4200
aaaaagaaaa aaatagtttt caaatctcta tataagcgat gtttacgaac cccaaaatca    4260
taacacaaca ataaccatta tcaacttaga aaaatgaatt ttactggcta ttctcgattt    4320
ttaatcgt                                                             4328
```

<210> SEQ ID NO 5
<211> LENGTH: 1973
<212> TYPE: DNA
<213> ORGANISM: Arabidopsis thaliana
<220> FEATURE:
<221> NAME/KEY: misc_feature
<222> LOCATION: 1288, 1934, 1958, 1960, 1962, 1964, 1970
<223> OTHER INFORMATION: n = A,T,C or G

<400> SEQUENCE: 5

```
actttacgaa tttctgcaat ggcttcactt caattttctt ctcagtttct gggctcagac      60
actaaaacac acagctctat catttccatc tctcgtagtt actctccaac tccattcact     120
agattctccc gcaagaagta tgagtcatgt tcgatgtcta tgaatggttg tgatggagat     180
ttcaagacgc cacttggtac agtggagaca aggactatga ctgctgtttt atctccggca     240
gccgccactg aaaggctaat ctccgccgtc tctgaactca atctcaacc tccgtcgttt      300
tcctccggcg tcgttcggtt acaggttcca attgaccagc aaatcggagc aattgattgg     360
cttcaagccc agaatgagat tcagcctcgc tgtttcttct ctcgtcgcag tgacgttggt     420
cgtcccgatc ttcttctcga tctagctaac gagaacggga acggaaacgg aaacggaaca     480
gtgtcatctg atcgtaatct ggttagcgtt gctggtatcg gctctgcagt tttcttccgt     540
gaccttgatc ctttctctca tgacgattgg agatccatca aaggtttttt gtcttcaacg     600
ccacctctga ttcgtgccta tggtggtatg cgttttgatc ctaatggcaa gatcgctgtt     660
gaatgggaac cttttggtgc attttacttt tcagtccctc aggttgagtt taatgagttt     720
ggtggaagtt caatgttggc tgcaactatt gcttgggatg atgaactctc ttggactctg     780
gaaaatgcta ttgaagcact ccaggagact atgcttcaag tttcttctgt tgtaatgaag     840
ttgagaaaca gatctttagg agtatctgtt ttaagcaaga atcatgttcc taccaaagga     900
gcttatttcc ctgctgtaga gaaggcttta gagatgatta accagaaaag ttcaccccct     960
aacaaggttg ttcttgctcg taacagcagg ataattacgg ataccgacat tgatcccatt    1020
gcttggctag cacagttaca gcgcgaaggg catgatgcat atcagttctg tcttcaacca    1080
cctggtgcac cagcttttat cggaaacacg cctgaaagac tattccaaag gactcgatta    1140
ggtgtctgca gtgaagcttt ggctgcaact aggcctagag ctgcttctag tgctcgtgat    1200
atggagatag agcgtgactt actaaccagt ccgaaagacg acctcgagtt ctctatcgta    1260
cgagagaata taagagaaaa gttaaacngt atatgtgaca gagttgttgt caagcctcaa    1320
aaaactgtga ggaagcttgc aagagtgcaa catctatatt ctcaattggc agggagactt    1380
acgaaggaag atgatgagta taaaatattg gctgctctgc atccaactcc agctgtttgt    1440
gggcttccag cagaagaagc aaggcttttg attaaggaga tagaatcatt cgatagagga    1500
atgtatgcgg gacctattgg attttttggt ggcgaggaga gtgaatttgc agtcgggatc    1560
agatcagctc tagtcgaaaa gggtcttggg gcattgatct atgcggggac agggatagta    1620
gctggaagtg acccatcttc agagtggaat gagcttgatc ttaagatatc tcagttcacc    1680
aagtcaattg aatatgaagc aacaacatct ctacaggcga ttaattgaag aaagagtaac    1740
atttgtattt gattgttttg tttgtatggg ggataagggg ttctcccaat aagaaagcaa    1800
tgttgtctct cttgtaaatt aaaaaagaaa tgctttaatt tgttaatggg ccgagccttt    1860
tcgggttgta actagggcag gcctatcatg aatgttcata ggcctagctg ttatgattgt    1920
taatgagctt ctanagtgtt tttcttcaaa aaaaaaanan ananaaaaan aaa            1973
```

<210> SEQ ID NO 6
<211> LENGTH: 2078
<212> TYPE: DNA
<213> ORGANISM: Arabidopsis thaliana

<400> SEQUENCE: 6

```
ttctctctct ctctctctct ctcccatcca atggcatcta tcacagggca ttgtgttgct      60
```

```
catttcacag accttcaac caggaaatct tctttttct ctaattctaa taataactct    120
tcccttttta gaagaaagtc tacaaatata gtcaccagaa aaaatatat attttgttct    180 acatcattgt ccatgaatgg ttgcaatggt gatccaagag ctccggttgg aactatagaa    240
acgaggacac ttccggcggt ttcgacgccg gcattggcca tggaacgtct tagctccgcc    300
gtggctaact tgaaatcaac tctaccttct gctcaatcag ggatcatccg tcttgaggta    360
ccaattgaag aacatataga agcactagac tggcttcatt cgcaagacca aaaaaacctt    420
cttccccgtt gctatttctc tggtagaagt caagttacct tctctgattt cacatctaac    480
gaccttacaa atagaaatgg gagtgccgcc aatggacatc ttcaacgaat ttctacttca    540
tctgatgata agaatctggt cagtgttgct ggtgtcggtt ctgcagtcct cttccggagc    600
ccaaatccat ttctcttga tgattggctc tcaattaaga ggttttttgtc caagaactgc    660 ccattaatcc gtgcttatgg agcaattcgc tttgatgcaa ggcctcatat agcaccagag    720
tggaaggctt ttggctcatt ttacttcgtg gttcctcagg ttgagtttga tgagctacat    780
ggaagttcca tgattgctgc aacagttgca tgggataatg ctctctcttt gacatatcaa    840
caagcaatag ttgcacttca acaacaatg gagcaggttt cctctaccgt ctccaaacta    900
agacaagatg tctctcatac ttcttggtg agcaaggcta atattcctga taacatcc    960 tgggatctta ctcttaaccg agttttggaa gaaataggca caaatattc gccattgaca    1020 aaggttgtac ttgcacgtcg tagtcaagtt atcacaacat cagatattga tcctttggct    1080
tggctgagta gtttcaaggc tgatgggaaa gatgcttacc aatttgcct tcagcctcat    1140 gaagcaccag cattcattgg aaacactcca gagcaactat ttggccggga ccagctaacc    1200 gttttttagtg aggctttggc tgcaacccga gccaggggtg aatcagattc gttagatctt    1260
cagatggcac atgatctctt ttccagtccc aaggataacc acgagtttgc catagtacga    1320
gagaacatca gacagaaact agatgccatt tgtactagtg tagaaactga accaatgaag    1380
tcagtaagaa agcttaagag aattcaacat ctttatgctc gatttgcagg cagattacgc    1440
tctgaagatg atgagttcaa gattttgtct tcccttcatc ctactccagc tgtttgtggg    1500
tttcctatgg aagatgcacg gaaatttatt gcggaaaatg aaatgtttga ccgaggatta    1560
tacgctggcc ctgttggttt ctttggagga gctcagagtg attttctgt tggaataaga    1620 tctgccttga ttggaaagga tgccggtgca ttaatatat cggggcttgg ggttgtagaa    1680
ggaagtgatc cagctctaga atggcaggaa ctagagctca aggcatcgca gtttatgaag    1740
ttgatgaaat tagaggcacc tgctttgaag tgaaattag gactgaaaaa tcaataaaaa    1800
gattgcgata gaaatttcag ataattcgtt agccagaaga tcttgttgag ccgttattaa    1860
atgtgtcctc tacagtttaa ctgataacca gatgaagaaa acctatatct agtatatata    1920
tatctaccat atataaatat attgtacatt tttgtttttt ctcccacaaa tttattttgt    1980
atctttttga acattgtgcc agctggttta ttgtattcca ttatcttaat tcattattca    2040
ataagatgtg tcaattcatt caaaaaaaaa aaaaaaa                             2078
```

<210> SEQ ID NO 7
<211> LENGTH: 105
<212> TYPE: PRT
<213> ORGANISM: Arabidopsis thaliana

<400> SEQUENCE: 7

```
Met Leu Ile Lys Ile Cys Ala Pro Ser Phe Phe Val Ser Asn Lys Tyr
 1               5                  10                  15
```

```
Val Cys Lys Gln Pro Glu Arg Leu Phe Gln Arg Asn Arg Leu Gly Val
            20                  25                  30

Cys Ser Glu Ala Leu Ala Ala Thr Arg Pro Arg Ala Ala Ser Arg Gly
        35                  40                  45

Arg Asp Met Glu Ile Glu Arg Asp Leu Leu Thr Ser Gln Phe Ser Ile
    50                  55                  60

Val Arg Glu Asn Thr Arg Glu Lys Leu Asn Val Thr Pro Lys Thr Val
65                  70                  75                  80

Arg Lys Leu Ala Arg Val Gln His Leu Tyr Ser Gln Leu Ala Gly Lys
                85                  90                  95

Leu Thr Lys Glu Asp Asp Glu Val Ile
            100                 105

<210> SEQ ID NO 8
<211> LENGTH: 2078
<212> TYPE: DNA
<213> ORGANISM: C. roseus

<400> SEQUENCE: 8
ttctctctct ctctctctct ctcccatcca atggcatcta tcacagggca ttgtgttgct      60
catttcacag acctttcaac caggaaatct tcttttttct ctaattctaa taataactct     120
tccctttta gaagaaagtc tacaaatata gtcaccagaa aaaaatatat attttgttct     180
acatcattgt ccatgaatgg ttgcaatggt gatccaagag ctccggttgg aactatagaa     240
acgaggacac ttccggcggt ttcgacgccg gcattggcca tggaacgtct tagctccgcc     300
gtggctaact tgaaatcaac tctaccttct gctcaatcag ggatcatccg tcttgaggta     360
ccaattgaag aacatataga agcactagac tggcttcatt cgcaagacca aaaaaacctt     420
cttccccgtt gctatttctc tggtagaagt caagttacct tctctgattt cacatctaac     480
gaccttacaa atagaaatgg gagtgccgcc aatggacatc ttcaacgaat ttctacttca     540
tctgatgata agaatctggt cagtgttgct ggtgtcggtt ctgcagtcct cttccggagc     600
ccaaatccat tttcttttga tgattggctc tcaattaaga ggttttttgtc caagaactgc     660
ccattaatcc gtgcttatgg agcaattcgc tttgatgcaa ggcctcatat agcaccagag     720
tggaaggctt ttggctcatt ttacttcgtg gttcctcagg ttgagtttga tgagctacat     780
ggaagttcca tgattgctgc aacagttgca tgggataatg ctctctcttt gacatatcaa     840
caagcaatag ttgcacttca acaacaatg gagcaggttt cctctaccgt ctccaaacta     900
agacaagatg tctctcatac ttctttggtg agcaaggcta atattcctga tagaacatcc     960
tgggatctta ctcttaaccg agttttggaa gaaataggca caaatattc gccattgaca    1020
aaggttgtac ttgcacgtcg tagtcaagtt atcacaacat cagatattga tccttttggct    1080
tggctgagta gtttcaaggc tgatgggaaa gatgcttacc aatttttgcct tcagcctcat    1140
gaagcaccag cattcattgg aaacactcca gagcaactat ttggccggga ccagctaacc    1200
gtttttagtg aggctttggc tgcaacccga gccaggggtg aatcagattc gttagatctt    1260
cagatggcac atgatctctt ttccagtccc aaggataacc acgagtttgc catagtacga    1320
gagaacatca gacagaaact agatgccatt tgtactagtg tagaaactga accaatgaag    1380
tcagtaagaa agcttaagag aattcaacat ctttatgctc gatttgcagg cagattacgc    1440
tctgaagatg atgagttcaa gattttgtct tcccttcatc ctactccagc tgtttgtggg    1500
tttcctatgg aagatgcacg gaaatttatt gcggaaaatg aaatgtttga ccgaggatta    1560
tacgctggcc ctgttggttt ctttggagga gctcagagtg attttctgt tggaataaga    1620
```

-continued

```
tctgccttga ttggaaagga tgccggtgca ttaatatatg cggggcttgg ggttgtagaa    1680
ggaagtgatc cagctctaga atggcaggaa ctagagctca aggcatcgca gtttatgaag    1740
ttgatgaaat tagaggcacc tgctttgaag tgaaaattag gactgaaaaa tcaataaaaa    1800
gattgcgata gaaatttcag ataattcgtt agccagaaga tcttgttgag ccgttattaa    1860
atgtgtcctc tacagtttaa ctgataacca gatgaagaaa acctatatct agtatatata    1920
tatctaccat atataaatat attgtacatt tttgtttttt ctcccacaaa ttttatttgt    1980 atcttttga acattgtgcc agctggttta ttgtattcca ttatcttaat tcattattca    2040
ataagatgtg tcaattcatt caaaaaaaaa aaaaaaaa                            2078
```

<210> SEQ ID NO 9
<211> LENGTH: 476
<212> TYPE: PRT
<213> ORGANISM: P. aeruginosa

<400> SEQUENCE: 9

```
Met Ser Arg Leu Ala Pro Leu Ser Gln Cys Leu His Ala Leu Arg Gly
 1               5                  10                  15

Thr Phe Glu Arg Ala Ile Gly Gln Ala Gln Ala Leu Asp Arg Pro Val
                20                  25                  30

Leu Val Ala Ala Ser Phe Glu Ile Asp Pro Leu Asp Pro Leu Gln Val
            35                  40                  45

Phe Gly Ala Trp Asp Asp Arg Gln Thr Pro Cys Leu Tyr Trp Glu Gln
    50                  55                  60

Pro Glu Leu Ala Phe Phe Ala Trp Gly Cys Ala Leu Glu Leu Gln Gly
65                  70                  75                  80

His Gly Glu Gln Arg Phe Ala Arg Ile Glu Gly Asn Trp Gln Leu Leu
                85                  90                  95

Cys Ala Asp Ala Val Val Glu Gly Pro Leu Ala Pro Arg Leu Cys Gly
            100                 105                 110

Gly Phe Arg Phe Asp Pro Arg Gly Pro Arg Glu Glu His Trp Gln Ala
        115                 120                 125

Phe Ala Asp Ala Ser Leu Met Leu Ala Gly Ile Thr Val Leu Arg Glu
    130                 135                 140

Gly Glu Arg Tyr Arg Val Leu Cys Gln His Leu Ala Lys Pro Gly Glu
145                 150                 155                 160

Asp Ala Leu Ala Leu Ala Ala Tyr His Cys Ser Ala Leu Leu Arg Leu
                165                 170                 175

Arg Gln Pro Ala Arg Arg Pro Ser Gly Pro Thr Ala Gly Ala Gln
            180                 185                 190

Gly Asp Ala Ser Ala Gln Glu Arg Gln Trp Glu Ala Lys Val Ser
        195                 200                 205

Asp Ala Val Ser Ser Val Arg Gln Gly Arg Phe Gly Lys Val Val Leu
    210                 215                 220

Ala Arg Thr Gln Ala Arg Pro Leu Gly Asp Ile Glu Pro Trp Gln Val
225                 230                 235                 240

Ile Glu His Leu Arg Leu Gln His Ala Asp Ala Gln Leu Phe Ala Cys
                245                 250                 255

Arg Arg Gly Asn Ala Cys Phe Leu Gly Ala Ser Pro Glu Arg Leu Val
            260                 265                 270

Arg Ile Arg Ala Gly Glu Ala Leu Thr His Ala Leu Ala Gly Thr Ile
        275                 280                 285
```

-continued

```
Ala Arg Gly Gly Asp Ala Gln Glu Asp Ala Arg Leu Gly Gln Ala Leu
    290                 295                 300

Leu Asp Ser Ala Lys Asp Arg His Glu His Gln Leu Val Val Glu Ala
305                 310                 315                 320

Ile Arg Thr Ala Leu Glu Pro Phe Ser Glu Val Leu Glu Ile Pro Asp
                325                 330                 335

Ala Pro Gly Leu Lys Arg Leu Ala Arg Val Gln His Leu Asn Thr Pro
            340                 345                 350

Ile Arg Ala Arg Leu Ala Asp Ala Gly Gly Ile Leu Arg Leu Leu Gln
        355                 360                 365

Ala Leu His Pro Thr Pro Ala Val Gly Gly Tyr Pro Arg Ser Ala Ala
    370                 375                 380

Leu Asp Tyr Ile Arg Gln His Glu Gly Met Asp Arg Gly Trp Tyr Ala
385                 390                 395                 400

Ala Pro Leu Gly Trp Leu Asp Gly Glu Gly Asn Gly Asp Phe Leu Val
                405                 410                 415

Ala Leu Arg Ser Ala Leu Leu Thr Pro Gly Arg Gly Tyr Leu Phe Ala
            420                 425                 430

Gly Cys Gly Leu Val Gly Asp Ser Glu Pro Ala His Glu Tyr Arg Glu
        435                 440                 445

Thr Cys Leu Lys Leu Ser Ala Met Arg Glu Ala Leu Ser Ala Ile Gly
    450                 455                 460

Gly Leu Asp Glu Val Pro Leu Gln Arg Gly Val Ala
465                 470                 475

<210> SEQ ID NO 10
<211> LENGTH: 391
<212> TYPE: PRT
<213> ORGANISM: E. coli

<400> SEQUENCE: 10

Met Asp Thr Ser Leu Ala Glu Glu Val Gln Gln Thr Met Ala Thr Leu
 1               5                  10                  15

Ala Pro Asn Arg Phe Phe Met Ser Pro Tyr Arg Ser Phe Thr Thr
            20                  25                  30

Ser Gly Cys Phe Ala Arg Phe Asp Glu Pro Ala Val Asn Gly Asp Ser
        35                  40                  45

Pro Asp Ser Pro Phe Gln Gln Lys Leu Ala Ala Leu Phe Ala Asp Ala
    50                  55                  60

Lys Ala Gln Gly Ile Lys Asn Pro Val Met Val Gly Ala Ile Pro Phe
65                  70                  75                  80

Asp Pro Arg Gln Pro Ser Ser Leu Tyr Ile Pro Glu Ser Trp Gln Ser
                85                  90                  95

Phe Ser Arg Gln Glu Lys Gln Ala Ser Ala Arg Arg Phe Thr Arg Ser
            100                 105                 110

Gln Ser Leu Asn Val Val Glu Arg Gln Ala Ile Pro Glu Gln Thr Thr
        115                 120                 125

Phe Glu Gln Met Val Ala Arg Ala Ala Leu Thr Ala Thr Pro Gln
    130                 135                 140

Val Asp Lys Val Val Leu Ser Arg Leu Ile Asp Ile Thr Thr Asp Ala
145                 150                 155                 160

Ala Ile Asp Ser Gly Val Leu Glu Arg Leu Ile Ala Gln Asn Pro
                165                 170                 175

Val Ser Tyr Asn Phe His Val Pro Leu Ala Asp Gly Gly Val Leu Leu
            180                 185                 190
```

```
Gly Ala Ser Pro Glu Leu Leu Leu Arg Lys Asp Gly Glu Arg Phe Ser
            195                 200                 205
Ser Ile Pro Leu Ala Gly Ser Ala Arg Arg Gln Pro Asp Glu Val Leu
        210                 215                 220
Asp Arg Glu Ala Gly Asn Arg Leu Leu Ala Ser Glu Lys Asp Arg His
225                 230                 235                 240
Glu His Glu Leu Val Thr Gln Ala Met Lys Glu Val Leu Arg Glu Arg
                245                 250                 255
Ser Ser Glu Leu His Val Pro Ser Ser Pro Gln Leu Ile Thr Thr Pro
            260                 265                 270
Thr Leu Trp His Leu Ala Thr Pro Phe Glu Gly Lys Ala Asn Ser Gln
        275                 280                 285
Glu Asn Ala Leu Thr Leu Ala Cys Leu Leu His Pro Thr Pro Ala Leu
        290                 295                 300
Ser Gly Phe Pro His Gln Ala Ala Thr Gln Val Ile Ala Glu Leu Glu
305                 310                 315                 320
Pro Phe Asp Arg Glu Leu Phe Gly Gly Ile Val Gly Trp Cys Asp Ser
                325                 330                 335
Glu Gly Asn Gly Glu Trp Val Val Thr Ile Arg Cys Ala Lys Leu Arg
            340                 345                 350
Glu Asn Gln Val Arg Leu Phe Ala Gly Ala Gly Ile Val Pro Ala Ser
        355                 360                 365
Ser Pro Leu Gly Glu Trp Arg Glu Thr Gly Val Lys Leu Ser Thr Met
370                 375                 380
Leu Asn Val Phe Gly Leu His
385                 390

<210> SEQ ID NO 11
<211> LENGTH: 23
<212> TYPE: DNA
<213> ORGANISM: Arabidopsis thaliana

<400> SEQUENCE: 11 gggataagg ggttctcaca ata                                      23

<210> SEQ ID NO 12
<211> LENGTH: 24
<212> TYPE: DNA
<213> ORGANISM: Arabidopsis thaliana

<400> SEQUENCE: 12
ctgccctagt tacaacccga aaag                                    24

<210> SEQ ID NO 13
<211> LENGTH: 19
<212> TYPE: DNA
<213> ORGANISM: Arabidopsis thaliana

<400> SEQUENCE: 13
tgtgtttggt cattggtgt                                          19

<210> SEQ ID NO 14
<211> LENGTH: 22
<212> TYPE: DNA
<213> ORGANISM: Arabidopsis thaliana

<400> SEQUENCE: 14
tcatagagtc atagtcgctt ca                                      22
```

-continued

<210> SEQ ID NO 15
<211> LENGTH: 5099
<212> TYPE: DNA
<213> ORGANISM: Arabidopsis thaliana
<220> FEATURE:
<221> NAME/KEY: misc_feature
<222> LOCATION: 4049
<223> OTHER INFORMATION: n = A,T,C or G

<400> SEQUENCE: 15

```
ggatccgctc aactcttttg atccttgagg atgatcacga ccgaatgctt tgaggagaag      60
agtggtttat ttttgttgta ttgacaaaaa cttctacaat aactttgttt tgctttgaca     120
tttctcacaa tttttatctg tctagattcc aaaagcgatt tttaagtgtc cttgcaccca     180
ctcaaattct gatgattttc tatccaccta atgtggattt cactttaatt ctcttttttct   240
aattaaaata agctactgta ttttttttcc ttagcttgag acattttta aagttttta      300
ttttgaaatc gtcactttct aaaatatatg atttgtagtt tcaactaaaa gcggatgaca    360
aaagaaaatt gtagttattt tcccaatttt tttgaatcca tagttagtta attatttggg    420
taatattaca aagtagtcaa aatttgaatc aaaataaagt aattaactat tgtcagtttt    480
ttatcggtaa atgaacatat gacgtcacaa taaaagacaa aaatatccca acaagtcgaa    540
ccaaaaacaa acacttgcgg aaaaaaaaac atagatatga aagattttaa caaaagtaac    600
atttataac gaactttttg aaaattagca tgttatatta aaataccat ttcactttaa      660
aaaaagtaca atgtgaaata aaataataac atgatatgta ttataatagc gtgtcaaata   720
aaaaacaaag ctgattaata ttaaaagta acatgaaatc ttaagaaact attcattttc    780
aaccgtcaat tagtattgta attaaaaagt gtgtaagact caaagaatac tattggatca   840
aatggttatg ggcttcgttt acgagagaga cgcgatgggt tgagtccttt gttttagcaa   900
agaaaatttt ttagaaattt ctaaaaatag cactaaaaca agtttatgg acaataatag   960
cacacactcc atagacttct aaaaatagca ttatttgact tactatgaag ttttttgttct 1020
aaaagtatta tcactaattt attttttcaa taataccaca atatttatat aaaacctatt  1080
caaccaaaat aaattagaaa taaatttaaa atattatatt tgggttctgt atttccaatt  1140
tatggtatat atttcaacca tttaaaagaa attttgatca ttttaatatt actttatggt  1200
attatatttg ggttccctct ttccaattta tgatatatat tttcactgtt taaaagagat  1260
ttttcattt aatattagtt tgtggtatta tatttgggtt ctctatttcc aatttagggt  1320
atatatttcc actatttaaa aaaatgtga ttcaatttaa tattagtgtt tgctctcatt   1380
tttatttggg agattgacac aaatgacact taaaaacttt attatttaat taatttctaa  1440
agaattaaaa actttatgtg ctatttttgg aagtttaaaa aaaagtgtt attttttggaa 1500
taataaagtt tttaatgtca tttgtgtcaa ttccacaaaa attaaaaact tttataccaa  1560
catacaaacg aagtcatttt gagtagacac ctcatcatgc atgtgttagc tgactcaaca  1620
acctattaat tacacaaaat ttcaaatcga aaactatact atacagattg tatgagcata   1680
aaaatattaa ttcaagacga agtcattaaa atatcgaaaa ctatactata cagattgtat   1740
gagcataaaa atattatatt ttcatcacaa aagaatcatc tacagtaaaa acgtatatat   1800
aatagttttt ataatcatat atatgaaagt tggccaactc tctccatatg attgatacat   1860
catcactta acatttgata tatcatcact ttaacatta ccatgtgtcc actgaataat    1920
taatgtaagc tcttcaactt ttaattttta gattaatgat gtatttatta tttaatttta  1980
```

-continued

```
ctaatacata atttattttg ttattacatg ttcttcaata aaattatttt attggttttc      2040
tcatactcga agaatttttt ctgtaatctt aactcaaatt atgagtgtat agtagttatg      2100
gattagttaa taatttgaat agtttgcata ttgttatata tctatatagt aaatcgccga      2160
gggtgaagag tatgtaagaa gtttaatcat caaattctta ggtttcgaga atctcaatat      2220
taccttctat ttaattagtt taagacgaac attgtttagg aattgtgtgt ataatgcatt      2280
gttgaaaatg ttgttaggaa aaaatatttt aatactaaaa ataattactt attacataag      2340
taaatgatta gataattaaa aattatattt aaattaaacg atacaaaaaa tctaaaaata      2400
ctgcagcgta acgtgggtaa ttacctagtt tgtaataaat aataattcaa gacgttagaa      2460
aaagagagga taattcactg ctcttctata cactatttgt tcatatttaa attctttatt      2520
cttttcatat cattggtagt ttatatatat attatgtagt tatttaatcc ttgtttgatt      2580
gtttctatgt atcgaccaaa aaatataca aagttgaatc ttaaaatatt gttttcatat      2640
taatattcta aactttggta aagttgtaag ttataaaaca acttgaacat aaaaataatg      2700
attgaaatta atgagagaac acaaaataga aaaaaaaagg tcatgagaac agaacagaaa      2760
cacttttgtg gctttcgtgg gctaaagacg tgcacgcaga cacaacccta acatctctc      2820 cctctctcac caactctttc tctttaccca ctgcacctac ccccaaacaa tccctttta      2880 catctctcat tcctctgctc atgattcttt gtctcttcct ctgatttctc aatcctctgt      2940
tttctccgtc tcctctgttt ttttcacatc aatggaagcg tcattgttga tgagatcgtc      3000
ttgttgctcc tctgcgattg gtgggttctt cgaccatcga cgtgaattat caacctcaac      3060
acccatttcc actcttcttc ctcttccatc aaccaaatct tctttctctg ttcgttgttc      3120
tcttcctcag ccatcaaagc cacgctctgg aaccagctct gttcacgccg ttatgacact      3180
cgctgggtac gaaagtctca atctttagat tctaattgag aaattgagat tacccttttt      3240 gttaccttc atgatttgta gattcccatt gtgaaattaa cataacccctt tgtgattttg      3300 tagcttaaat tagaaaccctt tatgttcttc ttagatgaat ttgaagcaaa gttttgtttt      3360
tgtttgttgt tgttgttgat atagatcgtt gacagggaag aaacgagtgg atgagagtga      3420
gagtttgact cttgaaggta ttagaaactc tttgatccgt caagaggaca gcattatatt      3480
tgggctattg gagagagcca agtactgtta caatgctgat acttatgatc ctactgcttt      3540
tgacatggat ggtttcaatg gttctttggt tgagtacatg gttaaaggca ctgagaagct      3600
tcacgctaag gtaacaaaca catgctcttt attaacatac cctcaagatt gaaacttgac      3660
tttgttatgg aacttgatta ggttggtagg tttaagagtc ctgatgaaca tcctttcttc      3720
cctgatgatc taccagagcc tatgttgcct cctcttcagt acccaaaggt actcaatata      3780
catgtttcac atgaaaaaag atcgtctcct ttatgttttc ttgcatctta ccgatatggt      3840
ttcttgatgt tcggtgaagc aatgtgtaat cttgtttgag atgtgttttc aacttctgta      3900 cttttggtgct gaggattcaa gtttctttct tattgtatag gtgttgcatt ttgctgctga      3960
ttcgataaac ataaacaaga agatatggaa catgtacttc agagaccttg ttccaagact      4020
tgtgaagaaa ggcgatgatg gtaactacng ctcaacagct gtctgtgacg ctatctgcct      4080
tcaggtttgt tccttttttt cctttttgtta ggtatcagaa acaagcttgg atatttgttt      4140
aaaaacttgt cacctctttt ctaagtcgat taacgtctca tgtagttttt gatgtccatt      4200
gcagtgtctc tcaaagagaa tccattacgg taaatttgtt gcagaagcta aatttcaagc      4260
ctcacccgaa gcatacgagt ccgccatcaa agcacaagta tttatctact tctctaaagc      4320
tctcacatac acacaaaaac tcgaagttta tgcattactt accttttgac atggcaacat      4380
```

-continued

```
acgcattgca ggataaggat gcactgatgg atatgctgac attcccgact gtggaagatg     4440
cgataaagaa gagagttgag atgaaaaccc gaacatacgg gcaagaagtg aaagttggga     4500
tggaggagaa agaagaagaa gaagaagaag ggaatgaatc tcatgtttac aaaatcagtc     4560
cgatcttagt tggtgactta tatggagatt ggatcatgcc tttaacaaaa gaggttcaag     4620
tggagtactt gctcagaaga ctggactaag gcaacaacaa aataaacaat atggctttgg     4680
tagtagagta gaaaggtttt tgaatgttct ttggtttttt tttttttactt tacaatattt     4740 ctaaacgttg ttacactatt attccactgt acaaagcgtg catggtcagt ggtattgaag     4800
aagggtaatt agccgttact caaacggtgt cgtttatgta catactctca attgtggaaa     4860
cctgtatatg agttttagtc gctcttattt gttttggaga tgtatttttt tgtgtgttag     4920
tgcctgtaga atgataattg gctgcttagt gtagtggtca ccactggtta tatggagttt     4980
gactcgtctc atatggagtc cgactccatc cattgtaaaa gtggaaatgg gtcactagga     5040
gagagccttc tcgtcatcct cctgtgttaa cttacaagga aagagccttc tagtcatcc      5099
```

<210> SEQ ID NO 16
<211> LENGTH: 6915
<212> TYPE: DNA
<213> ORGANISM: Arabidopsis thaliana

<400> SEQUENCE: 16

```
tcaaagtctt gaataacaat aaaattatgt tcagctgaga gtctgagacc gcgtccaaca       60
ttttaaaaca cttttaaaag tcatactata atatctgagg accgtgtcta gtttcagttt      120
attcggtttt acaacagcaa tgatgcttgt tgaattatgg tttcattcta ttggattatc      180
tgcaagactt cttaatttta atatatagct cgtgatgata aataacaat ttgacttcta       240 aagtctagtc ctttatagtc ttaacaatat tcattttgac caggttgagt aaatcagaca      300
aaaatctaaa gacaaagaat aatcgtttcc tcaaatatgt acttggtgag ccgtcttaat      360
caccatatgt acatgagaat aaatgtgtaa tttggtggtt atttcataga aattttgggg      420
aaattgttgc acctctccac tctttgccag tctcgtgtga tcttaattga ctcaaaatga     480
aagaaaaaaa aacatgaaat taaagcaaat attcctattt gaattatgtt cctttaagat      540
ttttaacaat attttttaaa tgataaaaac tggtctcaaa gagcctaagt gggtttccta      600
gcaaaaaaag atactcaaag taatttactc ctcaaaataa tgcaatgatc taatgaagat      660
ctgttcaaat agtattgatt ttccaaattt aattatactc aaagagtttt aaaatctgtt      720
cttgttattc tatgctttgt tttacatgta aagtacttaa attcacttga tatttgttat      780
tactataatt ttagaaatgt gtcaaaattt aaaggagcat gcgtgtaatg ccatatgcct      840
tatgtacgag aacttgtaat gcgtttgcaa tttgtagtga catgtaatgt tttttacgat      900
agtttaaagt gcaaaccgct tccgtatcaa acgagaagag tcgtctagca tacaacaccc      960
acacgagagg aaccgcttag aaagagaatc cacttgaaat tgctgtccat gcattgctca     1020
aattcattga tacttggtct atgcaatttt acactacctc atttctgact atttcaattt     1080
gtcaagatat tataacatgc atttataact tttttgtcga cgataaatca accaaacgaa     1140
tccggtctgt atgtttgata acatgcattc atacaaaacg attatctgtt ttttagtcta     1200
tttaatttgg tttctacttt ttacttttgt gaaactaata ataatagatc aaacaattaa     1260
ctgatataat ttattaattt aattcttaga ccaagtaaat gattcatgaa atattaaatg     1320
cacgactaac tttagaaaaa tgtttctttg tatacataaa gatagaatag aagaaaagta     1380
```

-continued

```
ggattagaag aaaaaaacga aaatttcaga gtagtttact aaagaaattc tgagaaattt    1440
tgtgtgaaaa tgaaatgaaa atcttcaatt ttagtgggcc cctgctacat cagtcccta     1500
tttatatctc ttctcaactc taaacccaaa ccaaaaaaaa acagaaagag caatctctct    1560
atactacaaa caccaaagtt taaaattaaa caaaatcttc aagaaacact ttacgaattt    1620
ctgcaatggc ttcacttcaa tttcttctc agtttctggg ctcaaacact aaaacacaca     1680
gctctatcat ttccatctct cgtagttact ctccaactcc attcactaga ttctcccgca    1740
aggtcttttt tctgttttgt tttgttttt tcaattctgt tctttttttt ggaggaattc     1800
ataatgatta acttaatttt attggataat tttcagaagt atgagtcatg ttcgatgtct    1860
atgaatggtt gtgatggaga tttcaagacg ccacttggta cagtggagac aaggactatg    1920
actgctgttt tatctccggc agccgccact gaaaggctaa tctccgccgt tctgaactc     1980
aaatctcaac ctccgtcgtt ttcctccggc gtcgttcggt tacaggtaca tcactacatc    2040
atcatcatca tcatcatcct ctgttttttt cttctaagac acaatccgat ttgctgctgt    2100
atgtgaaaga atgagatcac gccacgtggt gttttacat tggtctgtgg tgatttcgtt     2160
ctctagcttg ctgtcttgct gcatcgttta tgcctaatca tttaagatcc taatcgttat    2220
gattattaaa atcatactat aaagcagagc tcacaacaac gataaatata tccaaatcta    2280
acagttaatc ataaactatt agaagatgac taataattat caaaaagata tggttattat    2340
atttcttatt agtttatgaa taaaacacac actcgaactc ggtcgtacaa gattccgtga    2400
gtccatcgaa ctatttaatt gggacttttg ggacctttac atgtaaatta taatgaatat    2460
tttcttttag tcaattttac gtagactaaa tcaaatacat tttagaaaga ataatcatgt    2520
ttttttagtc ctcgaaatct aatttaacac tgttaacttt tagttagtgt ggccatgcta    2580
agataattta gctagaaaag taataatttt gtgttttgtg ggccagaaaa taagtaaaat    2640
aatgattaga atccaatttg ttgtaaaggc aaggcggcga tcaaatacag tcactctcat    2700
taaaacgcag agttttttaa aaaacccaaa tcacagtcga attttcccgc gcaataaacc    2760
ctaatttgga tttggtgcag gttccaattg accagcaaat cggagcaatt gattggcttc    2820
aagcccagaa tgagattcag cctcgctgtt tcttctctcg tcgcagtgac gttggtcgtc    2880
ccgatcttct tctcgatcta gctaacgaga acggaaacgg aaacgaaaac ggaacagtgt    2940
catctgatcg taatctggtt agcgttgctg gtatcggctc tgcagttttc ttccgtgacc    3000
ttgatccttt ctctcatgac gattggagat ccatcagaag gttttttgtct tcaacgtcac   3060
ctctgattcg tgcctatggt ggtatgcgtt ttgatcctaa tggcaagatc gctgttgaat    3120
gggaaccttt tggtgcattt tacttttcag tccctcaggt acctttaaag attgattctt    3180
tataagagat tttttgagtt tgtgttgttg tttaactggc tgatacatgt gcaggttgag    3240
tttaatgagt ttggtggaag ttcaatgttg gctgcaacta ttgcttggga tgatgaactc    3300
tcttggactc tggaaaatgc tattgaagca ctccaggaga ctatgcttca gtttcttct    3360
gttgtaatga agttgagaaa cagatcttta ggagtatctg ttttaagcaa gaatcatgtt    3420
cctaccaaag gagcttattt ccctgctgta gagaaggctt tagagatgat taaccagaaa    3480
agttcacccc ttaacaaggt agtttagact ttagagattg tgttcgtatc tattcttaaa    3540
acaagtttat aggtttcgtt ttaactgatg tttttggctc gtggaattag gttgttcttg    3600
ctcgtaacag caggataatt acggataccg acattgatcc cattgcttgg ctagcacagt    3660
tacaggtgtg tttttatctc tggatattat atagtagtca gttttcaatg tttagattta    3720
tatctcacta attttttttgt gtgacagcgt gaagggcatg atgcatatca gttctgtctt    3780
```

-continued

```
caaccacctg gtgcaccagc tttatcgga aacacggtag gtctttttat atgtagtctg    3840
tgataataag ttctgttgat aaagatatgt gcacatttgt tatttatttc taagaaatat    3900
gtttgtgaca tacatctttg tgaaacagcc tgagagacta ttccaaagga ctcaattagg    3960
tgtctgcagt gaagctttgg ctgcaactag gcctagagct gcttctagtg ctcgtgatat    4020
ggagatagag cgtgacttac taaccaggtc aattttttact tcaagtgctt tgaacaatta    4080
cagaatccag ttctccatta tcattttact gaattttgc taaactgttg cagtccgaaa    4140
gacgacctcg agttctctat cgtacgagag aatataagag aaaagttaaa cgtaagttca    4200
atcttgatgc tctgcagctt caatgcttca tttcttggat aatagtttgg tatattttt    4260
cttattatgc tttcttctgc tttgcagggt atatgtgaca gagttgttgt caagcctcaa    4320
aaaactgtga ggaagcttgc aagagtgcaa catctatatt ctcaattggc agggagactt    4380
acgaaggaag atgatgaggt gagataatag tattggaata gtttttacat ttccaagctc    4440
ttcatttctt cgaattagct ttaaccctt ttctttctat ctgtctatag tataaaatat    4500
tggctgctct gcatccaact ccagctgttt gtgggcttcc agcagaagaa gcaaggcttt    4560
tgattaagga gataggtaaa atatctacct tggttcaact atcttctagt aactatagat    4620
gtagagatta agaattatgc tgactcaaac attttgcttc ttctagaatc attcgataga    4680
ggaatgtatg cgggacctat tggatttttt ggtggcgagg agagtgaatt tgcagtcggg    4740
atcagatcag ctctagtcga aaaggtgagc ttatttgatc tctttctccc tttaaaaaac    4800
acactttaac actaattgtt atagcaaaat cgatcattac ggttttttgct acaacttgta    4860
aaaaaatgct gaactgtatt ttgatttaca gggtcttggg gcattgatct atgcggggac    4920
agggatagta gctggaagtg acccatcttc agagtggaat gagcttgatc ttaagatatc    4980
tcaggtacga gcttttgtcc agaaaatgtt tagtgacatc atggttctct gttaccaaaa    5040
tcctaatttt tattctctct tttgttgttg tttttgcagt tcaccaagtc aattgaatat    5100
gaagcaacaa catctctaca ggcgattaat tgaagaaaga gtaacatttg tatttgattg    5160
ttttgtttgt atgggggata agggttctc acaataagaa agcaatgttg tctctcttgt    5220
aaattaaaaa agaaatgctt taatttgtta atgggccgag ccttttcggg ttgtaactag    5280
ggcaggccta tcatgaatgt tcataggcct agctgttatg attgttaatg agcttctata    5340
gtgttttct tcaaagacag atatattcaa tatggatcta aaactgaact gaatttaact    5400
gacatgacaa tcgaatcaaa ttgaatttat tttttcaatt ttcatttagc aagaagtgac    5460
ccatcttcag agtgaagtaa tctatgctta ttatctcgat taagcaaaaa tccgtagaat    5520
gcttgggcct ttcaacgatg atgtagccgt gtaggacagg tttacggaat ctgcttttat    5580
gcaaatggta atattaata ttcctttata agttagcgtt tcagatcatc ttctttcgtt    5640
agattaagaa actactttgt tattatataa ctataaatac catccaacaa ccttactcgc    5700
catatctttt catgtgtggt ggtttatagg aacattgaaa agtaccatat tataaaatga    5760
agaatcaaca cgtcaacaaa aacacaaata aaatgagata gtacaattaa aaaaatggag    5820
cgcatgtaaa aagtgaagaa tcaaacgaag gcttggcgat agagaatgga atcagatttc    5880
ccattatccc cactctaaca ccatatattc ctttcccttt ttaccctcca cctcaattag    5940
gtttattaat catatttaac actctaatta accaacccat ttcatctctt ttattttact    6000
aatcacaatg ctttggcctc attacgtttt acctagattt actttgtcac aaactacaca    6060
aatatgaacc taattatcta cactcgtgtc agaaacagtt ttagctaata tttagtaagt    6120
```

```
tttaattaaa actaatgaaa tgaataaata gtgtatagta cataggattt gttttttagtt   6180 tattaatgga aattaagatt tcattagtac taaaaacatg taaataaaat aaagctttaa   6240
agaggaatat attcaaataa aaaaagcaag acctcgaaaa aaaaactttc tattatctct   6300
cttccgcgat taccgtaatc tctgtcacaa acaacaaaac cttctctctc tcactatctt   6360
aatgagagaa gaagacattc tcgagaaatg agaagactac cactacgatg aacacgacgc   6420
cgtttcactc ggatcctccg ccgtcgagga tccagcgtaa gctcgttgtc gaagttgttg   6480
aagctcgtaa tattctccct aaagatggtc aaggaagctc tagcgcttac gtcgttgtcg   6540
atttcgatgc tcagaagaaa cgaacctcca ctaagttccg tgacctaaac cctatttgga   6600
acgagatgct tgatttcgcc gtctccgatc ccaaaaacat ggattacgac gagctcgata   6660
tcgaggttta taacgataaa agatttggta acggaggtgg ccggaagaat cattttctcg   6720
gtagggttaa gatctatgga agccagttct cgcgaagagg tgaagaaggt cttgtgtatt   6780
tccctttgga gaagaagagt gtgttcagct ggattcgcgg cgagattgga ctcaaaatct   6840
actattacga cgaagccgcc gacgaagaca cggcgggtgg aggtggagga cagcaacaac   6900
aacagcaaca gcaac                                                   6915
```